(12) United States Patent
Veneziano et al.

(10) Patent No.: US 11,410,746 B2
(45) Date of Patent: Aug. 9, 2022

(54) STABLE NANOSCALE NUCLEIC ACID ASSEMBLIES AND METHODS THEREOF

(71) Applicant: Massachusetts Institute of Technology, Cambridge, MA (US)

(72) Inventors: Remi Veneziano, Allston, MA (US); Sakul Ratanalert, Cambridge, MA (US); Tyson Shepherd, Arlington, MA (US); Hyungmin Jun, Arlington, MA (US); Mark Bathe, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 444 days.

(21) Appl. No.: 16/097,596

(22) PCT Filed: Apr. 27, 2017

(86) PCT No.: PCT/US2017/029891
§ 371 (c)(1),
(2) Date: Oct. 29, 2018

(87) PCT Pub. No.: WO2017/189870
PCT Pub. Date: Nov. 2, 2017

(65) Prior Publication Data
US 2019/0156911 A1 May 23, 2019

Related U.S. Application Data

(60) Provisional application No. 62/328,442, filed on Apr. 27, 2016, provisional application No. 62/328,450, filed on Apr. 27, 2016.

(51) Int. Cl.
| | | |
|---|---|---|
| *G16B 15/00* | (2019.01) | |
| *G16B 15/10* | (2019.01) | |
| *C12N 15/10* | (2006.01) | |
| *A61K 47/26* | (2006.01) | |
| *C12N 15/11* | (2006.01) | |

(52) U.S. Cl.
CPC .............. *G16B 15/00* (2019.02); *A61K 47/26* (2013.01); *C12N 15/10* (2013.01); *G16B 15/10* (2019.02); *C12N 15/11* (2013.01); *C12N 2320/32* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly |
| 5,356,802 A | 10/1994 | Chandrasegaran |
| 5,436,150 A | 7/1995 | Chandrasegaran |
| 5,487,994 A | 1/1996 | Chandrasegaran |
| 5,624,821 A | 4/1997 | Winter |
| 6,140,081 A | 10/2000 | Barbas |
| 6,194,551 B1 | 2/2001 | Idusogie |
| 6,453,242 B1 | 9/2002 | Eisenberg |
| 6,534,261 B1 | 3/2003 | Cox |
| 6,610,512 B1 | 8/2003 | Barbas |
| 6,746,838 B1 | 6/2004 | Choo |
| 6,866,997 B1 | 3/2005 | Choo |
| 7,067,617 B2 | 6/2006 | Barbas |
| 8,227,242 B2 | 7/2012 | Bradbury |
| 8,501,923 B2 | 8/2013 | Rothemund |
| 2002/0165356 A1 | 11/2002 | Barbas |
| 2003/0215914 A1 | 11/2003 | Houtzager |
| 2004/0180422 A1 | 9/2004 | Hoet |
| 2004/0197892 A1 | 10/2004 | Moore |
| 2005/0147962 A1 | 7/2005 | Wagstrom |
| 2007/0117109 A1 | 5/2007 | Rothemund |
| 2007/0128728 A1 | 6/2007 | Bradbury |
| 2007/0154989 A1 | 7/2007 | Barbas |
| 2007/0213269 A1 | 9/2007 | Barbas |
| 2012/0251583 A1 | 10/2012 | Rothemund |

(Continued)

FOREIGN PATENT DOCUMENTS

| | | |
|---|---|---|
| CN | 106119269 | 11/2016 |
| WO | 9853059 | 11/1998 |

(Continued)

OTHER PUBLICATIONS

Shaik et al. in F1000 Research (2015) vol. 4:11 pages.*
Kuang et al. in (Accounts of Chemical Research (2013) vol. 46:2341-2354).*
Abramoff, et al., "Image processing with ImageJ", Biophotonics Int., 11(2):36-42 (2004).
Ailenberg, et al., "An improved Huffman coding method for archiving text, images, and music characters in DNA", BioTechniques., 47:747-754 (2009).
Amunts, et al., "Ribosome. The structure of the human mitochondrial ribosome", Science., 348(6230):95-98 (2015).

(Continued)

*Primary Examiner* — Lori A. Clow
(74) *Attorney, Agent, or Firm* — Pabst Patent Group LLP

(57) ABSTRACT

Methods for the top-down design of nucleic acid nanostructures of arbitrary geometry based on target shape of spherical or non-spherical topology are described. The methods facilitate 3D molecular programming of lipids, proteins, sugars, and RNAs based on a DNA scaffold of arbitrary 2D or 3D shape. Geometric objects are rendered as node-edge networks of parallel nucleic acid duplexes, and a nucleic acid scaffold routed throughout the network using a spanning tree formula. Nucleic acid nanostructures produced according to top-down design methods are also described. In some embodiments, the nanostructures include single-stranded nucleic acid scaffold, DX crossovers, and staple strands. In other embodiments, the nanostructures include single-stranded nucleic acid scaffold, PX crossovers and no staples. Modified nanostructures include chemically modified nucleotides and conjugated to other molecules are described.

48 Claims, 19 Drawing Sheets

Specification includes a Sequence Listing.

(56) References Cited

U.S. PATENT DOCUMENTS

| | | | |
|---|---|---|---|
| 2013/0295614 A1 | 11/2013 | Hareendran et al. | |
| 2019/0203242 A1 | 7/2019 | Praetorius | |

FOREIGN PATENT DOCUMENTS

| | | |
|---|---|---|
| WO | 9958572 | 11/1999 |
| WO | 2000071694 | 11/2000 |
| WO | 2003016496 | 2/2003 |
| WO | 2004048543 | 6/2004 |
| WO | 2007067818 | 6/2007 |
| WO | 2013176772 | 11/2013 |
| WO | 2014018423 | 6/2014 |
| WO | 2017089567 | 6/2017 |
| WO | 2017089570 | 6/2017 |
| WO | 2017189870 | 11/2017 |
| WO | 2017189914 | 11/2017 |
| WO | 2019094928 | 5/2019 |

OTHER PUBLICATIONS

Angal, et al., "A single amino acid substitution abolishes the heterogeneity of chimeric mouse/human (IgG4) antibody", Mol. Immunol., 30:105-08 (1993).
Anonymous, et al., "M13mp18 (Cloning Vector)", New England BioLabs Catalog, http://international.neb.com/-/media/nebus/page-images/tools/dna-sequences-and-maps/1 pagem13mp18_map.pdf?la=en&hash+ABF432A1085CFA7CA7850DOOB69ACBE654DFC 580(2002).
Arita, et al., "Chapter 368: DNA Memory", Handbook of Natural Compu, 1281-1318 (2012).
Arizona State University, "Top-down design brings new DNA structures to life", retrieved from the internet: URL:https://phys.org/news/2016-05-top-down-dna-life.html :1-4 (2016).
Babaei, "A novel text and image encryption method based on chaos theory and DNA computing", Nat Comput., 12:101-107 (2013).
Bai, et al., "Cryo-EM structure of a 3D DNA-origami object", Proc. NatL Acad. Sci. 109, 20012-20017 (2012).
Benson, et al., "Computer-Aided Production of Scaffolded DNA Nanostructures from Flat Sheet Meshes", Angewandte Chemie, 55(31):8869-8872 (2016).
Benson, et al., "DNA rendering of polyhedral meshes at the nanoscale", Nature, 523:441-444 (2015).
Benson, et al., "Supplementary Information to DNA rendering of polyhedral meshes at the nanoscale", Nature, 523(7561):441-444 (2015).
Bent, et al., "On non-intersecting Eulerian circuits", Discrete Appl. Math. 18(1):87-94 (1987).
Bhatia, et al., "Icosahedral DNA nanocapsules by modular assembly", Angew. Chem. Int. Ed., 48(23):4134-4137 (2009).
Bornholt, et al., "A DNA-based Archival Storage System", 21th ACM International Conference on Architectural Support for Programming Languages and Operating Systems, 1-13, (2016).
Braasch, et al., "Locked nucleic acis (LNA): fine-tuning the recognition of DNA and RNA", Chem. Biol., 8(1):1-7 (2001).
Brown, et al., "An easy-to-prepare mini-scaffold for DNA origami", Nanoscale, 7:16621-4 (2015).
Brudno, et al., "Recent progress toward the templated synthesis and directed evolution of sequence-defined synthetic polymers", Chern Biol., 16(3):265-276 (2009).
Castro, et al., "A primer to scaffolded DNA origami", Nat. Methods., 8(3):221-229 (2011).
Chandran, et al., "DNA origami: Folding DNA into Desired Shapes", Fourth Warft Workshop on Brain Modeling and Supercomputing, (2009).
Chasteen, et al., Eliminating helper phage from phage display Nucleic Acids Res., 34(21):e145 (2006), 11 pages.
Cho, "An unnatural biopolymer", Science, 261(5126): 1303-1305 (1993).

Church, et al. "Next-generation digital information storage in DNA", Science, 337(6102):1628 (2012), 2 pages.
Clelland, et al., "Hiding messages in DNA microdots", Nature, 399(673):533-534 (1999).
Cong, "Multiplex genome engineering using CRISPR/Cas systems", Science, 15:339(6121):819-823 (2013).
Cui, et al., "An encryption scheme using DNA technology", 2008 Third International Conference on Bio-Inspired Computing: Theories and Applications., 37-41(2008).
Dietz, et al., "Folding DNA into twisted and curved nanoscale shapes", Science, 325(5941):725-730 (2009).
Dotto, et al., "Initiation and termination of phage f1 plus-strand synthesis", Proc. Natl. Acad. Sci. U.S.A., 79:7122-7126 (1982).
Douglas, et al., "Self-assembly of DNA into nanoscale three-dimensional shapes", Nature, 459(7425):414-418 (2009).
Douglas, et al., "A logic-gated nanorobot for targeted transport of molecular payloads", Science, 335(6070):831-834 (2012).
Douglas, et al., "Rapid prototyping of 3D DNA-origami shapes with caDNAno", Nucleic Acids Res., 37:5001-5006 (2009B).
Dunn, et al., "Guiding the folding pathway of DNA origami", Nature, 525(7567):82-86 (2015).
Dutta, et al., "DNA-directed artificial light-harvesting antenna", Journal of the American Chemical Society, 133(31):11985-11993 (2011).
Elbashir, et al., "Duplexes of 21-nucleotide RNAs mediate RNA interference in cultured mammalian cells", Nature, 411:494-498 (2001).
Elbaz, et al., "Genetic encoding of DNA nanostructures and their self-assembly in living bacteria", Nat Commun, 7:11179 (2016), 11 pages.
Ellis-Monaghan, et al., "DNA origami and the complexity of Eulerian circuits with turning costs", Nat. Comput., 14(3):491-503 (2015).
Ennifar, et al., "Targeting the dimerization initiation site of HIV-1 RNA with aminoglyocosides: from crystal to cell", Nucleic Acids Research. 34, 2328-2339 (2006).
Faber, et al., "Structural Rearrangements of HIV-1 Tat-responsive RNA upon Binding of Neomycin B", The Journal of Biological Chemistry. 275:20660-20666 (2000).
Fan, et al., "Gating machinery of InsP3R channels revealed by electron cryomicroscopy", Nature, 527:336-341 (2015).
Fang, et al., "An unusual Toplogical Structure of the HIV-1 Rev Response Element" Cell, 155:594-605 (2013).
Fang, et al., "Small-angle X-ray scattering: a bridge between RNA secondary structures and three-dimensional topological structures" Current Opinion in Structural Biology. 30, 147-160 (2015).
Fire, et al. "Potent and specific genetic interference by double-stranded RNA in Caenorhabditis elegans", Nature, 391(6669):806-11 (1998).
Fu, et al., "Controlled drug release by a nanorobot", Nature Biotechnology, 30(5):407-408 (2012).
Fu, et al., "DNA double-crossover molecules", Biochemistry, 32(13):3211-3220 (1993).
Geary, et al., "RNA nanostructures. A single-stranded architecture for cotranscriptional folding of RNA nanostructures", Science, 345:799-804 (2014).
Gehani, et al., "DNA-based Cryptography", Leet Notes Comput Sc., 2950:167-188 (2004).
Gellman, "Foldamers: A Manifesto", Acc. Chern. Res., 31(4):173-180 (1998).
Goldman et al., "Towards practical, high-capacity, low-maintenance information storage in synthesized DNA", Nature, 494(7435):77-80 (2013).
Gradišar, et al., "Design of a single-chain polypeptide tetrahedron assembled from coiled-coil segments", Nat. Chem. Biol., 9(6):362-366 (2013).
Grass, et al., "Robust chemical preservation of digital information on DNA in silica with error-correcting codes", Angew. Chern. Int. Ed., 54(8):2552-2555 (2015).
Gruber, et al., "Efficient tumor cell lysis mediated by a bispecific single chain antibody expressed in *Escherichia coli*.", J. Immunol., 152(11):5368 (1994), 8 pages.

(56) References Cited

OTHER PUBLICATIONS

Gu, et al., "Dynamic patterning programmed by DNA tiles captured on a DNA origami substrate", Nature Nanotechnology, 4(4):245-248 (2009).
Han, et al., "DNAgridiron nanostructures based on four-arm junctions", Science. 339(6126):1412-1415 (2013).
Han, et al., "DNA origami with complex curvatures in three-dimensional space", Science, 332(6027):342-346 (2011).
Han, et al., "Single-stranded DNA and RNA origami", Science, 358(6369) (2017), 25 pages.
Hannon, "RNA interference", Nature, 418(6894):244-251 (2002).
He, et al., "Hierarchical self-assembly of DNA into symmetric supramolecular polyhedra", Nature, 452(7184):198-201 (2008).
He, et al., "On the Chirality of Self-Assembled DNA Octahedra", Angew. Chem., 122(4):760-763 (2010).
Henderson, et al., "Outcome of the first electron microscopy validation task force meeting", Structure, 20(2):205-214 (2012).
Hollinger, et al., "Diabodies": small bivalent and bispecific antibody fragments, Proc. Natl. Acad. Sci. U.S.A., 90(14):6444-6448 (1993).
Howe, et al., "Seletive small-molecule inhibition of an RNA structural element", Nature, 526:672-677 (2015).
Iinuma et al., "Supplementary Material for Polyhedra self-assembled from tripods and Chracterized with 3D DNA-PAINT", Science, 344(6179):65-69 (2014).
Iinuma, et al., "Polyhedra Self-Assembled from DNA-PAINT", Science, 344(6179): 65-69 (2014).
International Search Report for corresponding PCT application PCT/US2017/029891 dated Jul. 4, 2017.
Jiang, et al., "DNA origami as a carrier for circumvention of drug resistance", Journal of the American Chemical Society 134(32):13396-13403 (2012).
Jinek, et al., "A programmable dual-RNA-guided DNA endonuclease in adaptive bacterial immunity", Science, 337(6096):816-21 (2012).
Jones, et al., "Small-angle X-ray scattering-derived structure of the HIV-1 5' UTR reveals 3D tRNA mimicry", Proceedings of the National Academy of Sciences of the United States of America. 111:3395-3400 (2014).
Kallenbach, et al., "An immobile nucleic acid junction constructed from oligonucleotides", Nature, 305:829-831 (1983).
Kazantsev, et al., Proceedings of the National Academy of Sciences of the United States of America. 100: 7497-7502 (2003).
Ke, et al. "Multilayer DNA Origami Packed on a Square Lattice", J. A. Chem. Soc., 131:15903-15908 (2009).
Ke, et al., "DNA brick crystals with prescribed depths", Nat. Chem., 6:994-1002 (2014).
Ke, et al., "Self-Asssembled Water-Soluble Nucleic Acid Probe Tiles for Label-Free RNA Hyrbidization Assays", Science, 319:180-183 (2008).
Ke, et al., "Three-dimensional structures self-assembled from DNA bricks", Science, 338(611):1177-1183 (2012).
Ke, et al., "Two design strategies for enhancement of multilayer-DNA-origami folding: underwinding for specific intercalator rescue and staple-break positioning",Chem. Sci., 3(8):2587-2957 (2012B).
Keane, et al., "Structure of the HIV-1 RNA packaging signal", Science, 348(6237):917-921 (2015).
Kertesz, et al., "Genome-wide measurement of RNA secondary structure in yeast", Nature, 467:103-107 (2010).
Kick, et al., "Efficient Production of Single-Stranded Phage DNA as Scaffolds for DNA Origami", Nano Lett, 15:4672-6 (2015).
Kim et al., "Extending Lifetime of Flash Memory Using Strong Error Correction Coding", IEEE Trans. Consum. Electron., 61:206-214 (2015).
Kim, et al. "Insertion and deletion mutants of FokI restriction endonuclease", J. Biol. Chem., 269:31978-31982 (1994B).
Kim, et al., "Chimeric restriction endonuclease", Proc. Natl. Acad. Sci. USA., 91:883-887 (1994A).
Ko, et al., "Synergistic self-assembly of RNA and DNA molecules", Nature Chemistry, 2(12):1050-1055 (2010).
Kostelny, et al., "Formation of a bispecific antibody by the use of leucine zippers", J. Immunol., 14 8(5):1547-1553 (1992).
Krishnan, et al., "Designer nucleic acids to probe and program the cell", Trends in Cell Biology, 22(12):624-633 (2012).
Kurreck, et al., "Design of antisense oligonucleotides stabilized by locked nucleic acids", Nucleic Acids Res., 30(9):1911-1918 (2002).
Kuzyk, et al., "DNA-Based Self-Assembly of Chiral Plasmonic Nanostructures With Tailored Optical Response", Nature, 483(7389):311-314 (2012).
Leier, et al., "Cryptography with DNA binary strands", Biosystems, 57(1):13-22 (2000).
Li, et al., "Alteration of the cleavage distance of Fok I restriction endonuclease by insertion mutagenesis", Proc. Natl. Acad. Sci. USA, 90(7):2764-2768 (1993).
Li, et al., "Functional domains in Fok I restriction endonuclease", Proc., Natl. Acad. Sci. USA, 89(10):4275-4279 (1992).
Li, et al., "Nucleic-based nanoengineering: novel structures for biomedical applications", Interface Focus, 1(5): 702-724 (2011).
Li, et al., "Quantifying Absolute Protein Synthesis Rates Reveals Principles Underlying Allocation of Cellular Resources", Cell, 157(3):624-635 (2014).
Liedl, et al., "Self-assembly of 3D prestressed tensegrity structures from DNA", Nature Nanotechnology, 5:520-524 (2010).
Linko, et al., "Automated design of DNA origami", Nature Biotechnology, 34(8):826-827 (2016).
Liu et al., "Crystalline two-dimensional DNA-origami arrays", Angew. Chern. Int. Ed. Engl., 50(1):264-267 (2011).
Liu, et al., "Diamond family of nanoparticle superlattices", Science, 351(6273):582-586 (2016).
Liu, et al., "Quantifying Absolute Protein Synthesis Rates Reveals Principles Underlying Allocation of Cellular Responses", Nano Letters, 12:4254-4259 (2012).
Marchi, et al., "Toward larger DNA origami", Nano Lett, 14:5740-7 (2014).
Masanori, et al., "Chapter 368: DNA Memory", Handbook of Natural Compu, 1281-1318 (2012).
Maxam et al., "Anew method for sequencing DNA", Proc. Nat. Acad. Sci. USA, 74(2):560-564 (1977).
Mercer, et al., "Structure and function of long noncoding RNAs in epigenetic regulation", Nature Structural & Molecular Biology. 20, 300-307 (2013).
Michelotti, et al., "Beyond DNA origami: A look on the bright future of nucleic acid nanotechnology", Wiley Interdiscip Rev Nanomed Nanobiotechnol., 4(2):139-152 (2012).
Morrison, et al., "Chimeric human antibody molecules: mouse antigen-binding domains with human constant region domains", Proc. Natl. Acad. Sci. USA, 81:6851-6855 (1984).
Nafisi, et al., "Construction of a novel phagemid to produce custom DNA origami scaffolds", Synthetic Biology, 3(1), ysy015 (8 pages) (2018).
Napoli, et al., Introduction of a Chimeric Chaicone Synthase Gene into Petunia Results in Reversible Co-Suppression of Homologous Genes in trans., Plant Cell, 2(4):279-289 (1990).
Nelson, "Droplet Actuation by Electrowetting-on-Dielectric (EWOD): A Review", Journal of Adhesion Science and Technology, 26:747-1771 (2012).
Nickels, et al., "DNA origami structures directly assembled from intact bacteriophages", Small, 10:1765-9 (2014).
Nielsen, et al., "Sequence-selective recognition of DNA by strand displacement with a thymine-substituted polyamide", Science, 254(5037): 1497-1500 (1991).
Nogales, et al., "Cryo-EM: A Uniquw Tool for the vizualization of Macromolecular Complexity", Molecular Cell, 58:677-689 (2015).
Olson, et al., "New Structue Sheds Light on Selective HIV-1 Genomic RNA Packaging", Viruses, 7:4826-4835 (2015).
Pan, et al., "Structure-based model for light-harvesting properties of nucleic acid nanostructures", Nucleic Acids Research, 42(4):2159-2170 (2014B).
Pandey, et al., "Algorithmic design of self-folding polyhedral", Proc. Natl. Acad. Sci. 108(50):19885-19890 (2011).
Pardee, et al., "Paper-based synthetic gene networks", Cell, 159(4):940-954 (2015).
Pasqualini, et al., "Organ targeting in vivo using phage dislay peptide libraries", Nature, 380:364-366 (1996).

(56) References Cited

OTHER PUBLICATIONS

Peng, et al., "Bottom-up nanofabrication using DNA nanostructures", Chem Matter, 28(4):1012-1021 (2016).
Praetorius, et al., "Biotechnological mass production of DNA origami", Nature, 552(7683):84-7 (2017).
Prim, "Shortest connection networls and some generalizations", Bell Syst. Tech. J., 36(6):1389-1401 (1957).
Rich, "The rise of single-molecule DNA biochemistry", Proc. Natl. Acad. Sci. U. S. A., 95(24): 13999-14000 (1998).
Rothemund, "Scaffolded DNA Origami: from Generalized Multicrossovers to Polygonal Networks", Nanotechnology: Science and Computation, 3-21 (2006b).
Rothemund, et al., "Algorithmic self-assembly of DNA Sierpinski Triangles", PLoS Biol., 2:2041-2053 (2004).
Rothemund, et al., "Folding DNA to create nanoscale shapes and patterns", Nature, 440(7082):297-302 (2006).
Rouskin, et al., "Genome-wide probing of RNA structure reveals active unfoldinng of mRNA strucutres in vivo", Nature. 505:701-705 (2014).
Said, et al., "M1.3—a small scaffold for DNA origami", Nanoscale, 5(1):284-290 (2013).
Sanger, et al., "DNA sequencing with chain-terminating inhibitors", Proc. Natl. Acad. Sci. U.S.A., 74(12):5463-5467(1977).
Santangelo, et al., "Nanostructred Probes for RNA Detection in Living Cells", Annals of Biomedical Engineering, 34:39-50 (2006).
Seeman, et al., "Design of immobile nucleic acid junctions", Biophys. J., 44(2):201-209 (1983).
Seeman, et al., "DNA nicks and nodes and nanotechnology", Nano Lett., 1:22-26 (2001).
Sharma, et al., "Control of self-assembly of DNA tubules through integration of gold nanoparticles", Science, 323:112-6 (2009).
Shaw, et al., "Purification of functionalized DNA origami nanostructures", ACS Nano, 9(5):4968-4975 (2015).
Shih, et al., "A 1.7-kilobase single-stranded DNA that folds into a nanoscale octahedron", Nature, 427(6975):618-621 (2004).
Siegfried, et al.,"RNA motif discovery by SHAPE and mutational profiling (SHAPE-MaP)", Nature Methods, 11(9):959-965 (2014).
Sinclair, et al., "Generation of protein lattices by fusing proteins with matching rotational symmetry", Nat. Nanotechnol. 6(9):558-562 (2011).
Smola, et al., "Selective 2'-hydroxyl acylation analyzed by primer extension and mutational profiling (SHAPE-MaP) for direct, versatile and accurate RNA structure analysis", Nat Protoc.10(11):1643-1669 (2015).
Sobczak, et al., "Rapid folding of DNA into nanoscale shapes at constant temperature", Science, 338(6113):1458-1461 (2012).
Songsivilai, et al., "Bispecific antibody: a tool for diagnosis and treatment of disease", Clin. Exp. Immunol., 79(3):15-321 (1990).
Specthrie, et al., "Construction of a microphage variant of filamentous bacteriophage", Mol. Biol., 228:720-724 (1992).
Spink, et al., "Thermodynamics of forming a parallel DNA crossover", Biophysical Journal, 97(2):528-538 (2009).
Staple, et al., "Solution structure and thermodynamic investigation of the HIV-1 frameshift inducing element", Journal of Molecular Biology, 349:1011-1023 (2005).
Stephenson, et al., "Three-Dimensional RNA Structure of the major HIV-1 Packaging Signal Region", Structure, 21:951-962 (2013).
Tintore, et al., "DNA origami as a DNA repair nanosensor at the single-molecule level", Angew Chem Int Ed Engl.,52(30):7747-7750 (2013).
Tomley, et al., "M13 Phage Growth and Single-Stranded DNA Preparation", Methods Mol. Biol., 58:359-362 (1996).
Torring, et al., "DNA origami: a quantum leap for self-assembly of complex structures", Chem. Soc. Rev., 40:5636-5646 (2011).
Tumpane, et al., "Triplex addressability as a Basis for Functional DNA Nanostructures", 7(12):3832-3839 (2007).
Ubaidurrahman, et al., "A Novel DNA Computing Based Encryption and Decryption Algorithm", Procedia Comput Sci., 46:463-475 (2015).

Ui-Tei, et al., "Sensitive assay of RNA interference in *Drosophila* and Chinese hamster cultured cells using firefly luciferase gene as target", FEBS Lett, 479(3):79-82 (2000).
Untergasser, et al., "Primer3—new capabilities and interfaces", Nucleic Acids Res. 40(15): e115-e115 (2012).
Vogel, et al., Hfq and its constellation of RNA, Nature Reviews Microbiology. 9:578-589 (2011).
Wahlestedt, et al., "Potent and nontoxic antisense oligonucleotides containing locked nucleic acids", Proc. Natl Acad. Sci. USA, 97(10):5633-5638 (2000).
Wang, "Double-stranded DNA homology produces a physical signature", PNAS, 107(28):12547-12552 (2010).
Watts, et al., "Architecture and secondary structure of an entire HIV-1 RNA genome", Nature, 460:711-716 (2009).
Wei, et al., "Complex shapes self-assembled from single-stranded DNA tiles", Nature, 485(7400): 623-626 (2012).
Wilkinson, et al., "Selective 2'-hydroxyl acylation analyzed by primer extension (SHAPE): quantitative RNA structure analysis at single nucleotide resolution", Nature Protocols, 1(3)1610-1616 (2006).
Winfree, et al., "Design and self-assembly of two-dimensional DNA crystals", Nature, 394(6693):539-544 (1998).
Winter, et al., "Making antibodies by Phage Display Technology", Annu Rev Immunol., 12:433-455 (1994).
Wong, et al., "Organic Data Memory Using the DNA Approach", Communications of the ACM., 46:95-98 (2003).
Woo, et al., "Programmable molecular recognition based on the geometry of DNA nanostructures", Nat. Chem., 3(8):620-627 (2011).
Wooddell, et al., "Use of asymmetric PCR to generate long primers and single-stranded DNA for incorporating cross-linking analogs into specific sites in a DNA probe", Genome Res. 6(9):886-892 (1996).
Wynn, et al., "HIV-1 drug discovery: targeting folded RNA structures with branched peptides", Organic & Biomolecular Chemistry, 13, 5848-5858 (2015).
Xu, et al., "Design of 240,000 orthogonal 25mer DNA barcode probes", PNAS., 106(7):2289-2294 (2009).
Xuan, "Ultrasound-responsive block copolymer micelles based on a new amplification mechanism", Langmuir, 28(47):16463-16468 (2012).
Yan, et al., "DNA-templated self-assembly of protein arrays and highly conductive nanowires", Science, 301:1882-1884 (2003).
Yang, et al, "Self-assembly of DNA rings from scaffold-free DNA tiles," Nano Letters, 13(4):1862-1866 (2013).
Zhang, et al., "Complex wirefram DNA origami nanostructure with multi-arm junction vertices", Nature Nanotechnology, 10: 779-785 (2015).
Zhao, et al., "Organizing DNA origami tiles into larger structures using preformed scaffold frames", Nano Lett., 11(7):2997-3002 (2011).
Zuckermann, et al., "Efficient method for the preparation of peptoids [oligo(N-substituted glycines)] by submonomer solid-phase synthesis", J. Am. Chern. Soc., 114(26):10646-10647(1992).
Banal, et al., "Random access DNA memory in a scalable, archival file storage system", bioRxiv, 1-29 (2020).
Irobalieva, et al., "Structural diversity of supercoiled DNA", Nat. Commun., 6(8440):1-10 (2015).
Jones, et al., "Nanomaterials, Programmable materials and the nature of the DNA bond", Science, 347(6224):840; 1260901-1-12060901-11 (2015).
Li, et al., "Engineering nucleic acid structures for programmable molecular circuitry and intracellular biocomputation", Nature Chemistry, 9(11):1056-1067 (2017).
Lutz, et al., "Sequence-controlled Polymers", Science, 341(6146):628;1238149-1-1238149-8 (2013).
Martin, et al., "Magnesium-free self-assembly of multi-layer DNA objects", Nat. Commun., 3(1103):1-6 (2012).
Nayak, et al.. "Cas9-mediated genome editing in the methanogenic archaeon Methanosarcina acetivorans", PNAS, 114(11):2976-2981 (2017).
New England Bioiabs: Catalog #N4018S, 8 pages (2007).
New England Bioiabs: Catalog #N4040S, 13 pages (2007).

(56) References Cited

OTHER PUBLICATIONS

Norton, et al., "Templates for sequential Assembly of DNA Based Nanostructures", Proceedings of 2005 5th IEEE Conference on Nanotechnology, 3 pages (2005).

Pan, et al., "Lattice-free prediction of three-dimensional structure of programmed DNA assemblies", Nature Communications., 5(5578): 1-7 (2014A).

PartBBa_K1445000, Registry of Standard Biological Parts, Group: iGEM14_CU-Boulder (2014), 1 page.

Perrault and Shih, "Virus-inspired membrane encapsulation of DNA nanostructures to achieve in vivo stability," ACS Nano, 8(5):5132-5140 (2014).

Rashid, et al., "The strategies of DNA immobilization and hybridization detection mechanism in the construction of electrochemical DNA sensor: A review," Sensing and Bio-Sensing Research vol. 16, pp. 19-31,doi:10.1016/j.sbsr.2017.09.001 (2017).

Rhoads, et al., "PacBio Sequencing and Its Applications", Genomics, Proteomics and Bioinformatics, 13(5):278-289 (2015).

Sattar, et. al., "Ff-nano, short functionalized nanorods derived from Ff (f1, fd, or M13) filamentous bacteriophage", Front Microbiol., 6(316):1-13 (2015).

SEQ ID No. 1-139 Alignment, 3 pages (Year: 2020).

Shilling, et al., "Structure and Function of *Escherichia coli* Type 1 Pili: New Insight into the Pathogenesis of Urinary Tract infections", The Journal of infectious Diseases, 183(Suppl.1): S36-840 (2001).

Sun, et al., "Casting inorganic structures with DNA molds", Science, 346(6210):1-24 (2014).

Veneziano, "Supplementary Materials for designer nanoscale DNA assemblies programmed from the top down", Science, 352(6293):S1-S67 (2016).

Veneziano, et al, "Designer nanoscale DNA assemblies programmed from the top down", Science, 352(6293) 1534: 1-21 (2016).

Veneziano, et al., "Enzymatic Synthesis of gene-length single-stranded DNA", bioRxiv, 6 pages (2017).

Wang, et al., "An atomic model of brome mosaic virus using direct electron detection and real-space optimization", Nature Communications, 5(4808):1-12 (2014).

Yazdi, et al., "A Rewritable, Random-Access DNA-Based Storage System", Scientific reports, 5(14138): 1-10 (2015).

Yim, et al., "The Essential Component in DNA-Based information Storage System: Robust Error-Tolerating Module", Frontiers in bioengineering and biotechnology, 2(49): 1-5 (2014).

Zhou, et al., "A new biochromatography model based on DNA origami assembled PPARy: construction and evaluation", Anal. Bioanal. Chem., 409(12):3059-3065 (2017).

* cited by examiner

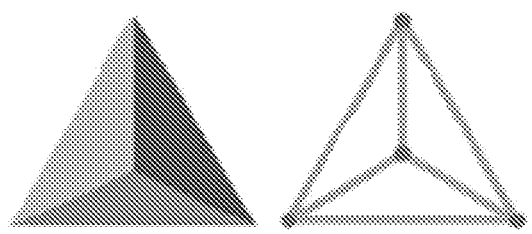
FIG. 3A  FIG. 3B
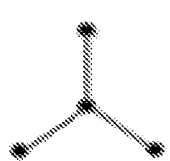 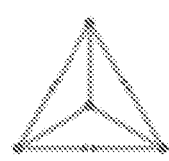 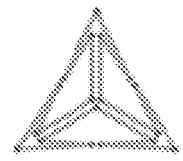 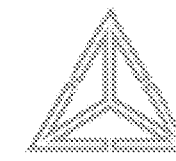 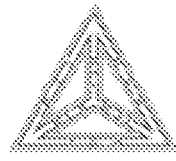
FIG. 3C  FIG. 3E  FIG. 3G  FIG. 3I  FIG. 3K
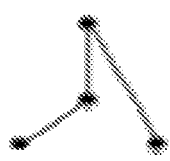 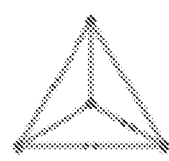 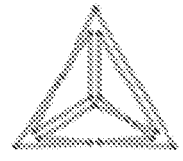 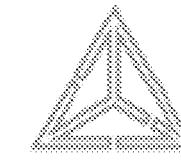 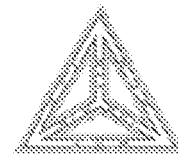
FIG. 3D  FIG. 3F  FIG. 3H  FIG. 3J  FIG. 3L
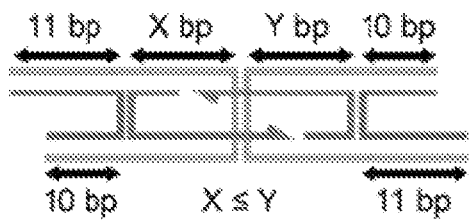
FIG. 3M
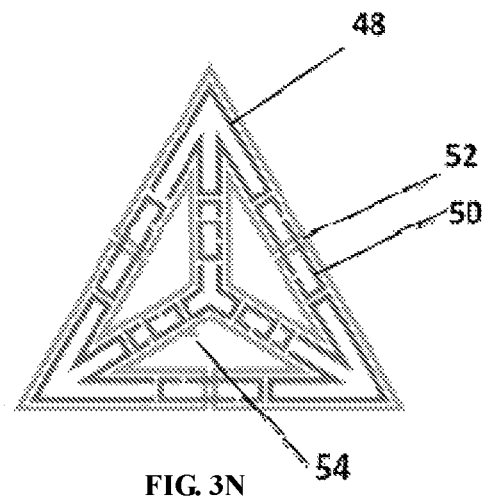
FIG. 3N

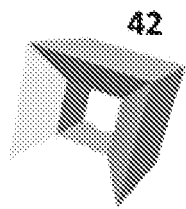
FIG. 4A
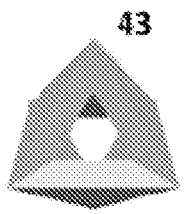
FIG. 4B
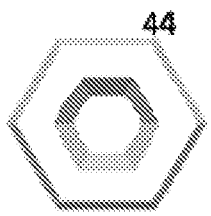
FIG. 4C
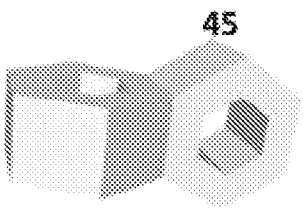
FIG. 4D
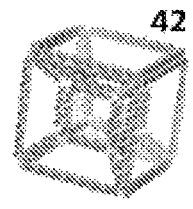
FIG. 4E
FIG. 4F
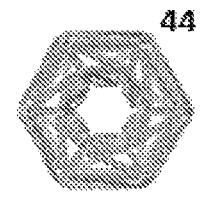
FIG. 4G
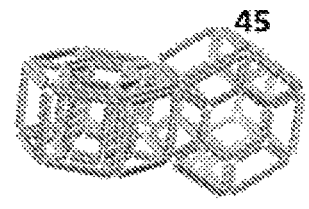
FIG. 4H
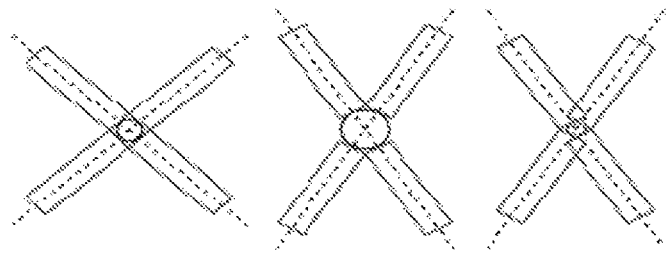
FIG. 5A  FIG. 5B  FIG. 5C
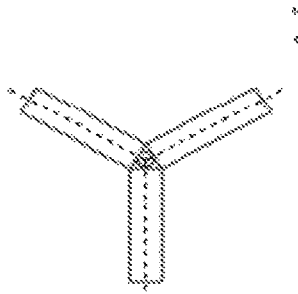
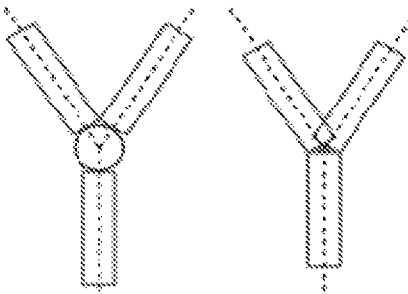
FIG. 5D  FIG. 5E  FIG. 5F

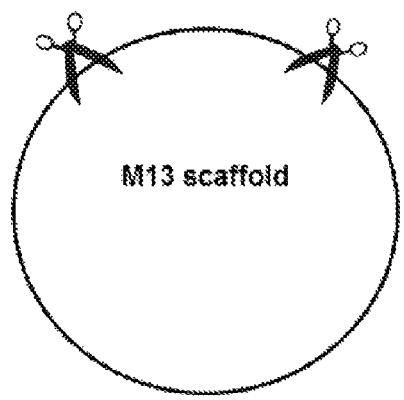
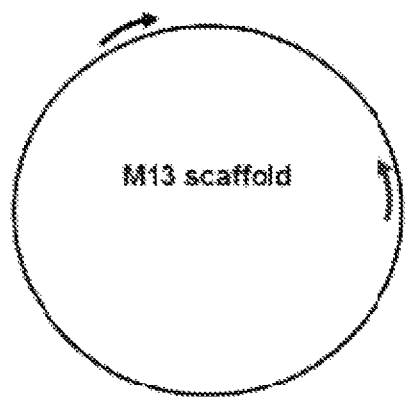
FIG. 6A  FIG. 6B
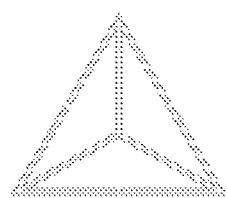 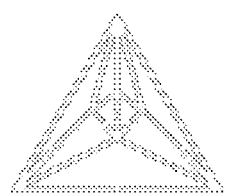 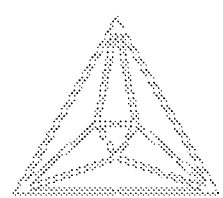 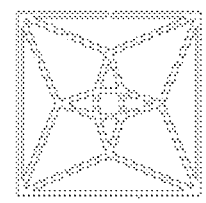
756 b     1560 b     1248 b     2496 b
FIG. 7A     FIG. 7B     FIG. 7C     FIG. 7D
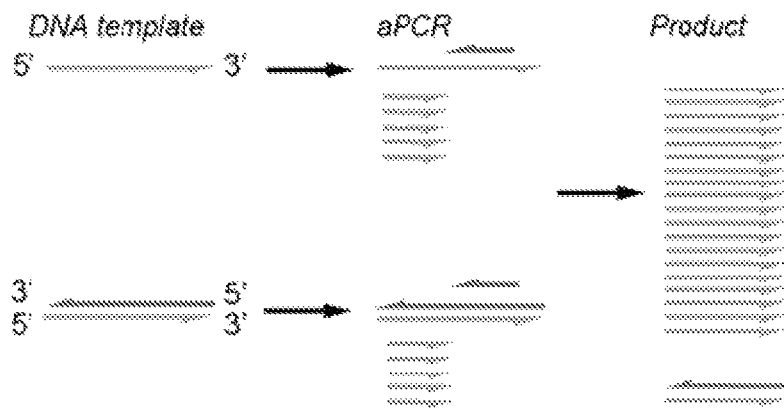
FIG. 7E

Full M13mp18     Short ssDNA scaffold
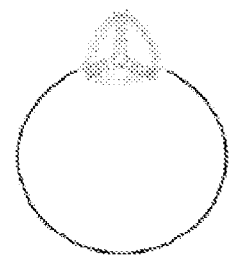 
FIG. 8A     FIG. 8B
Three-way junction   Four-way junction   Single cross-over   One nick
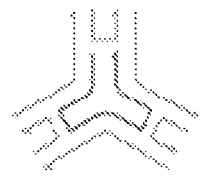 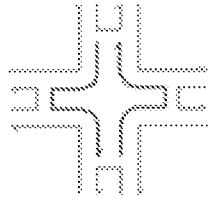 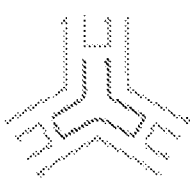 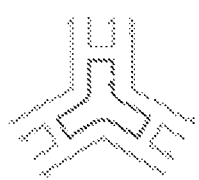
FIG. 9A    FIG. 9B    FIG. 9C    FIG. 9D
Five-way junction   Six-way junction   Two nick   Without poly-T
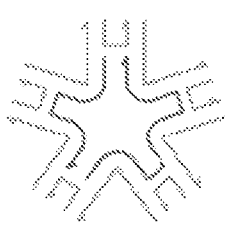 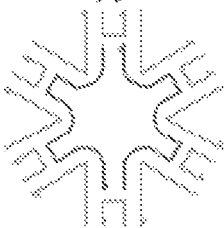 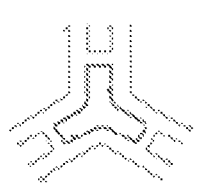 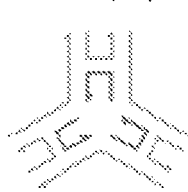
FIG. 9E    FIG. 9F    FIG. 9G    FIG. 9H

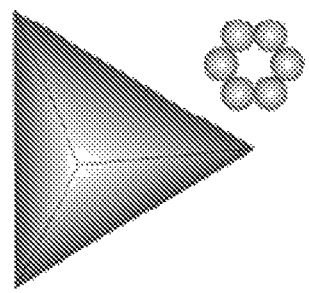
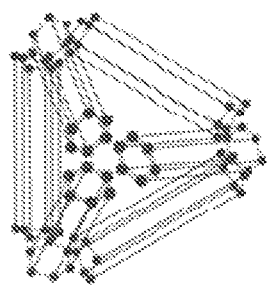
FIG. 14A     FIG. 14B
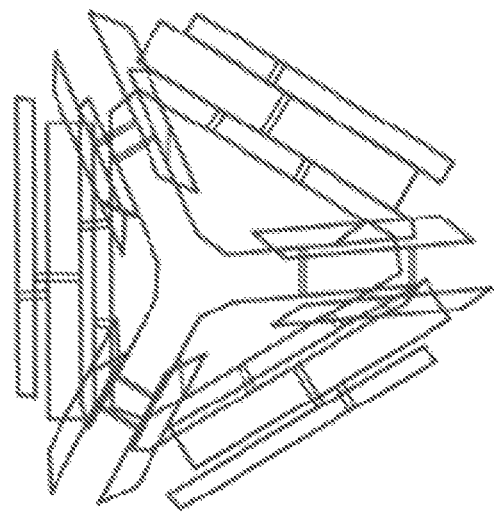
FIG. 14C
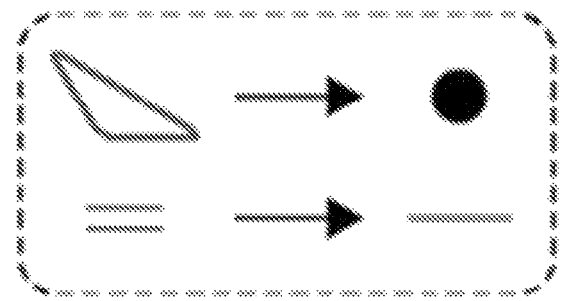
FIG. 14D

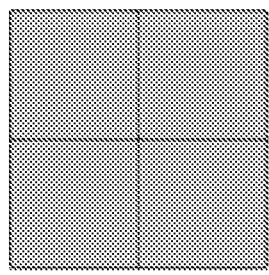
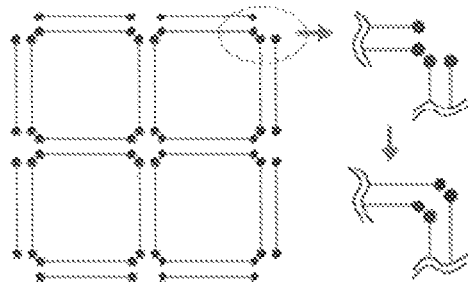
FIG. 15A  FIG. 15B  FIG. 15C
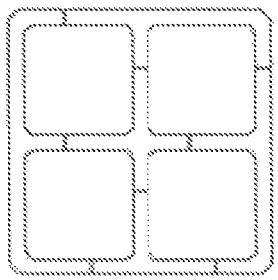
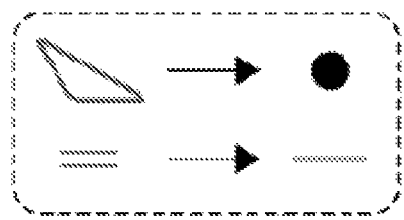
FIG. 15D  FIG. 15E
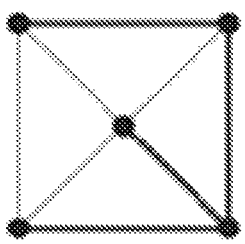
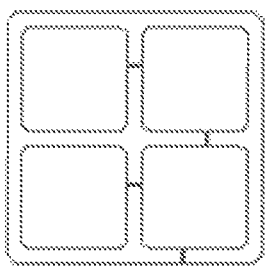
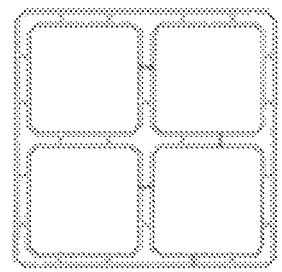
FIG. 15F  FIG. 15G  FIG. 15H
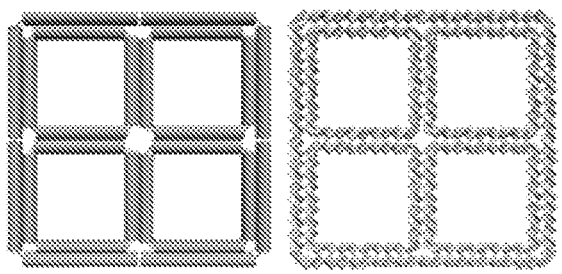
FIG. 15I  FIG. 15J

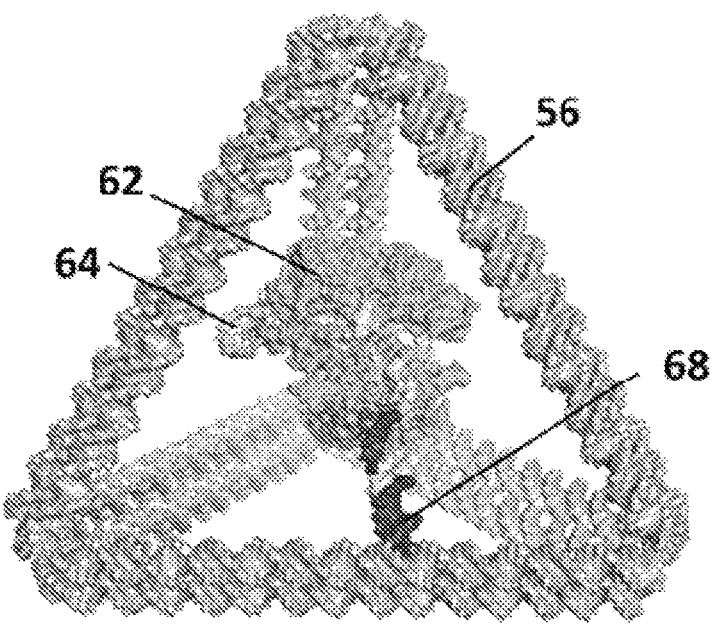
FIG. 16C
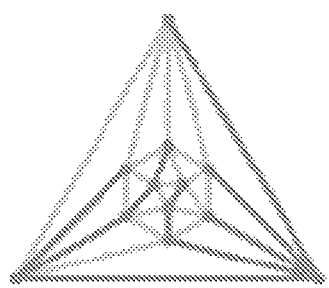
FIG. 17A
| PX spanning tree | PX non-spanning tree |
|---|---|
| DX spanning tree | DX non-spanning tree |
FIG. 17B
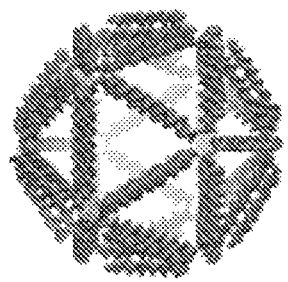
FIG. 17C
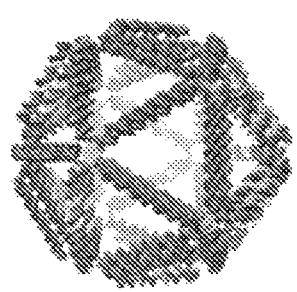
FIG. 17D

SEQUENCE LISTING

```
<160> NUMBER OF SEQ ID NOS: 37

<210> SEQ ID NO 1
<211> LENGTH: 19
<212> TYPE: DNA
<213> ORGANISM: Artificial Sequence
<220> FEATURE:
<223> OTHER INFORMATION: Synthetic Primer

<400> SEQUENCE: 1
gtcgtcgtcc cctcaaact                                                19

<210> SEQ ID NO 2
<211> LENGTH: 22
<212> TYPE: DNA
<213> ORGANISM: Artificial Sequence
<220> FEATURE:
<223> OTHER INFORMATION: Synthetic Primer
```

```
<400> SEQUENCE: 2
ggacgctatc cagtctaaac at                                              22

<210> SEQ ID NO 3
<211> LENGTH: 19
<212> TYPE: DNA
<213> ORGANISM: Artificial Sequence
<220> FEATURE:
<223> OTHER INFORMATION: Synthetic Primer

<400> SEQUENCE: 3
ctaccctcgt tccgatgct                                                  19

<210> SEQ ID NO 4
<211> LENGTH: 21
<212> TYPE: DNA
<213> ORGANISM: Artificial Sequence
<220> FEATURE:
<223> OTHER INFORMATION: Synthetic Primer

<400> SEQUENCE: 4
cgctttcttc ccttcctttc t                                               21

<210> SEQ ID NO 5
<211> LENGTH: 27
<212> TYPE: DNA
<213> ORGANISM: Artificial Sequence
<220> FEATURE:
<223> OTHER INFORMATION: Synthetic Primer

<400> SEQUENCE: 5
tggaaagcgc agtctctgaa tttaccg                                         27

<210> SEQ ID NO 6
<211> LENGTH: 20
<212> TYPE: DNA
<213> ORGANISM: Artificial Sequence
<220> FEATURE:
<223> OTHER INFORMATION: Synthetic Primer

<400> SEQUENCE: 6
gtctcgctgg tgaaaagaaa                                                 20

<210> SEQ ID NO 7
<211> LENGTH: 21
<212> TYPE: DNA
<213> ORGANISM: Artificial Sequence
<220> FEATURE:
<223> OTHER INFORMATION: Synthetic Primer

<400> SEQUENCE: 7
ctcggtggcc tcactgatta t                                               21

<210> SEQ ID NO 8
<211> LENGTH: 20
<212> TYPE: DNA
<213> ORGANISM: Artificial Sequence
<220> FEATURE:
<223> OTHER INFORMATION: Synthetic Primer

<400> SEQUENCE: 8
attaatgccg gagagggtag                                                 20
```

<210> SEQ ID NO 9
<211> LENGTH: 22
<212> TYPE: DNA
<213> ORGANISM: Artificial Sequence
<220> FEATURE:
<223> OTHER INFORMATION: Synthetic Primer

<400> SEQUENCE: 9
gaaagaggac agatgaacgg tg                                      22

<210> SEQ ID NO 10
<211> LENGTH: 20
<212> TYPE: DNA
<213> ORGANISM: Artificial Sequence
<220> FEATURE:
<223> OTHER INFORMATION: Synthetic Primer

<400> SEQUENCE: 10
gctgaaaagg tggcatcaat                                         20

<210> SEQ ID NO 11
<211> LENGTH: 20
<212> TYPE: DNA
<213> ORGANISM: Artificial Sequence
<220> FEATURE:
<223> OTHER INFORMATION: Synthetic Primer

<400> SEQUENCE: 11
gttaatgccc cctgcctatt                                         20

<210> SEQ ID NO 12
<211> LENGTH: 21
<212> TYPE: DNA
<213> ORGANISM: Artificial Sequence
<220> FEATURE:
<223> OTHER INFORMATION: Synthetic Primer

<400> SEQUENCE: 12
ggcgattaag ttgggtaacg c                                       21

<210> SEQ ID NO 13
<211> LENGTH: 23
<212> TYPE: DNA
<213> ORGANISM: Artificial Sequence
<220> FEATURE:
<223> OTHER INFORMATION: Synthetic Primer

<400> SEQUENCE: 13 gacttttca tgaggaagtt tcc                                      23

<210> SEQ ID NO 14
<211> LENGTH: 21
<212> TYPE: DNA
<213> ORGANISM: Artificial Sequence
<220> FEATURE:
<223> OTHER INFORMATION: Synthetic Primer

<400> SEQUENCE: 14
gctgcaaggc gattaagttg g                                       21

<210> SEQ ID NO 15
<211> LENGTH: 20
<212> TYPE: DNA
<213> ORGANISM: Artificial Sequence
<220> FEATURE:

<223> OTHER INFORMATION: Synthetic Primer

<400> SEQUENCE: 15
gtcgtcgtcc cctcaaactc                                           20

<210> SEQ ID NO 16
<211> LENGTH: 20
<212> TYPE: DNA
<213> ORGANISM: Artificial Sequence
<220> FEATURE:
<223> OTHER INFORMATION: Synthetic Primer

<400> SEQUENCE: 16
tgcctcaacc tcctgtcaat                                           20

<210> SEQ ID NO 17
<211> LENGTH: 21
<212> TYPE: DNA
<213> ORGANISM: Artificial Sequence
<220> FEATURE:
<223> OTHER INFORMATION: Synthetic Primer

<400> SEQUENCE: 17
gggcttgcta tccctgaaaa t                                         21

<210> SEQ ID NO 18
<211> LENGTH: 20
<212> TYPE: DNA
<213> ORGANISM: Artificial Sequence
<220> FEATURE:
<223> OTHER INFORMATION: Synthetic Primer

<400> SEQUENCE: 18
gcgacgattt acagaagcaa                                           20

<210> SEQ ID NO 19
<211> LENGTH: 27
<212> TYPE: DNA
<213> ORGANISM: Artificial Sequence
<220> FEATURE:
<223> OTHER INFORMATION: Synthetic Primer

<400> SEQUENCE: 19
tcgtcgctat taattaattt tccctta                                   27

<210> SEQ ID NO 20
<211> LENGTH: 22
<212> TYPE: DNA
<213> ORGANISM: Artificial Sequence
<220> FEATURE:
<223> OTHER INFORMATION: Synthetic Primer

<400> SEQUENCE: 20
gatgagtgcg gtacttggtt ta                                        22

<210> SEQ ID NO 21
<211> LENGTH: 21
<212> TYPE: DNA
<213> ORGANISM: Artificial Sequence
<220> FEATURE:
<223> OTHER INFORMATION: Synthetic Primer

<400> SEQUENCE: 21
cacggtcggt atttcaaacc a                                         21

```
<210> SEQ ID NO 22
<211> LENGTH: 22
<212> TYPE: DNA
<213> ORGANISM: Artificial Sequence
<220> FEATURE:
<223> OTHER INFORMATION: Synthetic Primer

<400> SEQUENCE: 22
gcactgaccc cgttaaaact ta                                                  22

<210> SEQ ID NO 23
<211> LENGTH: 20
<212> TYPE: DNA
<213> ORGANISM: Artificial Sequence
<220> FEATURE:
<223> OTHER INFORMATION: Synthetic Primer

<400> SEQUENCE: 23
tctttgcctt gcctgtatga                                                     20

<210> SEQ ID NO 24
<211> LENGTH: 20
<212> TYPE: DNA
<213> ORGANISM: Artificial Sequence
<220> FEATURE:
<223> OTHER INFORMATION: Synthetic Primer

<400> SEQUENCE: 24
agaggcattt tcgagccagt                                                     20

<210> SEQ ID NO 25
<211> LENGTH: 21
<212> TYPE: DNA
<213> ORGANISM: Artificial Sequence
<220> FEATURE:
<223> OTHER INFORMATION: Synthetic Primer

<400> SEQUENCE: 25
gacttgcggg aggttttgaa g                                                   21

<210> SEQ ID NO 26
<211> LENGTH: 20
<212> TYPE: DNA
<213> ORGANISM: Artificial Sequence
<220> FEATURE:
<223> OTHER INFORMATION: Synthetic Primer

<400> SEQUENCE: 26
aagggcgaaa aaccgtctat                                                     20

<210> SEQ ID NO 27
<211> LENGTH: 25
<212> TYPE: DNA
<213> ORGANISM: Artificial Sequence
<220> FEATURE:
<223> OTHER INFORMATION: Synthetic Primer

<400> SEQUENCE: 27
acgtggactc caacgtcaaa gggcg                                               25

<210> SEQ ID NO 28
<211> LENGTH: 22
<212> TYPE: DNA
<213> ORGANISM: Artificial Sequence
<220> FEATURE:
<223> OTHER INFORMATION: Synthetic Primer
```

<400> SEQUENCE: 28
gctttgacga gcacgtataa cg                                        22

<210> SEQ ID NO 29
<211> LENGTH: 27
<212> TYPE: DNA
<213> ORGANISM: Artificial Sequence
<220> FEATURE:
<223> OTHER INFORMATION: Synthetic Primer

<400> SEQUENCE: 29
cgacgacaat aaacaacatg ttcagct                                   27

<210> SEQ ID NO 30
<211> LENGTH: 21
<212> TYPE: DNA
<213> ORGANISM: Artificial Sequence
<220> FEATURE:
<223> OTHER INFORMATION: Synthetic Primer

<400> SEQUENCE: 30
cctcttcgct attacgccag c                                         21

<210> SEQ ID NO 31
<211> LENGTH: 22
<212> TYPE: DNA
<213> ORGANISM: Artificial Sequence
<220> FEATURE:
<223> OTHER INFORMATION: Synthetic Primer

<400> SEQUENCE: 31
cagattcacc agtcacacga cc                                        22

<210> SEQ ID NO 32
<211> LENGTH: 20
<212> TYPE: DNA
<213> ORGANISM: Artificial Sequence
<220> FEATURE:
<223> OTHER INFORMATION: Synthetic Primer

<400> SEQUENCE: 32
gctaacgagc gtcttttccag                                          20

<210> SEQ ID NO 33
<211> LENGTH: 22
<212> TYPE: DNA
<213> ORGANISM: Artificial Sequence
<220> FEATURE:
<223> OTHER INFORMATION: Synthetic Primer

<400> SEQUENCE: 33
cagtgcagtg cttgataaca gg                                        22

<210> SEQ ID NO 34
<211> LENGTH: 20
<212> TYPE: DNA
<213> ORGANISM: Artificial Sequence
<220> FEATURE:
<223> OTHER INFORMATION: Synthetic Primer

<400> SEQUENCE: 34
gtagtgcgcg tttgatttcc                                           20

<210> SEQ ID NO 35
<211> LENGTH: 20

```
<212> TYPE: DNA
<213> ORGANISM: Artificial Sequence
<220> FEATURE:
<223> OTHER INFORMATION: Synthetic Primer

<400> SEQUENCE: 35
ccgaagtcga aatcaagctg                                               20

<210> SEQ ID NO 36
<211> LENGTH: 23
<212> TYPE: DNA
<213> ORGANISM: Artificial Sequence
<220> FEATURE:
<223> OTHER INFORMATION: Synthetic Primer

<400> SEQUENCE: 36
cctggtcgag ctggacggcg acg                                           23

<210> SEQ ID NO 37
<211> LENGTH: 23
<212> TYPE: DNA
<213> ORGANISM: Artificial Sequence
<220> FEATURE:
<223> OTHER INFORMATION: Synthetic Primer

<400> SEQUENCE: 37
ctgagcaccc agtccgccct gag                                           23
```

STABLE NANOSCALE NUCLEIC ACID ASSEMBLIES AND METHODS THEREOF

CROSS-REFERENCE TO RELATED APPLICATIONS

This application is a National Phase application under 35 U.S.C. § 371 of PCT/US2017/029891, filed Apr. 27, 2017, entitled "STABLE NANOSCALE NUCLEIC ACID ASSEMBLIES AND METHODS THEREOF," which claims the benefit of and priority to U.S. Provisional Application No. 62/328,442 filed Apr. 27, 2016 and U.S. Provisional Application No. 62/328,450 filed Apr. 27, 2016, the contents of which are hereby incorporated by reference in their entirety.

STATEMENT REGARDING FEDERALLY SPONSORED RESEARCH

This invention was made with government support under Grant Nos. N00014-14-1-0609 and N00014-16-1-2181 awarded by the Office of Naval Research, under Grant No. CMMI-1334109 awarded by the National Science Foundation, under Grant No. RGP0029/2015 awarded by the Human Frontier Science Program (HFSP), and under Grant No. CCF-1547999 awarded by the National Science Foundation (NSF-EAGER). The government has certain rights in the invention.

REFERENCE TO SEQUENCE LISTING

The Sequence Listing submitted Apr. 27, 2017, as a text file named "MIT_18588_PCT_ST25.txt," created on Apr. 27, 2017, and having a size of 7,408 bytes is hereby incorporated by reference pursuant to 37 C.F.R. § 1.52(e)(5).

FIELD OF THE INVENTION

The present invention relates to the design of arbitrary 2D or 3D geometries using nucleic acids, and in particular to the design of nucleic acid nanostructures having a desired geometric form in order to mimic and/or reproduce existing natural macromolecular assemblies, as well as synthesize entirely new ones.

BACKGROUND OF THE INVENTION

DNA nanotechnology offers the unique ability to synthesize highly structured nanometer-scale assemblies that in principle could rival the geometric complexity found in natural protein and nucleic acid assemblies. The past decade has witnessed dramatic growth in the diversity of structured DNA assemblies that can be programmed from the bottom-up to self-assemble into target shapes using complementary Watson-Crick base pairing (Seeman, N C et al., *Biophys. J.* 44, 201-209 (1983); Rothemund, P W K, *Nature,* 440, 297-302 (2006); Rothemund, P W, *Nanotechnology: Science and Computation,* 3-21 (2006); He, Y et al., *Nature.* 452, 198-201 (2008); Jones, M R et al., *Science.* 347, 1260901 (2015); Zhang, F et al., *Nat. Nanotechnol.* 10, 779-784 (2015)). Scaffolded DNA origami is a particularly powerful means of synthesizing structured DNA assemblies, offering full control over both molecular weight and intricate nanometer-scale structure, with quantitative yield of the programmed product that relies on a single-stranded DNA template (Rothemund, P W K, *Nature.* 440, 297-302 (2006); Zhang, F et al., *Nat. Nanotechnol.* 10, 779-784 (2015); Dunn, K E et al., *Nature.* 525, 82-86 (2015); Shih, W M et al., *Nature.* 427, 618-621 (2004); Martin, T G et al., *Nat. Commun.* 3, 1103 (2012); Han, D et al., *Science.* 332, 342-346 (2011); Ko, et al., *Nature Chemistry,* 2, pp. 1050-1055, (2010); Han, D et al., *Science.* 339, 1412-1415 (2013); Castro, C E et al., *Nat. Methods.* 8, 221-229 (2011)). Wireframe topologies based on the scaffolding principle have further demonstrated highly versatile control over 2D and 3D spatial architecture (Zhang, F et al., *Nat. Nanotechnol.* 10, 779-784 (2015); Yan, H et al., *Science.* 301, 1882-1884 (2003); Yan, H et al., *Science.* 301, 1882-1884 (2003); Seeman, et al., *Nano Lett.,* V1, (1) 22-26 (2001); Spink, et al., *Biophysical Journal,* V 97, 528-538 (2009); Wang, *PNAS,* 9. 107 (28), pp. 12547-12552 (2010); Gu, et al., *Nature Nanotechnology,* 4, 245-248 (2009)).

Similar to the challenge of structure-based protein sequence design, which seeks to infer the amino acid sequence needed to fold a target protein structure of interest (Sinclair, J C et al., *Nat. Nanotechnol.* 6, 558-562 (2011); Gradišar, H et al., *Nat. Chem. Biol.* 9, 362-366 (2013)), achieving a general strategy for structure-based design of DNA assemblies represents a major challenge as well as opportunity for nanotechnology. While numerous computational design tools exist to aid in the bottom-up, manual programming of scaffolded DNA origami, which requires complex scaffold routing and staple design to realize a target geometry based on Watson-Crick base complementarity, only one approach offers a solution to the inverse problem of sequence design based on specification of target geometry (Benson, E, et al., *Nature.* 523, 441-444 (2015)). However, this approach is only semi-automated and relies on single duplex DNA arms and multi-junctions to represent polyhedral geometries, which may result in compliant and unstable assemblies that are unsuitable for many applications. Moreover, programmed geometries must be topologically equivalent to a sphere, significantly limiting its scope.

Therefore, it is an object of the invention to provide a method to identify combinations of nucleic acid sequences and oligonucleotide primers that can be combined to produce nanoscale assemblies of nucleic acids including DNA or RNA or DNA/RNA hybrid assemblies.

It is also an object of the invention to provide methods to identify combinations of nucleic acid sequences without oligonucleotide primers that alone can produce nanoscale DNA or RNA assemblies.

It is also an object of the invention to provide fully automated inverse sequence design of nanoscale DNA or RNA or DNA/RNA hybrid assemblies.

It is also an object of the invention to provide arbitrary wireframe DNA assemblies without any limitation to spherical topologies.

It is also an object of the invention to provide arbitrary wireframe DNA assemblies with any even number of DNA or RNA or DNA/RNA hybrid helices per edge, or the geometry of the edge.

It is a further object of the invention to provide structurally stable, rigid nanoscale DNA or RNA or DNA/RNA hybrid assemblies.

It is a further object of the invention to provide methods of designing rigid 3D nucleic acid scaffolds that can be used to pattern in 3D space arbitrary organizations of secondary molecules that either bind directly to the nucleic acid sequence, or are covalently or non-covalently attached to nucleic acid bases or sugars, such as proteins, peptides, aptamers, lipids, sugars, RNAs, PNAs, etc., based on top-down specification of 3D nanoparticle shape and size.

It is also an object of the invention to provide a method to generate single-stranded DNA of arbitrary length, sequence, and modified composition that can assemble into a 3D structure having a desired shape and size.

SUMMARY OF THE INVENTION

Methods for the automated design of nucleic acid nanostructure having arbitrary geometries and scaffold sequences have been developed. The methods generate single-stranded nucleic acid sequences of arbitrary length, with or without chemical modifications, and define rules for sequence space that optimizes product yield. An exemplary nucleic acid scaffold sequence is single-stranded DNA.

In some embodiments, methods for designing a nucleic acid nanostructure having a geometric shape include the steps of determining the geometric parameters of an input and identifying a route for a single-stranded nucleic acid scaffold that traces throughout the geometric shape, then generating the sequences of the single-stranded nucleic acid scaffold and optionally the nucleic acid sequence of staple strands that combine to form a nucleic acid nanostructure having the geometric shape.

The methods enable the top-down design of nanostructures formed from nucleic acids, based on the geometry of a desired target shape. Typically, the methods provide the nucleic acid sequences required to form a three-dimensional structure corresponding to a desired geometric form. The methods require only the geometric parameters that define the desired structure as input, and enable the user to optionally define additional parameters, such as the physical size and nucleic acid polymer scaffold sequence. The methods can be computer-based. In some embodiments, output is in the form of a single-stranded nucleic acid polymer that is a scaffold sequence routed throughout every edge of the nanostructure, and one or more oligonucleotide staple sequences that hybridize to the scaffold sequence to provide a double-stranded nucleic acid structure having the desired form with the desired edge type composed of an even number of DNA or RNA helices. In some embodiments, output is in the form of a single-stranded nucleic acid polymer that is a scaffold sequence that is routed several times throughout every edge of the nanostructure providing a double-stranded nucleic acid structure of the desired form without the need for staples, or as few staples as desired, by allowing self-hybridization.

Methods of assembling and purifying nucleic acid nanoparticles are also provided. In some embodiments, the methods include one or more steps to alter the chemical or structural properties of the nucleic acid nanoparticles. Therefore, methods of functionalizing nucleic acid nanoparticles are provided. In some embodiments, methods of functionalizing nucleic acid nanoparticles include one or more steps that alter the chemical or structural properties of the assembled nucleic acid nanoparticles. In some embodiments, the methods of functionalizing nucleic acid nanoparticles include one or more steps that alter the chemical or structural properties of the nucleic acid scaffold prior to assembly of the nucleic acid nanoparticles. In some embodiments, the methods of functionalizing nucleic acid nanoparticles include one or more steps that alter the chemical or structural properties of the nanoparticles through chemical or structural modifications of oligonucleotide staple strands. In an exemplary embodiment, the methods of functionalizing nucleic acid nanoparticles include extension of the oligonucleotide staple strands to produce single-stranded DNA emanating at precise locations on the structure. Therefore, nanostructures can be designed and assembled to mimic biological structures such as virus capsids, toxins, protein assemblies, lipid and sugar organizations, and can be used for applications such as delivery, immune stimulation for vaccines, complexing with proteins or RNA, and sensing.

Typically, the methods include the steps of (a) selecting a desired 2D or 3D form as a target structure; (b) providing geometric parameters and physical dimensions of the target structure; (c) identifying the route of a single-stranded nucleic acid scaffold that traces throughout the entire target structure; and (d) determining the sequences of the single-stranded nucleic acid scaffold and the nucleic acid sequence of staple strands that combine to form a nucleic acid nanostructure having the desired shape. In some embodiments, the target structure is a structure that does not have spherical topology.

The step of providing the geometric parameters and physical dimensions of the target polyhedral structure further can include providing a template nucleic acid scaffold sequence. For example, in some embodiments, the methods include providing the length of one or more of the edges spanning two vertices of the target polyhedral structure. Preferably, the length of each edge is at least 31 base pairs.

In some embodiments, DNA is used as a scaffold. When DNA is a scaffold, the length of each edge can be expressed as a multiple of 10.5 base pairs, rounded up, or rounded down to the nearest whole number. In an exemplary embodiment, the length of each edge is 31 base pairs, 32 base pairs, 42 base pairs, 52 base pairs, 53 base pairs, 63 base pairs, 73 base pairs, or more than 73 base pairs. In other embodiments, RNA is used as a scaffold. When RNA is used as a scaffold, the length of each edge can be expressed as a multiple of 11 base pairs. In an exemplary embodiment, the length of each edge is 33 base pairs, 44 base pairs, 55 base pairs, 66 base pairs, 77 base pairs, or more than 77 base pairs.

Typically, the geometric parameters provided as input include vertex, face, and edge information, for example, as determined from a polyhedral wire-mesh model of the target shape.

The route of a single-stranded nucleic acid scaffold that traces throughout the entire target structure is typically identified by a method including: (i) producing a node-edge network representing the three-dimensional structure; (ii) determining a spanning tree of the network corresponding to the three-dimensional structure, for example, where the vertices and lines of the structure are the nodes and edges of the network, respectively; (iii) classifying each edge as having a double stranded scaffold crossover, if it is not a member of the spanning tree, or not having one if it is a member of the spanning tree; (iv) splitting the edges that are not members of the spanning tree into two edges, each containing a pseudo-node at the point of the scaffold crossover and each node at each of the vertices being split into two pseudo-nodes; and (v) determining the route of a single-stranded nucleic acid scaffold that traces once along each edge in both directions throughout the entire target structure from a Euler cycle of the network. In some embodiments, the planar representation of the graph of the three-dimensional structure for aiding visualization is the Schlegel diagram of the three-dimensional structure. In preferred embodiments, the spanning tree of the network is a branched spanning tree, such as a breadth-first spanning tree. In a particular embodiment, the spanning tree is determined using Prim's formula. Typically, the Euler circuit calculated from the spanning tree is an A-trail Euler circuit.

In some embodiments, DNA is used as a scaffold and the length of each edge is expressed as a multiple of 10.5 base pairs, rounded up, or rounded down to the nearest whole number. Further, the cross-section of the edge is chosen to be composed of 2 helices per edge, 4 helices per edge, 6 helices per edge, 8 helices per edge, 10 helices per edge, or greater than 10 helices per edge. In an exemplary embodiment, the length of each edge is 31 base pairs, 42 base pairs, 52 base pairs, 63 base pairs, 73 base pairs, 84 base pairs, or more than 84 base pairs with 4 helices bundled in parallel on a square lattice, 6 helices bundled in parallel on a honeycomb lattice, 6 helices bundled in parallel on a square lattice, 10 helices bundled in parallel on a honeycomb lattice, or more than 6 or 10 helices in parallel along a square or honeycomb lattice.

In some embodiments, DNA is used as a scaffold and the length of each edge is expressed as an integer number of nucleotides. The edge type can be of 2 helices, 4 helices, 6 helices, or more than 6 helices arranged in parallel along a square lattice, or a honeycomb lattice. These edges can be arranged in a closed or open wireframe structure in 3D or in a 2D wireframe grid, having a planar, spherical, or non-spherical topology. The intersection of the edges at a vertex can be extended in length by the amount necessary to bring the helices precisely together, similar to a beveled edge in woodworking. The additional distance from the helices coming together are spanned by the number of double-helical nucleotides.

In some embodiments, DNA is used as a scaffold that is traced more than two times crossing the vertex, which depends on the number of helixes on the edge. For example, in the case of the 3-arm junction, the three edges are connected to each other by three single strands with DNA traced two times through each vertex, and with nine single strands with this approach.

In some embodiments, DNA is used as a scaffold that is traced more than once along the edges of the structure and eliminates the necessity for some or all oligonucleotides to fold.

The route of a single-stranded nucleic acid scaffold that traces throughout the entire target structure and can hybridize to itself is typically identified by a method including: (i) producing a node-edge network representing the three-dimensional structure; (ii) determining a spanning tree of the network corresponding to the three-dimensional structure, for example, where the vertices and lines of the structure are the nodes and edges of the network, respectively; (iii) classifying each edge as one of four types, based on its membership in the spanning tree and the crossover motif employed: if it is not a member of the spanning tree, each fragment of the scaffold exits the edge from the vertex it starts from, if it is a member of the spanning tree, each fragment of the scaffold exits the edge from the vertex it did not start from, and each edge can employ either anti-parallel or parallel crossover motifs; (iv) splitting the edges that are not members of the spanning tree into two edges, each containing a pseudo-node at the point of the scaffold crossover and each node at each of the vertices being split into two pseudo-nodes; and (v) determining the route of a single-stranded nucleic acid scaffold that traces throughout the entire target structure from the Eulerian cycle of the network by superimposing and connecting units of partial scaffold routing within an edge based on its classification and length.

In some embodiments, the methods include the step of predicting the three-dimensional structure of the nucleic acid nanostructure. In some embodiments, the methods include the step of making the nucleic acid nanostructure. Therefore, in certain embodiments, the methods include the steps of predicting the three-dimensional structure and making the nucleic acid nanostructure. When the methods include predicting the three-dimensional structure and making the nucleic acid nanostructure, the methods optionally include the step of validating the nucleic acid nanostructure. For example, in some embodiments the nucleic acid nanostructure is validated by comparison with the predicted three-dimensional structure.

In some embodiments, asymmetric polymerase chain reaction (aPCR) is used to synthesize long single-stranded DNA used as a scaffold. Typically, an aPCR reaction is composed of two primers flanking the region of interest to be amplified, a template DNA to replicate from, buffers, nucleotides, and polymerase enzymes, where one of the primers is in excess over the other. In some embodiments, one primer is in 50- or 65-fold molar excess over the second primer. In some embodiments, the length of the scaffold is 500 nucleotides in length; 1000 nucleotides in length; 1500 nucleotides in length; 2000 nucleotides in length; 2500 nucleotides in length; 3281 nucleotides in length; 10,000 nucleotides in length; 12,000 nucleotides in length; or greater than 12,000 nucleotides. Typically, Taq-based polymerases or commercial blend of enzymes [LONGAMP®] are used as the enzyme in aPCR. In some embodiments, the nucleic acid polymer can be modified by introduction of modified nucleotides into the solution, including fluorescent nucleotides, radio-labeled nucleotides, alternative bases, and modified backbone. In an exemplary embodiment, alternative nucleotides are used in the DNA polymer synthesis with nucleotides modified with Cy5 fluorophore-modified nucleotides, phosphorothioate-modified nucleotides, and deoxyuridines. In another exemplary embodiment, modified primers including additional 5' sequences to add to the amplicons is used to increase or modify the ssDNA final product or to hybridize to other ssDNA produced by standard synthesis or through aPCR. In another exemplary embodiment, the primers can be phosphorylated for ligation.

Compositions of polyhedral nucleic acid nanostructures designed according to the described methods are also provided. In one embodiment, the polyhedral nucleic acid nanostructures include two nucleic acid anti-parallel helices spanning each edge of the structure. In another embodiment, the polyhedral nucleic acid nanostructures include 4, 6, 8, or more than 8 anti-parallel helices spanning each edge of the structure. The three-dimensional structure is formed from single stranded nucleic acid staple sequences hybridized to a single stranded nucleic acid scaffold sequence. The scaffold sequence is routed through a Eulerian cycle of the network defined by the vertices and lines of the polyhedral structure. The locations of double-stranded crossovers are determined by the spanning tree of the polyhedral structure. The staple sequences are hybridized to the vertices, edges and double-stranded crossovers of the scaffold sequence to define the shape of the nanostructure. In some embodiments, the polyhedral nucleic acid nanostructures include 2 or more than 2 parallel helices spanning each edge of the structure. The three-dimensional structure is formed from single stranded nucleic acid sequences hybridized to itself. The scaffold sequence is routed through the Eulerian cycle of the network defined by the vertices and edges of the polyhedral structure. In other embodiments, the polyhedral nucleic acid nanostructures include a combination of 2 or more than 2 parallel or anti-parallel helices spanning each edge of the structure. In some embodiments, the polyhedral nucleic acid nanostructure further includes one or more of a therapeutic, diagnostic or prophylactic agent, or combinations. For example, in some embodiments the nanostructures encapsulates one or more therapeutic, diagnostic or prophylactic agent. In other embodiments secondary molecules are either covalently or non-covalently attached to the DNA structural scaffold or oligonucleotides with resulting full control over their 3D organization. In an exemplary embodiment messenger RNA (mRNA) encoding a protein is non-covalently attached to the DNA nanostructure using single-stranded DNA extensions from the oligonucleotides and complementary to the mRNA. In another exemplary embodiment, the gene editing protein Cpf1 is attached to the DNA nanostructure using double-stranded DNA duplex attached to oligonucleotides and passing through the structure. In another exemplary embodiment, the gene editing protein Cpf1 is attached to the DNA nanostructure using single-stranded DNA extensions from the oligonucleotides and complementary to 3' extensions of a crRNA loaded to Cpf1. This approach can be generalized to include alternative gene editing proteins and DNA-interacting proteins including Cas9, tal effectors, and zinc fingers.

Methods of using the polyhedral nucleic acid nanostructures for the delivery of a therapeutic, diagnostic or prophylactic agent to a subject, or using nucleic acid nanostructures as platforms for synthetic vaccines are also provided.

BRIEF DESCRIPTION OF THE DRAWINGS

FIG. 2B is also used in subsequent figures. The polyhedral shapes include Platonic (1-5), Archimedean (6-15), Johnson (16-25), Catalan (26-35), and other polyhedra (36-45), generated using the top-down design procedure. Miscellaneous polyhedra include (first column) heptagonal bipyramid (36); enneagonal trapezohedron (37); small stellated dodecahedron (38), a type of Kepler-Poinsot solid; rhombic hexecontahedron (39), a type of zonohedron; Goldberg polyhedron with symmetry of Papillomaviridae (40); (second column) double helix (41); nested cube (42); nested octahedron (43); torus (44); and double torus (45). Single-stranded poly-T loops are omitted. Platonic, Archimedean, and Johnson solids each have 52-bp edge length, Catalan solids and the first column of other polyhedra have minimum 42-bp edge length, and the second column of other polyhedra have minimum 31-bp edge length. Objects are not drawn to scale.

The same numbering scheme used in FIG. 2A and FIG. 2B is also used in FIGS. 4A-4H and FIG. 13.

FIGS. 3A-3N are schematic illustrations, each showing a step in the top-down sequence design strategy for a tetrahedron (shape number 1 in FIG. 2A). FIG. 3A is an input tetrahedral shape shown as a mesh having vertices, edges, and faces. FIG. 3B is a 2D projection of FIG. 3A, that is a Schlegel diagram. FIGS. 3C and 3D each show one of two spanning trees which will lead to a valid scaffold routing. The default is to generate the most-branching tree (FIG. 3C), and an alternative tree is also given (FIG. 3D). FIGS. 3E and 3F show the spanning trees of FIGS. 3C and 3D, respectively, with the edges that are not members of the spanning tree broken in two to define the scaffold crossovers. FIGS. 3G and 3H show the vertices of FIGS. 3E and 3F split according to each spanning tree. FIGS. 3I and 3J show the scaffold routes of each spanning tree of FIGS. 3G and 3H. FIGS. 3K and 3L show define the Eulerian circuit of each of two possible routes of FIGS. 3C and 3D. FIG. 3M is a schematic illustrating an example of how scaffold crossover positions are determined for a given edge length in basepairs (bp). FIG. 3N is an enlarged view of FIG. 3K, showing vertex staples (48) and edge staples (50), scaffold nick position (52) and scaffold polarity (arrow 54).

FIGS. 4A-4D depict DNA nanostructures with non-spherical topologies shown as face-shaded models. FIGS. 4E-4H depict predicted computational models of atomic structures for the corresponding scaffolded DNA origami objects, respectively. The objects are nested cube (42) (FIG. 4A, FIG. 4E); nested octahedron (43) (FIG. 4B, FIG. 4F); torus (44) (FIG. 4C, FIG. 4G); and double torus (45) (FIG. 4D, FIG. 4H).

FIGS. 5A-5F show each of six different vertices for predicting 3D structures, for each of three four-way junctions (FIGS. 5A-5C), and three three-way junctions (FIGS. 5D-5F), respectively. The inradius of each vertex is depicted as a circle. The beginning of the DX-tile edge is shown as a rectangle, the edges represented by dotted lines, which meet at a single point. FIG. 5A and FIG. 5D show vertices with equal face angles. FIG. 5B and FIG. 5E show vertices with unequal face angles defined using backbone stretches. FIG. 5C and FIG. 5F show vertices with unequal face angles defined using nucleotide overlap.

FIGS. 6A and 6B are schematics illustrating methods used to produce short ssDNA scaffold strands from M13mp18 ssDNA plasmid, by enzymatic digestion (FIG. 6A), and aPCR amplification (FIG. 6B).

FIGS. 7A-7D depict the custom scaffold sequence routes determined by each of four different Eulerian circuits corresponding to four different polyhedral structures (FIGS. 7A-7D), respectively. The size of each nucleic acid scaffold in bases (b) is shown beneath each depiction.

FIG. 7E is a schematic diagram of object-specific scaffold synthesis using asymmetric PCR. The length for the target structure is identified for amplification using either single- or double-stranded DNA (DNA template) mixed with appropriate (aPCR) primer pairs, with 50× sense primer and 1× anti-sense primer concentration relative to scaffold.

FIGS. 8A-8B are schematics depicting the folding of a tetrahedron using a full M13mp18 scaffold (FIG. 8A) or a short ssDNA scaffold (FIG. 8B), respectively.

FIGS. 9A-9H are schematic representations of different possible vertex staple designs, as characterized on a tetrahedral nucleic acid nanostructure having an isolated vertex, with edge-length of 52-bp. Proposed vertex staples designs with a single cross-over are depicted for each of a 3-way junction (FIGS. 9A, 9E), 4-way junction (FIG. 9B), 5-way junction (FIG. 9C), and 6-way junction (FIG. 9D). FIGS. 9E-9H depict four different types of vertex staple design for a 3-way junction; vertex staples designs are depicted for each of single cross-over (FIG. 9E), one nick (FIG. 9F) two-nick (FIG. 9G) and without poly-T (FIG. 9H) staple designs, respectively.

FIG. 9I shows fluorescence intensity (a.u.) over temperature (° C.) for each of four different vertex staple designs on isolated DX tiles, including single cross-over model (sx); one nick model (N1); two-nick model (N2); and without poly-T model (WOT); designs, respectively. FIG. 9J shows Df/Dt over temperature (° C.) of data in 9I for each vertex staple design, including single cross-over model (sx); one nick model (N1); two-nick model (N2); and without poly-T model (WOT); designs, respectively. FIG. 9K shows fluorescence intensity (a.u.) over temperature (° c.) for each of three different vertex staple designs on a tetrahedral structure with edge-length of 52-bp, including single cross-over model (sx); two-nick model (N2); and without poly-T model (WOT); designs, respectively. FIG. 9L shows Df/Dt over temperature (° C.) for each vertex staple design, including single cross-over model (sx); two-nick model (N2); and without poly-T model (WOT); designs, respectively.

FIG. 10A is a schematic depicting folding of synthesized DX-based objects in increasing magnesium chloride ($MgCl_2$) and sodium chloride (NaCl) concentration. FIG. 10B is a schematic depicting characterization of the stability of synthesized DX-based objects in TAE-Mg (12 mM $MgCl_2$) buffer after exchange buffer and 6 hours in PBS, TAE (without added NaCl or $MgCl_2$), or DMEM buffer with increasing concentration of FBS (0, 2, and 10%).

FIG. 12A depicts a 4-arm junction, having each of four edges denoted by from 'a' to 'd' are connected at the vertex, i. FIG. 12B depicts the minimum angle, $\theta^i_{min}$ at the i-th vertex and the initial off-set distance (apothem), $r_i$ calculated by $\theta^i_{min}$ and the number of arms in i-th vertex. FIG. 12C depicts two cylinders (in case of the DX tile design) drawn on each edge with initial off-set distance, $r_i$. FIG. 12D depicts two cylinders located in adjacent edges that do not contact each other. The new off-set distance is $d^i_{a,b}$, in which the subscript a,d represents the edge identifier. The new off-set distance, $d^i_{a,b}$ can be solved with two given distance, $m^i_{a,b}$ and $n^i_{a,b}$ and the given angle $\theta^i_{a,b}$. FIG. 12E depicts the size-modified edges incorporating the off-set distance calculated in FIG. 12D.

FIGS. 14A-14I are schematic representations outlining each of the nine steps for top-down sequence design procedure for scaffolded DNA origami nanoparticles composed of an exemplary six-helix bundle polyhedron with honeycomb (non-beveled) cross-sectional morphology. Specification of the arbitrary target geometry (pyramid) is based on a continuous and closed surface that is discretized using a polyhedral mesh (FIG. 14A). This discretized geometry is modified to represent each of the six-helices at each edge as lines (FIG. 14B). The endpoints of the lines defined in FIG. 14B are joined such that every duplex become part of a loop (□) that has possible scaffold crossovers (∥) between these closed loops (FIG. 14C). The dual graph of the loop-crossover structures is introduced by converting each loop (□) to a node (●), and each double crossover (∥) to an edge (–), respectively (FIG. 14D). The spanning tree of the dual graph is computed (FIG. 14E). The route of the single-stranded DNA scaffold throughout the entire origami object is produced by inverting the spanning tree of the dual graph (FIG. 14F). Complementary staple strands are assigned based on the scaffold route (FIG. 14G). A 3D cylindrical model (FIG. 14H) and atomic-level structure (FIG. 14I) are generated assuming canonical B-form DNA geometry.

FIGS. 15A-15I are schematic representations outlining each of the nine steps for top-down sequence design procedure for scaffolded DNA of arbitrary target geometry based on an open surface that is discretized using a polygon mesh. An exemplary structure is shown in FIG. 15A. This discretized geometry is modified to represent two duplexes as two lines (FIG. 15B). The edge length is increased to be closed at the boundary (FIG. 15C). The endpoints of the lines defined in FIG. 15C are joined such that every duplex become part of a loop (□) that has possible scaffold crossovers (∥) between these closed loops (FIG. 15D). The dual graph of the loop-crossover structures is introduced by converting each loop (□) to a node (●), and each double crossover (∥) to an edge (–), respectively (FIG. 15E). The spanning tree of the dual graph is computed (FIG. 15F). The route of the single-stranded DNA scaffold throughout the entire origami object is produced by inverting the spanning tree of the dual graph (FIG. 15G). Complementary staple strands are assigned based on the scaffold route (FIG. 15H). A 3D cylindrical model (FIG. 15I) and atomic-level structure (FIG. 15J) are generated assuming canonical B-form DNA geometry.

FIGS. 16A-16C are atomic-level structural models of polyhedral nucleic acid nanostructures demonstrating schemes for using nucleic acid nanostructures for the capture of other molecules. FIG. 16A shows an open wireframe tetrahedron nanostructure (56) coupled to an mRNA (58) using single strand DNA overhangs extended from the staples at nick positions (60), with the sequence of the overhang complementary to predicted loops in the RNA structure. FIG. 16B depicts CRISPR enzyme Cpf1 (62) with crRNA (64) can be captured onto a DNA nanoparticles (56) on a crossbeam built into the nanoparticle (66), which contains a sequence targeted by the Cpf1/crisprRNA enzyme. FIG. 16C depicts CRISPR enzyme Cpf1 (62) with crRNA (64) can be captured onto a DNA nanoparticles (56) on an overhang sequences built into the nanoparticle (68), which contains a sequence complementary to a 3' extension of the crRNA.

FIGS. 17A-17E are schematic representations outlining each of the steps for top-down sequence design procedure for scaffolded DNA nanoparticles including parallel crossover (PX) motifs. FIG. 17A depicts the spanning tree obtained for the geometry of the desired polyhedral shape. FIG. 17B is a chart depicting edges classified into one of four categories, based on the crossover motif (PX vs. DX) and its membership in the spanning tree. Edge fragments are superimposed and connected according to the classification and the route of the scaffold through the structure. FIG. 17C depicts the atomic structure predicted in the case where only PX motifs are used, and no staples are present. FIG. 17D depicts the atomic structure predicted in the case where both PX and DX motifs are used, and staples are also added with Watson-Crick base pairing to the scaffold. FIG. 17E depicts the atomic structure model of a pure PX origami structure of another geometry, which has no staples; the object is a single nucleic acid strand routed through every duplex and hybridized to itself.

FIG. 18 is a schematic illustration showing diversity of nanostructure library design. Diversity is introduced at any level from object geometry, edge length between vertices, staple nick position or orientation along each edge, bait sequence orientation on the object, and the set of bait sequences that are used to capture the RNAs, which may be either guide RNAs, messenger RNAs, or alternatively genes employed for gene therapies.

DETAILED DESCRIPTION OF THE INVENTION

I. Definitions

Figure 1:
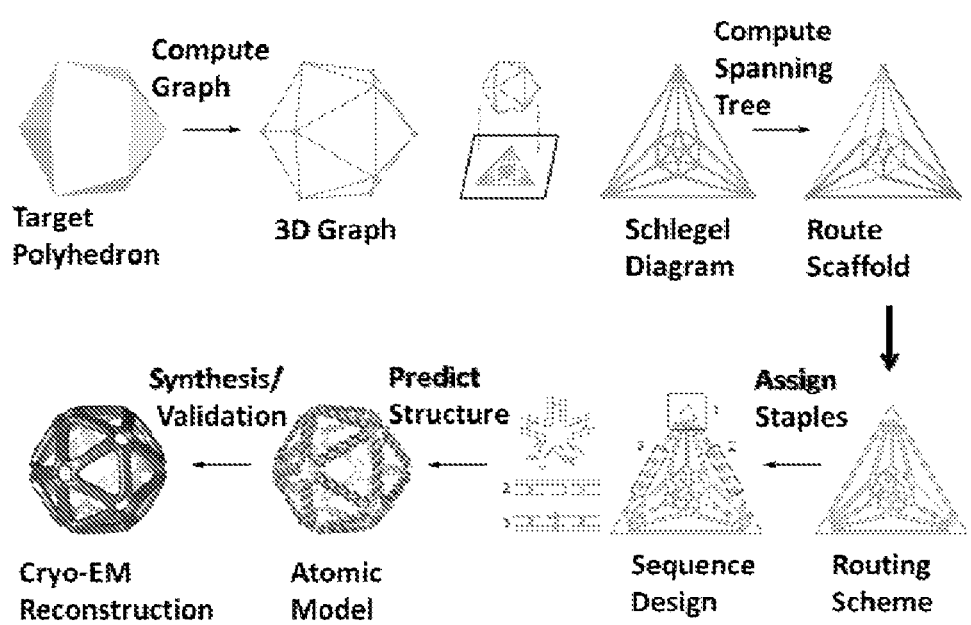
FIG. 1 is schematic illustrating the workflow for top-down sequence design of arbitrary polyhedral DNA origami objects. The scheme depicts: the specified target polyhedral shape; rendering the polyhedral geometry as a node-edge network based on an arbitrary closed surface representation, which is used to create a Schlegel diagram representation and to generate a spanning tree; the spanning tree is used as input to the formula that generates a scaffolding route, from which the routing scheme is determined; the oligonucleotide sequence of the single-stranded scaffold and staple assignment is determined; three different regions depicted as boxes (1, 2 and 3) represent three different types of staple strand, at the vertices, edges and DX crossovers, respectively; the atomic structure is generated assuming canonical B-form DNA geometry, and compared with 3D reconstruction from cryo-electron microscopic imaging.

The term "nucleotide" refers to a molecule that contains a base moiety, a sugar moiety and a phosphate moiety. Nucleotides can be linked together through their phosphate moieties and sugar moieties creating an inter-nucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate). There are many varieties of these types of molecules available in the art and available herein.

The terms "oligonucleotide" or a "polynucleotide" are synthetic or isolated nucleic acid polymers including a plurality of nucleotide subunits.

The terms "nucleic acid," "polynucleotide," and "oligonucleotide" are interchangeable and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones, locked nucleic acid). In general and unless otherwise specified, an analogue of a particular nucleotide has the same base-pairing specificity; i.e., an analogue of A will base-pair with T. When double-stranded DNA is described, the DNA can be described according to the conformation adopted by the helical DNA, as either A-DNA, B-DNA, or Z-DNA. The B-DNA described by James Watson and Francis Crick is believed to predominate in cells, and extends about 34 Å per 10 bp of sequence; A-DNA extends about 23 Å per 10 bp of sequence, and Z-DNA extends about 38 Å per 10 bp of sequence.

In some cases nucleotide sequences are provided using character representations recommended by the International Union of Pure and Applied Chemistry (IUPAC) or a subset thereof. IUPAC nucleotide codes used herein include, A=Adenine, C=Cytosine, G=Guanine, T=Thymine, U=Uracil, R=A or G, Y=C or T, S=G or C, W=A or T, K=G or T, M=A or C, B=C or G or T, D=A or G or T, H=A or C or T, V=A or C or G, N=any base, "." or "-"=gap. In some embodiments the set of characters is (A, C, G, T, U) for adenosine, cytidine, guanosine, thymidine, and uridine respectively. In some embodiments the set of characters is (A, C, G, T, U, I, X, Ψ) for adenosine, cytidine, guanosine, thymidine, uridine, inosine, uridine, xanthosine, pseudouridine respectively. In some embodiments the set of characters is (A, C, G, T, U, I, X, Ψ, R, Y, N) for adenosine, cytidine, guanosine, thymidine, uridine, inosine, uridine, xanthosine, pseudouridine, unspecified purine, unspecified pyrimidine, and unspecified nucleotide respectively. The modified sequences, non-natural sequences, or sequences with modified binding, may be in the genomic, the guide or the tracr sequences.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

The terms "cleavage" or "cleaving" of nucleic acids, refer to the breakage of the covalent backbone of a nucleic acid molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered "sticky" ends. In certain embodiments cleavage refers to the double-stranded cleavage between nucleic acids within a double-stranded DNA or RNA chain.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or MEGALIGN (DNASTAR) software is used to align sequences. Those skilled in the art can determine appropriate parameters for measuring alignment, including any formulas needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or formula's alignment of A and B and Y is the total number of residues in B. If the length of sequence A is not equal to the length of sequence B, the percent sequence identity of A to B will not equal the percent sequence identity of B to A. Mismatches can be similarly defined as differences between the natural binding partners of nucleotides. The number, position and type of mismatches can be calculated and used for identification or ranking purposes.

The term "endonuclease", refers to any wild-type or variant enzyme capable of catalyzing the hydrolysis (cleavage) of bonds between nucleic acids within a DNA or RNA molecule, preferably a DNA molecule. Non-limiting examples of endonucleases include type II restriction endonucleases such as FokI, HhaI, HindIII, NotI, BbvCI, EcoRI, BglII, and AlwI. Endonucleases comprise also rare-cutting endonucleases when having typically a polynucleotide recognition site of about 12-45 basepairs (bp) in length, more preferably of 14-45 bp. Rare-cutting endonucleases induce DNA double-strand breaks (DSBs) at a defined locus. Rare-cutting endonucleases can for example be a homing endonuclease, a mega-nuclease, a chimeric Zinc-Finger nuclease (ZFN) or TAL effector nuclease (TALEN) resulting from the fusion of engineered zinc-finger domains or TAL effector domain, respectively, with the catalytic domain of a restriction enzyme such as FokI, other nuclease or a chemical endonuclease including CRISPR/Cas9 or other variant and guide RNA.

The term "exonuclease", refers to any wild type or variant enzyme capable of removing nucleic acids from the terminus of a DNA or RNA molecule, preferably a DNA molecule. Non-limiting examples of exonucleases include exonuclease I, exonuclease II, exonuclease III, exonuclease IV, exonuclease V, exonuclease VI, exonuclease VII, exonuclease VII, Xm1, and Rat1.

In some cases an enzyme is capable of functioning both as an endonuclease and as an exonuclease. The term nuclease generally encompasses both endonucleases and exonucleases, however in some embodiments the terms "nuclease" and "endonuclease" are used interchangeably herein to refer to endonucleases, i.e., to refer to enzyme that catalyze bond cleavage within a DNA or RNA molecule.

As used herein, the term "ligating" refers to enzymatic reactions in which two double-stranded DNA molecules are covalently joined, for example, catalyzed by a ligase enzyme.

As used herein, the terms "aligning" and "alignment" refer to the comparison of two or more nucleotide sequence based on the presence of short or long stretches of identical or similar nucleotides. Several methods for alignment of nucleotide sequences are known in the art, as will be further explained below.

The terms "scaffolded DNA origami", "DNA origami" or "DNA nanostructure" are used interchangeably. They can refer to methods of using numerous short single strands of nucleic acids (staple strands) (e.g., DNA) to direct the folding of a long, single strand of polynucleotide (scaffold strand) into desired shapes on the order of about 10-nm to a micron or more, and the structures form therefrom.

The term polyhedron refers to a three-dimensional solid figure in which each side is a flat surface. These flat surfaces are polygons and are joined at their edges.

The terms "staple strands" or "helper strands" are used interchangeably. "Staple strands" or "helper strands" refer to oligonucleotides that hold the scaffold DNA in its three-dimensional wireframe geometry. Additional nucleotides can be added to the staple strand at either 5' end or 3' end, and those are referred to as "staple overhangs". Staple overhangs can be functionalized to have desired properties such as a specific sequence to hybridize to a target nucleic acid sequence, or a targeting element. In some instances, the staple overhang is biotinylated for capturing the DNA nanostructure on a streptavidin-coated bead. In some instances, the staple overhang can be also modified with chemical moieties. Non-limiting examples include Click-chemistry groups (e.g., azide group, alkyne group, DIBO/DBCO), amine groups, and Thiol groups. In some instances some bases located inside the oligonucleotide can be modified using base analogs (e.g., 2-Aminopurine, Locked nucleic acids, such as those modified with an extra bridge connecting the 2' oxygen and 4' carbon) to serve as linker to attach functional moieties (e.g., lipids, proteins). Alternatively DNA-binding proteins or guide RNAs can be used to attach secondary molecules to the DNA scaffold.

The term "geometry" or "geometric parameters" refer to the angles and/or relative distances that describe any two connected edges of a shape, such as those that define the relative position of faces, and the properties of the vertices and edges that form the three-dimensional solid.

The term "arbitrary geometry" refers to a non-specific three dimensional shape, for example, any desired three-dimensional closed surface that can be rendered as a polyhedral wire mesh.

The term "network" is a representation of the lines and vertices that define the relations between the line and vertices within the objects. In some embodiments, vertices are represented as nodes and lines are represented as edges in a graph. The degree (or valency) of a vertex of a graph is the number of edges incident to the vertex.

The term "spanning tree" refers to a subset of edges and all of the nodes in a graph, such as the graphical node-edge network corresponding to the lines and vertices of a polyhedral shape. Typically, spanning trees include all the vertices. Different spanning trees for a given network can cover different edges. A breadth-first spanning tree includes the maximum number of branches.

The term "Euler Path", "Eulerian Trail", or "Eulerian Path" refer to a trail in a graph which visits every edge exactly once. The terms "Euler circuit", "Euler Cycle", "Eulerian Cycle" or "Eulerian Circuit" are used interchangeably and refer to a trail in a graph which visits every edge exactly once, and which starts and ends on the same vertex. For the existence of Eulerian cycles it is necessary that every vertex has even degree, and all of its vertices with nonzero degree belong to a single connected component.

The term "loop-crossover structure" refers to 3D structure in which endpoints are joined such that every duplex becomes part of a loop, and positions of possible scaffold double crossovers are found between two loops.

The term "dual graph" refers to the graph by converting each loop to a node and each double crossover to edge.

The terms "DX crossover", or "antiparallel crossover", or "DX motif" are used interchangeably, and refer to an anti-parallel double crossover nucleic acid motif consisting of two four-arm Holliday junctions, joined by two helical arms at two adjacent arms. The antiparallel orientation of the nucleic acid helical domains in antiparallel DX motifs implies that the major grooves of one nucleic acid helix faces the minor groove of the other engaged helices come together in each turn.

The term "PX crossover", or "parallel crossover", or "PX motif" are used interchangeably to refer to a four-stranded DNA motif wherein two parallel double helices are joined by reciprocal exchange (crossing over) of strands of the same polarity at every point where the strands come together (see Seeman, *Nano Letters* 1, (1), pp. 22-26 (2001); Wang, *PNAS,* 9. 107 (28), pp. 12547-12552 (2010)). No strand breakage and rejoining is needed, because two double helices can form PX-DNA merely by inter-wrapping. The reciprocal exchange between two double stranded nucleic acid helices can occur between two helices having either the same or opposite stand polarity. An exemplary PX motif is the "paranemic crossover". PX motifs are usually followed by a pair of numbers, e.g. PX65 motif, that describe the number of base pairs in the major groove and minor groove of the double helices, respectively, between parallel crossovers. The number of base pairs in the major groove is typically greater than that in the minor groove. Exemplary, PX motifs include PX65, PX75, PX85, PX95, PX64, PX74, and PX66 (Maiti, et al., *Biophysical Journal.* 90, 1463-1479 (2006); Shen, et al., *J. Am. Chem. Soc.* 126, 1666-1674 (2004)).

The term "bait sequence" refers to a single-stranded nucleic acid sequence that is complementary to any fragment of a target nucleic acid sequence, such as an RNA, for capturing the target nucleic acids. Typically, bait sequences are appended to or otherwise are present as part of the staple sequence of a nucleic acid nanostructure, for example, as an "overhang" sequence of nucleic acids. In some embodiments, bait sequences are complementary to loop regions or single-stranded regions of target RNAs for capturing the RNAs. Alternatively, the bait sequences tether proteins or other ligands that target binding regions to capture a structured RNA or DNA assembly of interest via avidity enhancement.

The term "nucleic acid capture" refers to binding of any nucleic acid molecule of interest having complementary nucleic acid sequences to the bait sequences on the DNA nanostructures, or having affinity for the capture bait probe employed, and being immobilized or attached to the DNA nanostructures via hybridization to the bait sequence, or binding. For example, "RNA capture" refers to binding of any ribonucleic acid molecule of interest to the bait sequences on the DNA nanostructures. Nucleic acids of interest can bind to the inside or outer surface of a nucleic acid nanostructure.

The phrase that a molecule "specifically binds" to a target refers to a binding reaction which is determinative of the presence of the molecule in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity. Specific binding between two entities means an affinity of at least $10^6$, $10^7$, $10^8$, $10^9$, or $10^{10}$ M-1. Affinities greater than $10^8$ M-1 are preferred.

The term "targeting molecule" refers to a substance which can direct a nanoparticle to a receptor site on a selected cell or tissue type, can serve as an attachment molecule, or serve to couple or attach another molecule. The term "direct" refers to causing a molecule to preferentially attach to a selected cell or tissue type. This can be used to direct cellular materials, molecules, or drugs, as discussed below.

The terms "antibody" or "immunoglobulin" are used to include intact antibodies and binding fragments thereof. Typically, fragments compete with the intact antibody from which they were derived for specific binding to an antigen fragment including separate heavy chains, light chains Fab, Fab' F(ab')2, Fabc, and Fv. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes a bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai and Lachmann, *Clin. Exp. Immunol.*, 79:315-321 (1990); Kostelny, et al., *J. Immunol.*, 148, 1547-1553 (1992).

The terms "epitope" or "antigenic determinant" refer to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10, amino acids, in a unique spatial conformation. Methods of determining spatial conformation of epitopes include, for example, x-ray crystallography and 2-dimensional nuclear magnetic resonance.

The term "small molecule," as used herein, generally refers to an organic molecule that is less than about 2,000 g/mol in molecular weight, less than about 1,500 g/mol, less than about 1,000 g/mol, less than about 800 g/mol, or less than about 500 g/mol. Small molecules are non-polymeric and/or non-oligomeric.

II. Methods for Design of Nucleic Acid Nanostructures

Systems and methods for the automated, step-wise design of a nucleic acid nanostructure having arbitrary geometries have been established. The systems and methods generally involve rendering the geometric parameters of a desired polyhedral form as a node-edge network, and determining the nucleic acid scaffold route and staple design parameters necessary to form the desired polyhedral structure. Therefore, methods for generating the sequences of the single-stranded nucleic acid scaffold and the nucleic acid sequence of staple strands that combine to form a nucleic acid nanostructure having the desired shape are provided. An exemplary method for designing a nucleic acid nanostructure having a desired polyhedral form includes selecting a desired 3D polyhedral or 2D polygon form as a target structure; providing geometric parameters and physical dimensions of the a target structure for a selected 3D polyhedral or 2D polygon form; identifying the route of a single-stranded nucleic acid scaffold that traces throughout the entire target structure; and generating the sequences of the single-stranded nucleic acid scaffold and/or the nucleic acid sequence of staple strands that combine to form a nucleic acid nanostructure having the desired shape. DNA nanostructures having the desired shape are produced by folding a long single stranded polynucleotide, referred to as a "scaffold strand", into a desired shape or structure using a number of small "staple strands" as glue to hold the scaffold in place. Typically, the number of staple strands will depend upon the size of the scaffold strand, the complexity of the shape or structure, the types of crossover motifs employed, and the number of helices per edge. For example, for relatively short scaffold strands (e.g., about 150 to 1,500 base in length) and/or simple structures the number of staple strands are small (e.g., about 5, 10, 50 or more). For longer scaffold strands (e.g., greater than 1,500 bases) and/or more complex structures, the number of staple strands can be several hundreds to thousands (e.g., 50, 100, 300, 600, 1,000 or more helper strands). Using parallel crossover motifs, however, the number of staples can be reduced, even to zero. The choice of staple strands and, in some instances, the programmed self-hybridization of the scaffold strand, determine the pattern. In some embodiments, a software program is used to identify the staple strands needed to form a given design.

Typically, the methods include one or more of the following steps:

(a) Selecting a target polyhedral structure;

(b) Choosing the cross-section geometry of the edge of 2 helices, 4 helices on a square or honeycomb lattice, 6 helices on a square or honeycomb lattice, or any even number of helices on a square or honeycomb lattice.

(c) Determining the spatial coordinates of all vertices, the edge connectivity between vertices, and the faces to which vertices belong in the target structure;

(d) Identifying the route of a single-stranded nucleic acid scaffold sequence that traces throughout the entire target polyhedral structure, and (e) Determining the nucleic acid sequence of the single-stranded nucleic acid scaffold and, optionally, the nucleic acid sequence of corresponding staple strands.

Typically, the route of the scaffold nucleic acid is identified by (i) Determining edges that form the spanning tree of the node-edge network (for example, using the Prim's Formula);

(ii) Bisecting each edge that does not form the spanning tree to form two split edges;

(iii) Determining an Eulerian circuit that passes twice along each edge of the spanning tree. The direction of the continuous scaffold sequence is reversed at the bisecting point of the node-edge network in a DX-anti-parallel crossover, and the Eulerian circuit defines the route of a single-stranded nucleic acid scaffold sequence that passes throughout the entire structure. Staple strands are located at the vertices and edges of the route of the single-stranded nucleic acid scaffold sequence determined in (d).

Typically, for the origami nanostructures that incorporate parallel crossovers, the route of the scaffold nucleic acid is identified by determining an Eulerian circuit that passes twice or more than twice along each edge of the wireframe. Based on the length and spanning tree classification, units of partial scaffold routing are superimposed and connected to complete the circuit.

In some embodiments the methods further include the steps by (i) Detaching and scaling each edge of the initial geometry to represent the number of helixes as lines indicating their lengths and endpoints;

(ii) Generating the loop-crossover structure joining endpoints and finding double crossovers between two loops;

(iii) Generating the dual graph of the loop-crossover by converting each loop to a node and each double crossover to edge;

(vi) Computing the spanning tree of the dual graph of the loop-structure (for example, using the Prim's Formula);

(v) Inverting the dual graph back to the loop-crossover structure but without the double-crossovers corresponding to the non-member's spanning tree; Edges that are members of the spanning tree correspond to the subset of crossovers required to complete the Eulerian circuit.

In some embodiments the methods further include the step of (f) Modelling the 3-Dimensional co-ordinates of each nucleic acid according to the parameters determined in (c) and (d).

In further embodiments the methods further include the step of (g) Assembling and optionally purifying the nucleic acid nanostructures designed by the methods of any of the steps (a) through (d).

Each of these steps is discussed in more detail, below.

The method described herein is a "top-down approach" of the structure (i.e., only input is a "shape" and the number and geometry of helices per edge). Nothing else is required, except for optional selection of a size and an input sequence (otherwise, default parameters can be used for both).

Default parameters for input scaffold size, nucleic acid type, input scaffold sequence, edge length, number of helices per edge, cross-sectional morphology of edges and vertex geometry (i.e., beveled or non-beveled edges) can be used as necessary to generate the sequences of staples and/or scaffold nucleic acid when no value is specified. For example, in some embodiments, the default nucleic acid is B-DNA, and the default edge-length is 31 bases, with 2 helices per edge. In some embodiments, the default nucleic acid scaffold sequence is the 7,249 nt M13pm18 bacteriophage DNA. In some embodiments, when the number of helices per edge is specified, but the vertex morphology is not specified, the default vertex geometry is to use honeycomb morphology with beveled edges.

This is fundamentally different from bottom-up design methods. For example, the "bottom-up approach" does not produce the sequences of staple strands, but requires manual intervention via an heuristic approach, using multiple duplex arms combined together to form the structure (i.e., may not use a single scaffold sequence throughout). The top-down methods start with the desired output, i.e. the final structure and the use of a specific scaffold, and generate the sequences required to synthesize that output, using a single ssDNA scaffold that is routed throughout the entire structure. The scaffold can be a user-defined scaffold sequence, and the staple sequences are varied accordingly.

The approach is extremely powerful because it can exploit the single scaffold strand to enable down-stream applications, such as DNA RAM storage (i.e., a single strand of DNA is folded into each object), as well as other applications.

The formula uses a maximum-breadth spanning tree to determine positions of the scaffold crossovers for the scaffold routing. Any spanning tree, however, will lead to a valid scaffold routing. The nanostructures themselves are distinct in having a continuous single stranded nucleic acid sequence routed through each edge of the structure.

A. Providing a Target Structure

Methods for the step-wise design of a nucleic acid nanostructure, based on the arbitrary wireframe geometry of the desired (target) structure as a starting model have been developed. The methods are useful to provide design parameters, such as the sequence of a single-stranded DNA nucleic acid "scaffold", as well as corresponding single-stranded edge and vertices "staple" sequences necessary to form a nucleic acid nanostructure having the shape of the input structure.

1. Selection of Target Structure

The methods require geometric parameters that define the target shape as input. Therefore, the starting point for the design process is the selection of a target shape. Any arbitrary geometric shape that can be rendered as a "wireframe" model can be selected as input for the design of nucleic acid assemblies.

Exemplary target shapes include three-dimensional structures, including, but not limited to, Platonic polyhedrons, Archimedean polyhedrons, Johnson polyhedrons, Catalan solids, or asymmetric three-dimensional structures. In some embodiments, the target structure has a programmed geometry that is topologically equivalent to that of a sphere. In other embodiments, the target structure has a programmed geometry that is topologically distinct to that of a sphere. For example, target structures including nested structures, and toroidal structures can be designed using the described methods. In other embodiments, the target structure has a programmed geometry that is topologically equivalent to a plane. For example, target structures including triangular mesh, square mesh, or other mesh.

Target structures can be selected based upon one or more design criteria, or can be selected randomly. In some embodiments, structures are selected based on existing 'natural' 3-dimensional organizations (e.g., virus capsids, antigens, toxins, etc.). Therefore, in some embodiments, target shapes are designed for use directly or as part of a system to mediate a biological or other responses which are dependent upon, or otherwise influenced by 3D geometric spatial properties. For example, in some embodiments, all or part of a structure is designed to include architectural features known to elicit or control one or more biological functions. In some embodiments, structures are designed to fulfill the 3D geometric spatial requirements to induce, prevent, stimulate, activate, reduce or otherwise control one or more biological functions. Typically, the desired shape defines a specific geometric form that will constrain the other physical parameters, such as the absolute size of the particle. For example, the minimum size of nucleic acid nanostructures designed according to the described methods will depend upon the degree of complexity of the desired shape.

i. 2-Dimensional Wireframe Structures

Target structures can be any solid in two dimensions. Therefore, target structures can be a grid or mesh or wireframe topologically similar to a 2D surface or plane. The grid or mesh can be composed of regular or irregular geometries that can be tessellated over a surface.

Exemplary target structures include triangular lattices, square lattices, pentagonal lattices, or lattices of more than 5 sides. 2D structures can be designed to have varied length and thickness in each dimension. In some embodiments, the edges of 2D nanostructures include a single nucleic acid helix. In other embodiments, the edges of 2D nanostructures include two or more nucleic acid helices. For example, in some embodiments, each edge of the 2D nanostructure includes 2 helices, 4 helices, 6 helices or 8 helices, or more than 8 helices, up to 100 helices per edge, although theoretically unlimited in number.

ii. Polyhedral Structures

Target structures can be any solid in three dimensions that can be rendered with flat polygonal faces, straight edges and sharp corners or vertices.

Exemplary basic target structures include cuboidal structures, icosahedral structures, tetrahedral structures, cuboctahedral structures, octahedral structures, and hexahedral structures. In some embodiments, the target structure is a convex polyhedron, or a concave polyhedron. For example, in some embodiments, the methods design nucleic acid assemblies of a uniform polyhedron that has regular polygons as faces and is isogonal. In other embodiments, the methods design nucleic acid assemblies of an irregular polyhedron that has unequal polygons as faces. In further embodiments, the target structure is a truncated polyhedral structure, such as truncated cuboctahedron.

Platonic polyhedrons include polyhedrons with multiple faces, for example, 4 faces (tetrahedron, (1)), 6 faces (cube or hexahedron (2), 8 faces (octahedron), 12 faces (dodecahedron), and 20 faces (icosahedron).

Figure 2A:
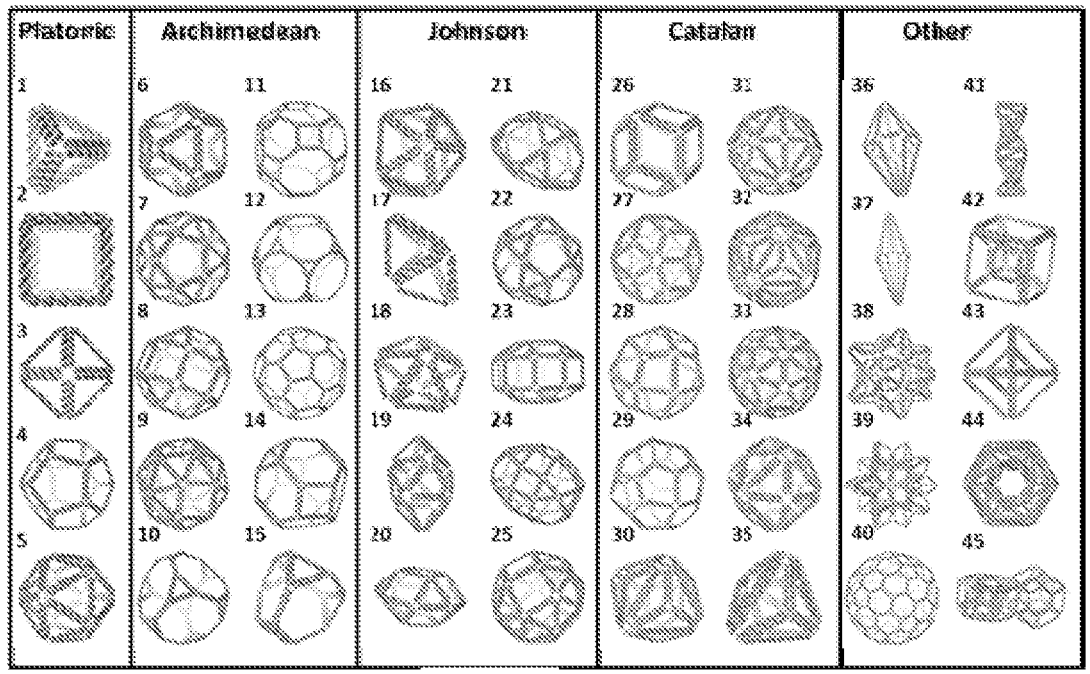
FIGS. 2A and 2B are charts representing atomic model structures (FIG. 2A), and face-shaded models (FIG. 2B), respectively for each of several polyhedral shapes. Each shape is appended with a number, 1-45, respectively. The same numbering scheme used in FIG. 2A
Figure 2B:
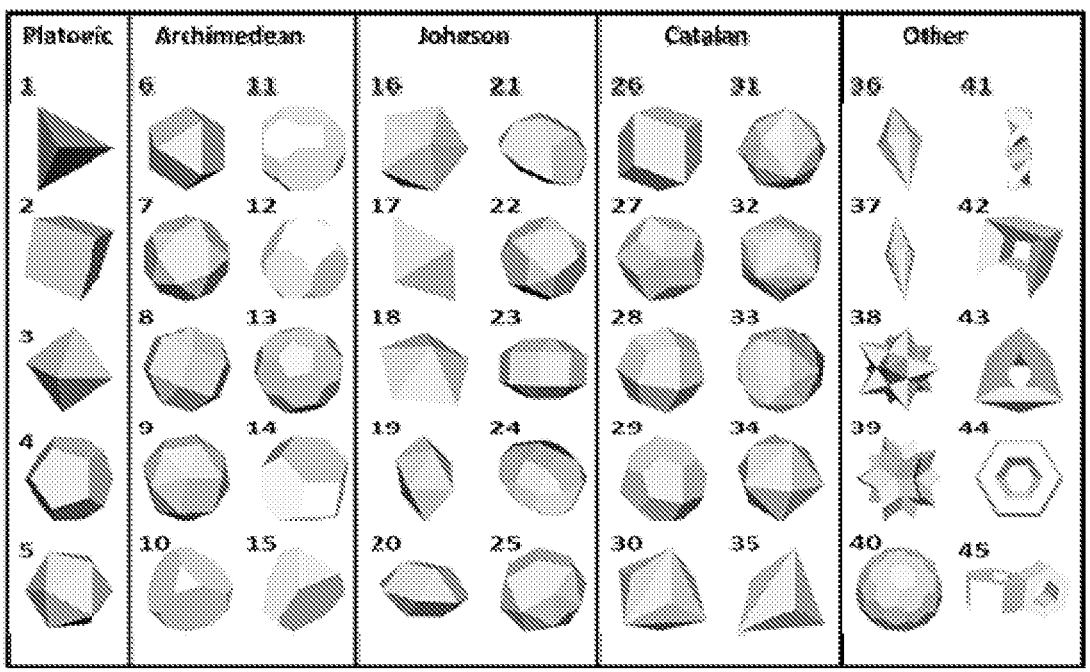
Figure 9I:
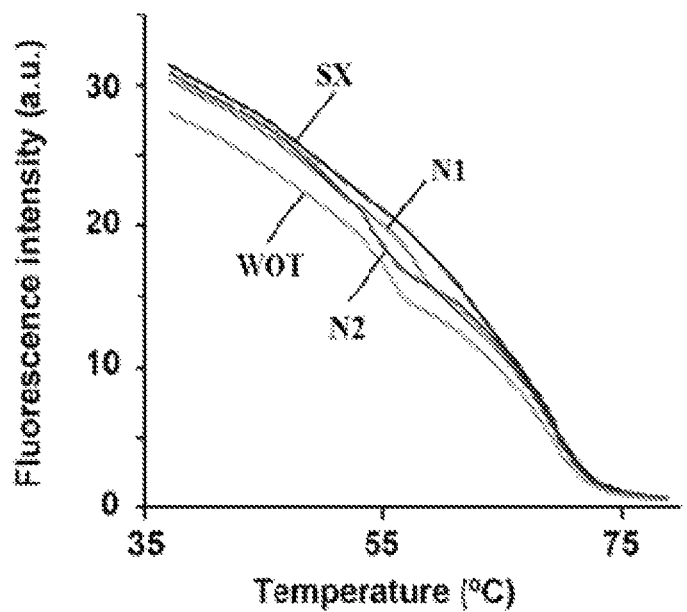
FIGS. 9I-9L are line graphs of qPCR data.
Figure 9J:
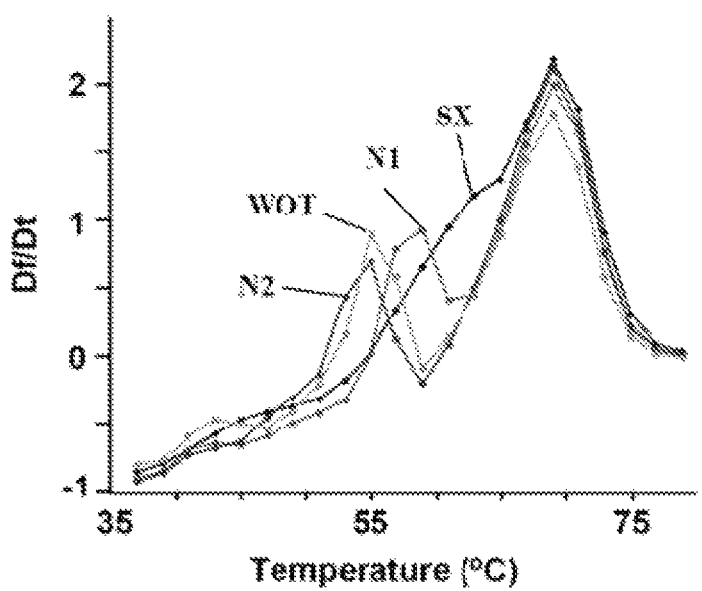
Figure 9K:
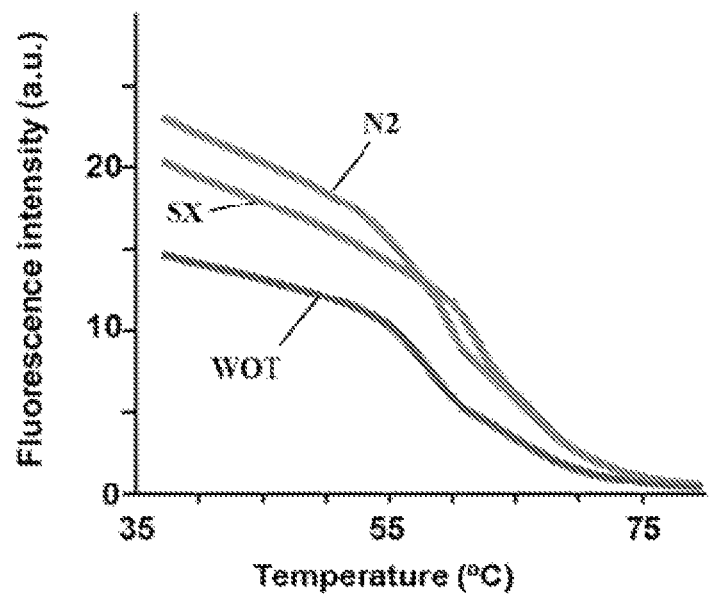
Figure 9L:
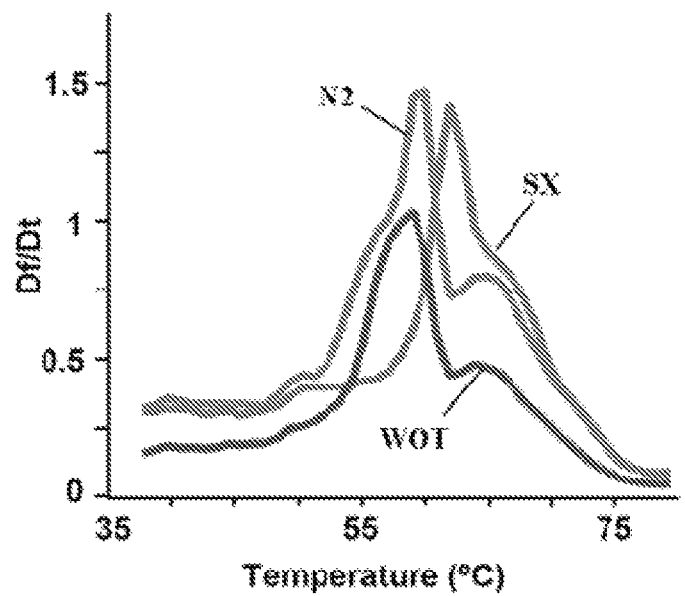

In some embodiments, the target structure is a nucleic acid assembly that has a non-spherical geometry. Therefore, in some embodiments, the target structure has a geometry with "holes". Exemplary non-spherical geometries include toroidal polyhedra and nested shapes. Exemplary toroidal polyhedra include a torus and double torus. Exemplary topologies of nested shapes include nested cube and nested octahedron. Exemplary polyhedral forms are depicted in FIGS. 2A-2B.

In other embodiments, target structures can be a combination of one or more of the same or different polyhedral forms, linked by a common contiguous edge.

iii. Reinforced Polyhedral Structures

In some embodiments, the target structure is a reinforced structure. Reinforced structures are structures that share the same polyhedral form as the equivalent, non-reinforced structure, and include one or more additional edges spanning between two vertices. Typically, the reinforced structure contains at least one or more edges than the corresponding non-reinforced structure. In some embodiments, additional structural elements that appear as "cross-bars" spanning between two vertices are introduced.

In some embodiments, a structure is reinforced by the addition of one or more edges passing internally within the space enclosed by the structure. Therefore, in some embodiments reinforced structures encapsulate a smaller volume than the corresponding non-reinforced structure. In other embodiments, a structure is reinforced by the addition of one or more edges that connects vertices by spanning a face of the polyhedron. In further embodiments, a polyhedral nanostructure is reinforced by including one or more additional edges that connect vertices by spanning a face of the polyhedron and one or more additional edges that connect vertices by passing internally within the space enclosed by the structure. In some embodiments, a polyhedral nanostructure is reinforced by addition of one or more edges that bisects a face of the polyhedron and addition of one or more vertices.

iv. Other Structures

In some embodiments the desired structure has a shape that is visually or geometrically similar to a biological structure, such as the shape of a viral particle, or a sub-component of a viral particle; a protein; or a sub-component of a protein.

2. Providing Geometric Parameters of the Target Structure

The methods can include the step of providing the geometric parameters that define the target structure. Geometric parameters include the spatial coordinates of all vertices, the edge connectivity between vertices, and the faces to which vertices belong. Geometric parameters can be determined using any means that represents the form of the target structure. Typically, geometric parameters are determined by rendering the target structure as a wire-frame mesh. In some embodiments the determination of geometric parameters for an input shape is carried out using a computer-based interface. Therefore, in some embodiments geometric parameters of a target shape are determined in silico. Typically, in silico determination of geometric parameters can require input of a target shape, or input of the rendered wire-frame model of the target shape. In some embodiments, the only input is a target shape, or input of the rendered wire-frame model of the target shape. For example, in some embodiments, following input of a target shape and/or geometric parameters corresponding to a target shape, all other steps are performed within an automated system, such as by a computer using software including each of the method steps, optionally incorporating one or more default parameters. In some embodiments, the input is a 2-dimensional shape, or geometric parameters of a 2-dimensional shape. In some embodiments, the target structure is the three-dimensional form corresponding to the 2-dimensional shape. For example, a 3-dimensional cuboidal structure can be inferred from input of the geometric parameters of one or more of the faces of the 3-dimensional structure. In an exemplary embodiment, a single square face is input and the corresponding regular cube is provided as input in wire-frame conformation.

i. Wire-Frame of Arbitrary Geometry

The methods can determine nucleic acid scaffold and staple sequences for nanostructures having the shape of any open or closed geometric surface that can be rendered as a polyhedral surface wire-frame model.

Therefore, the methods include reduction of the target structure as a model that represents each edge of the physical object where two or more continuous smooth surfaces meet, or by connecting an object's constituent vertices using straight lines. Typically, a wireframe model of a geometric shape represents the minimum number of characteristic edges and vertices that define the 2D or 3D shape.

Typically, when some or all of the methods are carried out using a computer-based interface, the geometric parameters of a target shape are provided in a standard polyhedral file format. The geometric parameters of any open or closed, orientable surface network can serve as input using any file format that specifies polygonal geometry known in the art, including but not limited to, Polygon File Format (PLY), Stereolithography (STL), or Virtual Reality Modeling Language (WRL). When a standard polyhedral file format is provided, the code includes a parser to convert the standard polyhedral files into the required inputs.

ii. Edge Geometry

In addition to the geometric parameters of a target shape, the cross-sectional shape on all edges is defined. Exemplary cross-sectional forms include two double-stranded nucleic acid helices; a square lattice (minimum four double helices); and honeycomb lattice (minimum six double helices). Each double helical section has an identification number which determines the orientation of the helix along the edge direction. To make antiparallel helixes given in the bundle of helixes, the identification number should be even when the neighboring helix has the odd number.

In some embodiments, one or more edges of a shape is defined as having a square cross-sectional lattice including an even number of double helices. For example, in some embodiments, each edge includes four helices, six helices or more than six double helices, for example, 36, or 64 double helices. The square lattice is composed such that each of helices are arranged with rectangular symmetry across the axis of the edge and such that any one helix can have crossovers along the edge with up to four other helices. In some embodiments, one or more edges of a shape is defined as having a honeycomb cross-sectional lattice including six double helices, eight double helices, ten double helices or more than ten double helices, for example, 12, 24, or 48 double helices arranged in a honeycomb pattern. The honeycomb lattice is composed such that each of the helices are arranged on a hexagon pattern across the axis of the edge and such that each helix can have crossovers with up to three other helices along the edge.

iii. Vertex Geometry

Typically, a vertex of "degree N" has "N" number of edges emerging from it. For example, if a vertex is of degree 4, it is contacted by 4 edges. An Euler circuit through a node-edge network of a given shape is guaranteed when the degree of every vertex is even. Therefore, in preferred embodiments, the degree of every vertex in the node-edge network is even, such that the Eulerian Circuit of the graph passes through each of the edges once in each direction. By choosing to have an even number of duplexes per edge in the wireframe, the vertices of the final DNA nanostructure are technically of even degrees, even if some or all of the vertices in the wireframe input are of odd degrees.

There are several conventions by which to define the inradius of a vertex, which will vary according to the number of edges that combine at the vertex "junction", and whether the angles between each edge entering or leaving the junction are equal or different relative to one another (see FIGS. 5A-5F). For example, the angles at the vertex determine the distance between the vertex and the beginning of the edge. For vertices with equal face angles (FIGS. 5A and 5D) the distance between the vertex and the beginning of the edge is the inradius of the regular polygon defined by the width of each edge in the junction. For vertices with unequal face angles, the backbone can be stretched (FIGS. 5B and 5E), or the vertex can incorporate nucleotide overlap (FIGS. 5C and 5F).

For structures including more than 2 double-helices per edge, the cross-geometry of the nucleic acid scaffold and/or staple strands on all vertices is defined for the junctions between each edge, in relation to the interface with the two or more further edges. For example, when an edge is defined as having a honeycomb cross-sectional form, the geometry of each honeycomb lattice edge can be defined as either having a beveled or non-beveled edge at the junction of multiple edges (vertex) (see FIGS. 12A-12E and FIG. 13).

In one embodiment of a non-beveled type, between two neighboring edges at a vertex exactly one helix of one edge is involved with exactly one other helix of the other edge by both a scaffold crossover as well as possibly a staple crossover, irrespective of edge lattice type. All other helices on the edge are extended or truncated to the crossover position near to the vertex. Scaffold or staple strands may be unpaired at the vertex, or no unpaired scaffold or staples may be present.

In one embodiment of the beveled type, between two neighboring edges at a vertex one helix, two helices, three helices, or more than three helices from one edge are connected with an equivalent number of helices on the neighboring edge. Thus, for example, three helices on one edge are connected to three helices on a neighboring edge. The edge length of two adjacent edges at the i-th vertex is modified when the angle between two edges is relatively larger than others. At the 4-arm junction, each of four edges denoted by from 'a' to 'd' is connected at the vertex, i. The minimum angle, $\theta^i_{min}$ at the i-th vertex is found, and the initial off-set distance (apothem), $r_i$ is calculated by $\theta^i_{min}$ and the number of arms in i-th vertex. Two cylinders (in case of the DX tile design) are drawn on each edge with initial off-set distance, $r_i$. When two cylinders located in adjacent edges do not contact each other (not close), the new off-set distance, $d^i_{a,d}$, is determined, in which the subscript a,d represents the edge identifier. The new off-set distance, $d^i_{a,d}$ can be solved with two given distance $m^i_{a,d}$, and $n^i_{a,d}$ and the given angle $\theta_{a,d}$. The helix continues such that each helix will not sterically clash with any other helix, and crossovers of scaffold and staples will occur at closest contact between any two neighboring helices but on different edges.

Thus, the geometry of a flat type will be connected to a neighboring edge by one scaffold and/or staple crossover at the vertex. The geometry of a beveled type will be connected to a neighboring edge by the number of helices of the edge coming into the vertex divided by the number of edges the incoming edge is a neighbor to. In spherical topologies this is defined as the number of helices of the edge divided by 2. Thus, as an example, a beveled edge vertex with an edge composed of six helices total on a honeycomb lattice will share three scaffold and/or staples crossed-over to three helices on a neighboring edge while the other three helices will crossover to helices on the other neighboring edge of the particle. Typically the choice of vertex geometry is chosen by the generator of the design prior to routing and the geometry, and placement of the crossover between the edges is automated based on extending or contracting all other helices to make crossovers at geometric positions without inducing steric clashing.

3. Providing Physical Parameters of the Target Structure

In addition to the geometric form of the target structure, the methods enable design of the physical parameters of the nucleic acid nanostructure. Physical parameters that can be specified by the user include size, molecular weight, core nucleic acid sequence, as well as pre-determination of stability. For example, the stability of the nucleic acid nanostructure in one or more solvents can be required. In an exemplary embodiment, a structure that exhibits stability in physiological salt concentrations is designed by the methods.

Therefore, the methods include design of customized nucleic acid nanostructures having a specified size, having a specified molecular weight, having a specified core nucleic acid sequence, and combinations thereof.

i. Size

Methods for the step-wise design of custom nucleic acid nanostructures can produce nanostructures of a desired size. Typically, the size of the nanostructures is specified as a function of the length of the edges that form the wire-frame model of the desired structure.

Typically, the desired length of each edge is specified. In preferred embodiments, the lengths of edges obey the natural geometry of DNA or RNA. Preferably, the specified length of each edge does not give rise to shape distortions that force deviation from the target geometry. Therefore, in preferred embodiments, the length of each edge is specified as a number of base-pairs (bp) or nucleotides (nt) that is determined to ensure that no over- or under-wind in nucleic acid duplexes occurs. Typically, the length of each edge is a multiple of the unit number of base-pairs that is required to reduce or prevent over- or under-wind in nucleic acid duplexes that form the edges of the desired nucleic acid nanostructure. In some embodiments, the unpaired nucleotides in the scaffold are used to ensure no-over- or under-wind in nucleic acid multiple duplexes occurs when the length of each edge is not the multiple of 10.5 bp.

In some embodiments the length of each edge is a multiple of 10.5 bp. In some embodiments, the length of each edge 10.5 bp is rounded up or down to the nearest nucleotide. In some embodiments the minimum length of any single edge is 31 bp. Any edge length smaller than 31 bp will create a scaffold crossover 5 nt away from the end of an edge (in the vertex staple region) and will not yield a large quantity of final folded nanostructure product. Typically, constraining edge lengths to be multiples of 10.5 bp does not limit or otherwise restrict the selection of the target shape.

In some embodiments the length of the edge is a multiple of 11 bp. In some embodiments the selection of edges having length of 33 bp, 44 bp, 55 bp, 66 bp, 77 bp, 88 bp, or larger than 88 bp. The minimum edge length allowed in this design paradigm is 33 bp.

In some embodiments, the desired structures have equal edge lengths throughout the geometry. For example, design of Platonic, Archimedean, or Johnson solids includes the selection of edges having a length of 31 bp, 42 bp, 52 bp, 63 bp, 73 bp, 84 bp, 94 bp, or larger than 94 bp.

In some embodiments, desired structures do not have equal edge lengths throughout the geometry. Therefore, in some embodiments rounding of edge lengths is required. When rounding of edge lengths is required, the method can design nanostructures including deviations between the specified target structure and final design. For example, deviations in lengths of edges can occur at one or more edges in a structure. In these cases, the desired minimum edge length (e.g., 31 bp, or 42 bp) is assigned to the shortest edge and the other edges are scaled and rounded appropriately. Therefore, in some embodiments, where deviations between the specified target structure and final design are associated with different edge-lengths, multiple nanostructures can be designed, having deviations at one or more different edges.

Typically, the rounding of edge lengths is carried out automatically, for example, by computer software. When using automated rounding to generate edge lengths, the user is advised to verify that edge lengths are satisfactory before proceeding to the scaffold routing procedure.

The dimensions of edges that are selected are associated with the overall dimensions of the resulting nucleic acid nanostructure. The size of a nanostructure designed by the described methods can be defined as the maximum length of the structure in a single plane. Typically, the methods can design structures having overall dimensions of approximately 10-1,000 nm, inclusive, such as 50-500 nm, 60-200 nm, or 60-100 nm, for example, 60 nm, 70 nm, 80 nm, 90 nm, 100 nm or larger than 100 nm.

The average minimum size of a nanostructure is typically restricted by the complexity of the desired shape. Therefore, in some embodiments, the desired size of the nanostructure is a characteristic that is used in the automated design of target shapes that fulfill the desired maximum and/or minimum size criteria.

ii. Molecular Weight

The custom nucleic acid nanostructures produced according to the disclosed methods have a molecular weight. Typically, the molecular weight of the nanostructures is a function of the mass of the nucleic acids forming each of the edges that form the wire-frame model of the desired structure. Typically, the methods design nucleic acid nanostructures that have a molecular weight of between 200 kilo daltons (kDa) and 1 mega dalton (1 mDa).

The molecular weight of a nanostructure is typically defined by the size and complexity of the desired shape. Therefore, in some embodiments, the desired molecular weight of the nanostructure is a characteristic that is used in the automated design of target shapes that fulfill a desired maximum and/or minimum molecular weight criteria. Thus, the disclosed methods for step-wise design of custom nucleic acid nanostructures can produce nanostructures having a predetermined or preset molecular weight.

iii. Nucleic Acid Scaffold Template Sequence

In some embodiments, the methods design the sequence of staples that give rise to nanostructure having the desired shape based on a corresponding nucleic acid sequence. Therefore, in some embodiments the input also includes providing one or more nucleic acid template sequences.

The nucleic acid template sequence can include natural nucleic acids or non-natural nucleic acids, or can include a combination of natural and non-natural nucleic acids.

In other embodiments, no input sequence is provided. Therefore, in some embodiments one or more known nucleic acid sequences are used as a default template sequence. In some embodiments the default template sequence is a sequence or a subset of a sequence corresponding to a bacteriophage. An exemplary default template sequence is a segment of the bacteriophage M13pm18. The M13mp18 single-stranded nucleic acid sequence is available at NCBI's website ncbi.nlm.nih.gov/nuccore/X02513 and is published as Genbank Accession Nos. X02513, M77815, and M11454 (FIG. 8A).

In other embodiments, a sequence is randomly generated. In further embodiments, the template sequence for the single-stranded DNA scaffold is determined based on the required scaffold length, for example, as determined by the Eulerian circuit corresponding to the desired shape according to the described methods. If the desired sequence is longer than the input sequence template, a sequence is randomly generated. For example, if the default template sequence is M13pm18, and the required sequence is longer than 7,249 nucleotides, a random single-stranded scaffold template sequence is generated, for example, by a computer.

Typically, the nucleic acid scaffold sequence is between 150 to 15,000 bases in length.

When DNA is used to create dsDNA helices within a nanostructure, DNA double-stranded helices having a particular conformation can be employed. For example, double-stranded DNA can be A-form DNA, B-form DNA or Z-form DNA.

B. Identifying Scaffold Routing for the Target Structure

The methods include identifying the route of the scaffold nucleic acid throughout the target structure, based on the information provided in the corresponding node-edge network of the corresponding polyhedron. Typically, the nodes and lines of the network correspond to the vertices and edges of the desired polyhedron. For example, Prim's formula can be used to find a breadth-first search spanning tree, one with the most branches. The spanning tree formula does not impose restrictions on the topology of the network. Therefore, the methods provide routing information for any arrangement of nodes and edges using a spanning tree to define the placement of scaffold crossovers.

1. Nanostructures with Antiparallel Double Crossover (DX) Motifs

In some embodiments, the methods require including at least one edge having one "DX" (anti-parallel scaffold crossover) motif. The edges with zero DX scaffold crossovers meet the definition of a spanning tree of a network. Therefore, a single DX anti-parallel scaffold crossover is positioned along every edge that does not form part of the spanning tree of the graph, preferably as close to the center of the edge as possible.

The scaffold strand is routed by a method that identifies the Eulerian circuit through the entire network, such that the strand enters each vertex from a first edge and exits the vertex from an adjacent edge that shares a face with the first edge. The route of the scaffold strand is determined according to the rules that the scaffold strand does not enter and exit from the same edge, and the scaffold strand does not exit from an edge that is not-adjacent to the edge it enters. Therefore, the scaffold routing process does not allow for the intersection of DNA strands and the process produces only edges that are connected to the vertex.

Each of the steps involved in determining the route of the single-stranded nucleic acid scaffold is described in more detail, below.

a. Determination of the Node-Edge Network

In some embodiments, the wire-frame model of a desired polyhedral structure is rendered as a node-edge network. Typically, the nodes and edges of the network correspond to the vertices and lines of the polyhedron. In certain embodiments, a node-edge network corresponding to a structure can be represented by the planar graph of the corresponding polyhedron, or by other means. For example, in some embodiments the planar graph of the corresponding polyhedron is a Schlegel diagram. The Schlegel diagram is a projection of the desired polyhedral form from $R^d$ into $R^{d-1}$ through a point beyond one of its facets or faces. The resulting entity is a polytopal subdivision of the facet in $R^{d-1}$ that is combinatorially equivalent to the original polyhedral form. Formulas and methods for generating a Schlegel diagram of a polyhedral form are known in the art. In other embodiments, a node-edge network is calculated for a corresponding structure without the use of a planar graph.

Therefore, in some embodiments, the methods include the step of providing a node-edge network of the target structure. Typically, each of the vertices corresponds to a node in the network, and each line between any two vertices represents an edge in the network.

b. Creating a Spanning Tree

In some embodiments, the node-edge network is used to establish connectivity amongst all of the vertices. An exemplary representation of connectivity through the node-edge network is by producing one or more spanning trees. The spanning tree is the set of edges that connect all nodes within the network without circuits. In some embodiments, the spanning tree is determined using one or more formulas. Formulas for determining the spanning tree for a network are known in the art. An exemplary method for determining the spanning tree for the node-edge network corresponding to the desired shape is Prim's Formula. Therefore, in some embodiments, identifying scaffold routing includes creating one or more spanning trees for the node-edge network. In certain embodiments, the spanning tree is the spanning tree produced using a maximum-breadth search. If, as in this case, all edges are weighted the same, Prim's formula will generate a breadth-first search spanning tree, one with the most branches. Therefore, in some embodiments, identifying scaffold routing includes the selection of one or more spanning trees that have the most branches.

It has been shown that branching trees self-assemble more reliably than more linear trees, however, any spanning tree will provide a valid route.

c. Locating DX Crossovers

The methods include using the spanning tree to identify the route of the scaffold sequences through the target structure. For example, the methods can identify the location of anti-parallel DX cross-overs within the target structure by classifying each edge.

Determination of a spanning tree including all nodes of the network enables the identification of edges that are within the spanning tree and edges that are not within the spanning tree. Therefore, the methods include identifying edges that are within the spanning tree and edges that are not within the spanning tree. Edges within a spanning tree represent continuous stretches for the route of the single-stranded nucleic acid scaffold in both directions (i.e., 5'-3' and 3'-5'). Edges not within a spanning tree include anti-parallel DX cross-over motifs. Therefore, for each edge that is not in the spanning tree, a pair of pseudo-nodes is added to split the edge into two halves, each corresponding to one side of a scaffold crossover. At each anti-parallel DX cross-over motif, the single-stranded nucleic acid scaffold reverses the direction it travels along.

The methods include assigning anti-parallel DX cross-over motifs at the center of each edge that is not within a spanning tree. Because a single scaffold crossover is assigned to each edge that is not within a spanning tree, and edges with zero scaffold crossovers must connect to every vertex, there can be no cycles of edges with zero scaffold crossovers, meaning that there are V−1 edges with zero scaffold crossovers, where V is the number of vertices, and the rest have one scaffold crossover.

Locating the DX crossovers within each possible spanning tree corresponds to a unique scaffold routing.

d. Identification of the Euler Circuit

The path of the single-stranded nucleic acid scaffold is defined as the Euler Circuit of the node-edge network. Therefore, the methods include converting the spanning tree into an Eulerian circuit. Converting the spanning tree into an Eulerian circuit includes (1) adding a pair of pseudo-nodes to each edge that is identified as including a DX crossover; (2) adding a set of pseudo-nodes at each vertex in the graph, so that each edge is bounded on both ends by pseudo-nodes; (3) removing the original vertex nodes; and (4) defining the Eulerian circuit through which the continuous scaffold strand will be routed.

Typically, a vertex of degree N has N edges emerging from it. An Eulerian circuit is guaranteed when the degree of every vertex is even. Therefore, the methods include creating a scaffold route for which the degree of every vertex in the node-edge network is even. The Eulerian Circuit of the planar graph passes through each of the edges once in each direction.

Therefore, the Eulerian circuit defined by the methods passes twice along each edge of the spanning tree. The route of the scaffold strand identified by the methods ensure (1) the scaffold strand always enters a vertex from a first edge and exits the vertex from an adjacent edge that shares a face with the first edge; and (2) the scaffold strand does not enter and exit a vertex from the same edge. Therefore, the scaffold routing process produces only edges that are connected to the vertex. The scaffold routing process does not allow for the intersection of DNA strands. Therefore, the methods provide a scaffold route that does not include internal scaffold loops that are disconnected from the rest of the scaffold.

The subset of Eulerian circuit that defines the route of the single-stranded DNA scaffold sequence through the entire polyhedral structure is defined as the subset of Eulerian circuits known as A-trails.

The direction of the scaffold is chosen to run counter-clockwise around each face, so that for convex vertices (the majority of cage vertices) the major grooves of the duplexes at each vertex point inward to minimize electrostatic repulsion of the backbone. Therefore, the methods include converting the undirected graph into a directed graph to implement this directional choice.

e. Identifying Scaffold Routing for the Target Structure

Automated sequence design can be performed by first representing the target structure as a polyhedral mesh. Each edge is composed of multiple helices, so that the graph of the mesh is modified to represent these helices as multiple lines. These endpoints are then joined so that every duplex becomes part of a loop. By choosing a particular subset of these double crossovers, these discrete loops can connect to form one continuous Eulerian circuit through the entire structure, creating the scaffold routing. The spanning tree of this dual graph is then computed, and the edges that are members of the spanning tree correspond to the subset of crossovers required to complete the Eulerian circuit. Inverting the spanning tree of the dual graph back to the loop-crossover structure reveals the final scaffold routing. Therefore, the methods include converting the undirected graph into a directed graph to implement this directional choice.

f. Identifying the Sequence of the Single-Stranded Nucleic Acid Scaffold and Staple Sequences The methods include the identification of the nucleic acid sequences of staples corresponding to the sequence of the single-stranded nucleic acid scaffold.

The length of the scaffold sequence is determined from the Eulerian circuit calculated from the input geometry, modified according to the input size, for example, as determined by the user-defined size of one or more of the edges of the structure. Typically, the sequence of the scaffold is based on a template sequence, for example, a user-defined sequence, or a known sequence, such as a bacteriophage sequence (e.g., M13mp18). If the sequence length required to provide the desired structure according to the methods is smaller than that of the default sequence, a subset of the default sequence will be output. Alternatively, if the sequence length required to provide the desired structure according to the methods is larger than that of the default sequence, a sequence will be generated.

The methods include the placement of all staple sequences. After all the staples are placed, each staple is converted to a vector of numbers, each value corresponding to the scaffold nucleotide to which it is base paired. Then, the input or generated scaffold sequence is used, matching a base identity (A, T, G, or C) to a scaffold number. If no sequence is provided, a segment of M13pm18 is used by default if the required scaffold length is less than 7249 nucleotides, and a sequence is randomly generated if the required length is greater. The complementary nucleotide via Watson-Crick base pairing is then be computed and assigned to the corresponding staple nucleotides. Finally, this list of staple sequences is output for synthesis.

i. Orientation of Scaffold Sequence

The methods combine the user-defined desired size (i.e., edge-length) with the spanning tree and pseudo-node addition to determine a scaffold sequence.

The Eulerian circuit is used to identify a scaffold nick position. The scaffold is nicked at a position located on an edge without scaffold crossovers that is located on the duplex at a distance from the DX crossovers. Using Prim's formula, this edge will have Vertex #1 as one of its endpoints, since with the most-branching default all edges connected to Vertex #1 are members of the spanning tree. Marking this 5'-end as scaffold base #1, each of the scaffold bases are subsequently numbered with knowledge of the edge lengths and routing scheme, all while keeping track of their relative position on their edge.

The scaffold is designed to ensure that all staple and scaffold crossovers remain perpendicular to the helical axes. Therefore, the scaffold is designed to ensure the 5' end overhangs the 3'end by one nucleotide for each edge. The half-edges, namely those edges that are split by the scaffold crossover, have lengths that are pre-determined by some simplifying assumptions. The scaffold crossover is placed as close to the center as possible, with a convention set here to have a preference towards the lower-index vertex if needed. Therefore, the methods determine how long a particular section of a scaffold is on a given edge.

The methods ascribe two pieces of information to each nucleic acid base within the scaffold: (1) an index number to indicate its position on the scaffold strand; and (2) a set of numbers to indicate its spatial location, including the edge, the duplex, and the position from the 5' end.

Typically edges are numbered according to their order within the Eulerian circuit, starting from the position of the 5' nick.

ii. Placement of Staple Strands

The methods identify the routing of the staple strands based on the spatial location, including the edge, the duplex, and the position from the 5' end. For example, information contained within the set of numbers that indicate the spatial location, including the edge, the duplex, and the position from the 5' end, is used to identify which bases in the staples are paired with which bases in the scaffold, then the former index number is assigned to the staples accordingly.

Typically, the number of staple strands varies depending upon the complexity of the structure. For structures with small scaffold strands that are of minimal complexity, such as simple tetrahedra, cubes, etc., the number of staple strands is typically about 5, 10, 50 or more than 50. For longer scaffold strands (e.g., greater than 1500 bases) and/or more complex structures, the number of staple strands can be several hundreds to thousands. For example, in some embodiments, the number of staple strands is up to 50, 100, 300, 600, 1,000 or more than 1,000.

There are three categories of staple strands, each with their own prescribed pattern: staples on vertices, staples on edges with scaffold crossovers, and staples on edges without scaffold crossovers.

The methods include a minimum edge length of 31 bp. A 31/32-bp edge has 21 bp occupied by vertex staples, leaving 10 or 11 bp for edge staples. Therefore, in both types of edges, a 20- or 22-bp staple is placed with a single crossover on one side, because a staple nick in the middle would conflict with the scaffold crossover. Therefore, the methods include a double-crossover vertex staple design in any structure with a 31- or 32-bp edge present.

The pattern of staple routing depends on the degree of the vertex, ensuring that each staple length is 52- or 78-nucleotides (nt) long for ease of synthesis.

$$a = \begin{cases} 0, & \text{if } n \bmod 3 = 0 \\ 2, & \text{if } n \bmod 3 = 1 \\ 1, & \text{if } n \bmod 3 = 2 \end{cases} \quad \text{(Eq. 1)}$$

$$b = \frac{n - 2a}{3} \quad \text{(Eq. 2)}$$

Where
a is the number of 52-nt staples at the vertex,
b is the number of 78-nt staples at the vertex, and
n is the degree of the vertex.

(i). Staples on Vertices

The staples on vertices pair with the first 10-11 nucleotides of each duplex abutting the vertex, with poly-T bulges of length 5 crossing between edges. There are two varieties of vertex staple designs implemented: one system uses single crossovers in some places to ensure that there is 10-11 bp of continuous duplex for high specificity and binding strength, and the other, more traditional, system uses double crossovers everywhere, leading to a minimum of 5 bp of continuous duplex. For the structures synthesized and characterized in this work, the former paradigm is used, as the higher binding strength was found to create a more cooperative transition at a higher temperature (FIGS. 9A-9L). The pattern of staple routing depends on the degree of the vertex, ensuring that each staple length is 52- or 78-nucleotides (nt) long for ease of synthesis.

(ii). Staples on Edges with Scaffold Crossovers

The edge staples pair with the intermediate nucleotides between vertex staples. For the edges with scaffold crossovers, two 31-32-nt staples are placed across the scaffold crossover, together occupying a 15-16-nt region on either side of the crossover for sufficiently strong binding. The remainder of scaffold has 42-nt staples placed to create staple crossovers every 21 base pairs, with a 20- or 22-nt staple in the case of a 10- or 11-nt remainder.

(iii). Staples on Edges without Scaffold Crossovers

The edges without scaffold crossovers follow the same pattern, filling with as many 42-nt staples that can fit and using a 20- or 22-nt staple when necessary.

g. Output of Staple Sequences

The methods provide the nucleic acid sequences of staple strands corresponding to the desired target sequence, edge size(s) and optionally a template nucleic acid sequence.

After all the staples are placed according to the methods, each staple is a vector of numbers, each value corresponding to the scaffold nucleotide to which it is base paired. Then, the input or generated scaffold sequence is used, matching a base identity (A, T, G, or C) to a scaffold number.

If no sequence is provided, a default sequence is used. For example, in some embodiments, if the required scaffold length is less than 7249 nucleotides, a segment of M13pm18 nucleic acid sequence is used. In other embodiments, a sequence is randomly generated. The methods determine complementary nucleotides via Watson-Crick base pairing and assign sequences to the corresponding staple nucleotides. Typically, the methods produce this list of staple sequences as output. Therefore, in some embodiments the methods also include the step of synthesizing the staple sequences. In some embodiments the methods include the step of synthesizing the scaffold sequence. In some embodiments, the methods include the step of synthesizing scaffold sequence and the staple sequences. Therefore, the methods include converting the undirected graph into a directed graph to implement this directional choice.

h. Scaffold Sequence Output Based on User-Defined Staples

Methods to generate staple strand sequences given a scaffold sequence can be inverted, so that the user provides staple strand sequences that are used to generate a scaffold sequence.

The methods for custom-design of a nanostructure having desired geometric parameters can also be used to determine the nucleic acid sequence of a scaffold sequence that will fold into the desired shape based on hybridization with one or more user-defined staple sequences. Therefore, in some embodiments, the methods provide the nucleic acid scaffold sequence, based on the input of user-defined staple strands, desired target structure and optionally edge size(s).

The methods provide a custom scaffold sequence that based on user-defined staple sequences. Typically, the number and size of scaffold sequences that are required by the user will vary according to the desired geometry of the nanostructure. In some embodiments, at least one, two or three staple sequences are required as input. In certain embodiments, one or more staple sequences are required as input, and the methods provide the sequence(s) of one or more remaining, or undefined staple sequences.

2. Nanostructures with Parallel Crossover Motifs

In some embodiments, the methods require including at least one edge having one "PX" (parallel paranemic scaffold crossover) motif. Therefore, in some embodiments, there are two double helices per edge oriented in parallel vertically, that is, one of the duplexes is closer to the interior of the object than the other. In some embodiments, the scaffold cannot be an arbitrary sequence, because self-hybridization must occur to complete the structure. Self-hybridizing regions replace the need for staple strands, so in some embodiments one nucleic acid strand can fold and hybridize to itself to form an origami nanostructure without any other oligonucleotides.

The scaffold strand is routed by a method that identifies the Eulerian circuit through the entire network, such that the strand enters each vertex from a first edge and exits the vertex from an adjacent edge that shares a face with the first edge. The route of the scaffold strand is determined according to the rules that the scaffold strand does not enter and exit from the same edge, and the scaffold strand does not exit from an edge that is not-adjacent to the edge it enters. Therefore, the scaffold routing process does not allow for the intersection of DNA strands and the process produces only edges that are connected to the vertex.

Each of the steps involved in determining the route of the single-stranded nucleic acid scaffold is described in more detail, below.

a. Determination of the Node-Edge Network

In some embodiments, the wire-frame model of a desired polyhedral structure is rendered as a node-edge network. Typically, the nodes and edges of the network correspond to the vertices and lines of the polyhedron. In certain embodiments, a node-edge network corresponding to a structure can be represented by the planar graph of the corresponding polyhedron, or by other means. For example, in some embodiments the planar graph of the corresponding polyhedron is a Schlegel diagram. The Schlegel diagram is a projection of the desired polyhedral form from $R^d$ into $R^{d-1}$ through a point beyond one of its facets or faces. The resulting entity is a polytopal subdivision of the facet in $R^{d-1}$ that is combinatorially equivalent to the original polyhedral form. Formulas and methods for generating a Schlegel diagram of a polyhedral form are known in the art. In other embodiments, a node-edge network is calculated for a corresponding structure without the use of a planar graph.

Therefore, in some embodiments, the methods include the step of providing a node-edge network of the target structure. Typically, each of the vertices corresponds to a node in the network, and each line between any two vertices represents an edge in the network.

b. Creating a Spanning Tree

In some embodiments, the node-edge network is used to establish connectivity amongst all of the vertices. An exemplary representation of connectivity through the node-edge network is by producing one or more spanning trees. The spanning tree is the set of edges that connect all nodes within the network without circuits. In some embodiments, the spanning tree is determined using one or more formulas. Formulas for determining the spanning tree for a network are known in the art. An exemplary method for determining the spanning tree for the node-edge network corresponding to the desired shape is Prim's Formula. Therefore, in some embodiments, identifying scaffold routing includes creating one or more spanning trees for the node-edge network. In certain embodiments, the spanning tree is the spanning tree produced using a maximum-breadth search. If, as in this case, all edges are weighted the same, Prim's formula will generate a breadth-first search spanning tree, one with the most branches. Therefore, in some embodiments, identifying scaffold routing includes the selection of one or more spanning trees that have the most branches.

It has been shown that branching trees self-assemble more reliably than more linear trees, however, any spanning tree will provide a valid route.

c. Classifying Edges

The methods include using the spanning tree to classify the edges, culminating in the final Eulerian circuit the scaffold strand takes through the target structure.

There are four classifications the edges can have, based on choosing between two options for two traits. One trait is the crossover motif of the edge. Each edge can employ either anti-parallel (DX) or parallel (PX) crossovers. The second trait is determined by membership in the spanning tree. Edges that are members of the spanning tree must have each scaffold fragment, that is, the portion of the scaffold strand within the edge, start and end at different vertices. Edges that are not members of the spanning tree must have each scaffold fragment start and end at the same vertices. Note that this is an extension of the classification used for the two-helix-per-edge DX structures; the classifications and choice of scaffold crossover location follow the same start and end rules as described above.

d. Superimposing and Connecting Edges

Based on the classification (crossover motif, spanning tree membership) and the length of the edge, a set of scaffold fragments, and in some embodiments, staple strands, with routing within the edge already determined, is superimposed on the edge. In some embodiments, this is represented by an M×4 matrix, where M is the length of the edge, and each of the four columns represents one strand, e.g. Column 1 represents the nucleotides 3' to 5' from the vertex at the top to the vertex at the bottom in the duplex closer to the interior of the object, Column 2 represents the nucleotides 5' to 3' from the vertex at the top to the vertex at the bottom in the interior duplex, Column 3 represents the nucleotides 5' to 3' from the top vertex to the bottom vertex in the duplex closer to the exterior of the object for PX edges and 3' to 5' for DX edges, and Column 4 represents the nucleotides 3' to 5' from the top vertex to the bottom vertex in the exterior duplex for PX edges and 5' to 3' for DX edges. Nucleotides in Columns 1 and 2 are complementary via Watson-Crick base pairing, and nucleotides in Columns 3 and 4 are complementary in the same manner. Nucleotides in the same row are the same interpolated distance between the two vertices.

In some embodiments, the elements of the matrix determine the route of the scaffold and enforce the crossover motif; for PX edges, the major/minor groove pattern is also enforced. Elements that are consecutive in number, e.g., 4 and 5, or i and i+1, represent nucleotides that share a covalent phosphodiester bond, and elements that are in the same row and are in paired columns (1 and 2, 3 and 4) are base paired. For PX edges, the major/minor groove pattern is the number of bases that lie in the major and minor grooves of the double helix. In some embodiments, the number of bases in a major groove can be less than 5, 5, 6, 7, 8, 9, or more than 9, and the number of bases in a minor groove can be less than 4, 4, 5, 6, or more than 6. The major/minor groove pattern also determines where parallel crossovers can occur. In some embodiments, this is reflected in the matrix as when consecutive nucleotides are not in the same column, e.g. nucleotide 4 is in Column 1 and nucleotide 5 is in Column 4.

When all of the edges have been superimposed, the first and last rows of Columns 1 and 2 of each edge matrix represent the 5' and 3' ends that must be joined to neighboring edges at the vertex. The connection is enforced by updating each nucleotide's number to uniquely identify its position in the complete scaffold strand, maintaining that consecutive numbers indicate connection along the phosphodiester backbone.

e. Identifying the Sequence of the Single-Stranded Nucleic Acid Scaffold and Staple Sequences The methods include the identification of the nucleic acid sequences of scaffold and staples corresponding to the hybridization pattern set by the routing described above.

In regions of parallel crossovers, the sequence must be customized such that Watson-Crick base pairing is followed. In regions of anti-parallel crossovers, the scaffold sequence can be arbitrary, and the staple sequences that hybridize to it must follow Watson-Crick base pairing.

In some embodiments, the scaffold nick is chosen to be placed at the end of a farther-from-center duplex. This may be on PX or DX edge. The 5' end of the nick is marked as base #1, and the 3' end is the last base of the scaffold. Some scaffold nucleotides may be part of hairpin loops and do not have bases paired to them; the numbering of the scaffold strand remains unchanged, but these regions may be marked as single-stranded nucleic acid strands.

For these custom sequences, in some embodiments a random number generator choosing between 1 and 4 inclusive, which can map to A, C, G, T for DNA and A, C, G, U for RNA can produce the sequences of one member of each base pair, and its partner's sequence is found via canonical Watson-Crick base pairing. If certain staple sequences are to be incorporated, perhaps for example if they have been functionalized and need to bind to the larger origami structure, then those sequences of those regions are determined from the target staple sequences.

With this, the methods ascribe (1) an index number to indicate its position on the scaffold strand; and (2) a set of numbers to indicate its spatial location, including the edge, the duplex, and the position from the 5' end.

f. Placement of Staple Strands

In edges with anti-parallel crossovers, staples may be necessary to bring together the portions of scaffold within the edge. In some embodiments, the superimposed edges contain regions where the staples lie based on their numbers being non-consecutive with the rest of the bases in the edges. In this embodiment, vertex staples are not required because only one duplex from each edge meets at the vertex.

g. Output of Staple and/or Scaffold Sequences

The methods provide the nucleic acid sequences of scaffold and staple strands corresponding to the desired target edge size(s) and geometry. Unlike the embodiment that only contains DX motifs, the scaffold sequence is, in part or in whole, a custom sequence.

Based on the nucleotide sequences generated in the previous steps, the methods typically produce this list of staple sequences and scaffold sequence as output. Therefore, in some embodiments the methods also include the step of synthesizing the staple sequences. In some embodiments the methods include the step of synthesizing the scaffold sequence. In some embodiments, the methods include the step of synthesizing the scaffold sequence and the staple sequences.

C. Assembling Nucleic Acid Nanostructures

Typically, following design according to the described methods, the nucleic acid nanostructures are synthesized, folded and purified prior to structural validation. Therefore, methods for the design of nucleic acid nanostructures having a desired form optionally include the step of producing the nucleic acid nanostructure. In some embodiments, producing the nanostructure includes synthesizing nucleic acids having the sequence of the scaffold and staples according to the designed form; hybridizing the staple sequences to the scaffold; folding the nanostructure; purifying the nanostructure; performing structural analysis of the nanostructure; validating the structure; and combinations.

1. Production of Nucleic Acid Nanostructures

The methods provide the nucleic acid sequences of the single-stranded scaffold and the oligonucleotide staple sequences that can be combined to form complete three-dimensional nucleic acid nanostructures of a desired form and size. Typically, the methods convert the information provided as geometric parameters corresponding to the desired form and the desired dimensions into the sequences of oligonucleotides that can be synthesized using any means for the synthesis of nucleic acids known in the art.

a. Single-Stranded Scaffold DNA Sequence

Scaffold nucleic acid sequences and oligonucleotide staple sequences can be synthesized or purchased from numerous commercial sources. In some embodiments, the scaffold nucleic acid sequence is the M13mp18 single-stranded DNA scaffold. The M13mp18 ss DNA can be purchased from multiple commercial sources, including New England Biolabs (Cat # N4040S) or from Guild Biosciences for various M13mp18 size.

Typically, scaffold DNA of the desired length is produced using polymerase chain reaction (PCR) methodologies. Standard methods for PCR are known in the art. In some embodiments, the nucleic acid nanostructures are produced using asymmetric PCR (aPCR). When aPCR amplification is used, oligonucleotide primers can be designed to generate many different scaffold lengths. Therefore, in some embodiments, the scaffold having a desired length is produced using one or more custom oligonucleotides. When the template scaffold nucleic acid is known, a set of known oligonucleotides can be used. For example, when the scaffold nucleic acid is the M13mp18 ssDNA, the primers in Table 2 can be used to design scaffolds of desired lengths. In some embodiments modified dNTPs (examples of modified dNTPs include, but are not limited to dUTP, Cy5-dNTP, biotin-dNTPs, alpha-phosphate-dNTPs) are used for amplification of the ssDNA scaffold. In other embodiments the template use is the Lambda phage that can be purchased from different commercial sources, including New England Biolabs (Cat # N3011S). In other embodiments, the nucleic acid nanostructures are produced using digestion of the template DNA to form a scaffold nucleic acid of the desired length. In certain embodiments, a combination of PCR and digestion methods is used to produce scaffold single-stranded nucleic acid of the desired length.

When nucleic acid scaffold sequences are required to be synthesized, the scaffolds can be synthesized using the asymmetric PCR, for example, using GBLOCK® DNA commercially available from Integrated DNA Technologies as a template.

2. Assembly of Nanostructures

The methods include assembly of the single-stranded nucleic acid scaffold and the corresponding staple sequences into the nanostructure of the desired shape and size. Typically, the assembly is carried out by hybridization of the staples to the scaffold sequence. Therefore, in some embodiments, the nucleic acid nanostructures are assembled by DNA origami annealing reactions. For example, the oligonucleotide staples are mixed in the appropriate quantities in an appropriate reaction volume. In preferred embodiments, the staple strand mixes are added in an amount effective to maximize the yield and correct assembly of the nanostructure. For example, in some embodiments, the staple strand mixes are added in molar excess of the scaffold strand. In an exemplary embodiment, the staple strand mixes are added at a 10-20× molar excess of the scaffold strand.

Annealing can be carried out according to the specific parameters of the staple and scaffold sequences.

3. Purification of Nucleic Acid Nanostructures

The methods include purification of the assembled nucleic acid nanostructures. Purification separates assembled structures from the substrates and buffers required during the assembly process. Typically, purification is carried out according to the physical characteristics of nanostructures. For example, the use of filters and/or chromatographic processes (FPLC, etc.) is carried out according to the size and shape of the nanostructures.

In an exemplary embodiment, nucleic acid nanostructures are purified using filtration, such as by centrifugal filtration, or gravity filtration. In some embodiments, filtration is carried out using an Amicon Ultra-0.5 mL centrifugal filter (MWCO 100 kDa).

Following purification, nucleic acid nanostructures can be placed into an appropriate buffer for storage, and/or subsequent structural analysis and validation. Storage can be carried out at room temperature (i.e., 25° C.), 4° C., or below 4° C., for example, at −20° C. Suitable storage buffers include PBS, TAE-$Mg^{2+}$ or DMEM.

D. Predicting 3D Structure

Methods for designing nucleic acid nanostructures of a desired shape and size can include steps for validation of the resulting nucleic acid structure based on the output sequences. For example, in some embodiments, the methods also include the step of predicting the 3-dimensional coordinates of the nucleic acids within the nucleic acid nanostructure, based on the output of the system used for positioning scaffold and, when present, staple sequences. When structural information for a nucleic acid nanostructure is predicted, the predicted information can be used to validate the nucleic acid nanostructure. Typically, validation of the resulting nucleic acid structure includes (1) calculating the positions of each base pair in the structural model; (2) determining the positions of each base pair in the nucleic acid nanostructure; and (3) comparing the calculated structural data obtained for the model with that experimentally determined (i.e., observed) for the nanostructure.

1. In Silico Modelling of Structural Data

The 3-dimensional coordinates of a nucleic acid base pair can be calculated by any means known in the art. In a preferred embodiment, the positions of each base pair in the structural model are calculated using computational modelling. Therefore, in some embodiments, in silico modelling is used to predict the three-dimensional structural features of a polyhedral nucleic acid nanostructure designed from a target model according to the methods. The parameters used for modelling the 3-dimensional coordinates of a nucleic acid base pair of a given nanostructure designed according to the described methods are determined based upon the presence of antiparallel or parallel crossovers within the structure.

a. In Silico Modelling of Nanostructures Including Antiparallel Crossovers

In some embodiments, in silico modelling is used to predict the three-dimensional structural features of a polyhedral nucleic acid nanostructure including anti-parallel cross-overs, designed from a target model according to the described methods.

When in silico modelling is used to predict structural features of nucleic acid nanostructures including antiparallel crossovers, in silico modelling can be used to predict the position of each base pair in the structural model by interpolating between the two ends of the edge it resides on, and shifting away perpendicularly from the central axis by 10 Å, half the inter-helical distance for an anti-parallel crossover. The edge is assumed to lie in a plane with a normal vector defined by the sum of the unit normal vectors of the two neighboring faces. There are several ways to define the location of the ends of the edges. The DX-tile edges can be assumed to be two parallel cylinders with combined width 40 Å (20 Å inter-helical distance and 20 Å duplex diameter). This can be further simplified to a rectangle with width 40 Å, with the line of the edge serving as a central axis. In the ideal case, the corners of these rectangles meet, since the scaffold exits and enters the edge from these locations. The widths of the rectangles together would form an N-sided regular polygon, because they have the same sides and have equal angles between them. The perpendicular distance from the center of this polygon and an edge (the beginning of the interpolation) is the inradius of this polygon. From the inradius, the distance between the vertex and the beginning of the DX-tile edge is determined using the sum of the face angles. If the multi-arm DX-tile were flat, this would be equivalent to the inradius.

$$s = \frac{2\pi}{\theta_{tot}} r \quad \text{(Eq. 3)}$$

where s is the distance between the vertex and the beginning of the DX-tile edge, r is the inradius of the polygon formed by the widths of the tiles, and $\theta_{tot}$ is the sum of all face angles at the vertex.

For regular N-sided polygons, $$r = \frac{w}{2}\cot\left(\frac{\pi}{N}\right) \quad \text{(Eq. 4)}$$

where w is the combined width of the DX-tile (40 Å).

In some embodiments, in silico modelling is used to predict the co-ordinates of nucleic acids within structures whose edges do not meet at regular angles. Exemplary structures whose edges do not meet at regular angles include the Archimedean solids. In that case, depending on the convention used to define the length of the inradius, there will be backbone stretches or nucleotide overlaps. For the cuboctahedron, a representative Archimedean solid, the size of the object is best fit when backbone stretches are minimized, where the inradius is calculated based on the largest face angle.

$$r = \frac{w}{2}\cot\left(\frac{\theta_{max}}{2}\right) \quad \text{(Eq. 5)}$$

where $\theta_{max}$ is the largest face angle. Note that this general equation applies to regular N-sided polygons as well, since $\theta_{max}=2\pi/N$.

For structures with concave vertices, where $\theta_{tot}>2\pi$, to obey the convention that all edge axes meet at a single point, s=r is defined, creating a sphere of radius r that defines the edge boundaries.

b. In Silico Modelling of Nanostructures Including Parallel Crossovers Scaffold Sequence Output Based on User-Defined Staples In some embodiments, in silico modelling is used to predict the three-dimensional structural features of a polyhedral nucleic acid nanostructure having parallel crossover motifs, designed from a target model according to the described methods. For example, in silico modelling can be used to predict the position of each base pair in the structural model by interpolating between the two ends of the edge it resides on. If the base pair is part of the interior duplex of the edge, no shifting is necessary; if the base pair is part of the exterior duplex, the position is shifted away along the outward normal of the edge by 20 Å, the inter-helical distance. There are several ways to define the location of the ends of the edges, which are the 5' and 3' ends of the interior duplex. The interior duplex can be assumed to be a cylinder with diameter 20 Å. This can be further simplified to a rectangle with width 20 Å. In the ideal case, the corners of these rectangles meet at the vertex since the scaffold exits and enters the edge from these locations. The widths of these rectangles together would form an N-sided regular polygon, because they have the same sides and have equal angles between them. The perpendicular distance from the center of this polygon and an edge (the beginning of the interpolation) is the inradius of this polygon.

Calculating the inradius r and the distance between the vertex and the beginning of the interior duplex s follows the same procedure as described with Eq. 3 to 5, above, except w in this case is the diameter of a duplex, (e.g., 20 Å), instead of the width of a DX-tile (e.g., 40 Å).

2. Validation of Observed Structural Data

For validation, the predicted three dimensional model for a given structure is used as a comparison with the experimentally determined structural data. For example, the in silico prediction of structure(s) for a given input shape, size and optionally a nucleic acid sequence can be compared with actual structural data. Therefore, the methods can include the step of using data obtained by in silico modelling of a virtual structure to validate the structural parameters of a nucleic acid nanostructure designed and synthesized according to the methods. In certain embodiments, a virtual structure prepared by in silico modelling is used as a control for the design and synthesis methods.

Actual structural data corresponding to a nucleic acid nanostructure produced according to the methods can be obtained using any method known in the art. Exemplary methods for acquiring and analyzing biophysical data for macromolecular structures include X-ray crystallography, Nuclear Magnetic Resonance (NMR), Cryo-electron microscopy, Atomic Force Microscopy, Light Microscopy, Small-angle X-ray diffraction, Circular Dichroism, Analytical Ultracentrifugation, chromatographic methods, and combinations.

In some embodiments, differences between the in silico prediction of structural features and actual structural features identify structural deviations, etc.

III. Systems

A. Computer Implemented Systems

The systems and methods provided herein are generally useful for predicting the design parameters that produce a nucleic acid nanostructure having a desired polyhedral shape. In some embodiments, the geometric parameters corresponding to the desired form and the desired dimensions are input using a computer-based interface that allows for the design process to be carried out in a completely in-silico manner. For example, in certain embodiments, the methods are implemented in computer software, or as part of a computer program that is accessed and operated using a host computer. In other embodiments, the methods are implemented on a computer server accessible over one or more computer networks.

FIG. 1 depicts the work flow of methods that can be implemented. In some embodiments a user accesses a computer system that is in communication with a server computer system via a network, i.e., the Internet or in some cases a private network or a local intranet. One or both of the connections to the network may be wireless. In a preferred embodiment the server is in communication with a multitude of clients over the network, preferably a heterogeneous multitude of clients including personal computers and other computer servers as well as hand-held devices such as smartphones or tablet computers. In some embodiments the server computer is in communication, i.e., is able to receive an input query from or direct output results to, one or more laboratory automation systems, i.e., one or more automated laboratory systems or automation robotics that automate biochemical assays, PCR amplification, or synthesis of PCR primers. See for example automated systems available from Beckman Coulter.

The computer server where the methods are implemented may in principle be any computing system or architecture capable of performing the computations and storing the necessary data. The exact specifications of such a system will change with the growth and pace of technology, so the exemplary computer systems and components should not be seen as limiting. The systems will typically contain storage space, memory, one or more processors, and one or more input/output devices. It is to be appreciated that the term "processor" as used herein is intended to include any processing device, such as, for example, one that includes a CPU (central processing unit). The term "memory" as used herein is intended to include memory associated with a processor or CPU, such as, for example, RAM, ROM, etc. In addition, the term "input/output devices" or "I/O devices" as used herein is intended to include, for example, one or more input devices, e.g., keyboard, for making queries and/or inputting data to the processing unit, and/or one or more output devices, e.g., a display and/or printer, for presenting query results and/or other results associated with the processing unit. An I/O device might also be a connection to the network where queries are received from and results are directed to one or more client computers. It is also to be understood that the term "processor" may refer to more than one processing device. Other processing devices, either on a computer cluster or in a multi-processor computer server, may share the elements associated with the processing device. Accordingly, software components including instructions or code for performing the methodologies of the invention, as described herein, may be stored in one or more of the associated memory or storage devices (e.g., ROM, fixed or removable memory) and, when ready to be utilized, loaded in part or in whole into memory (e.g., into RAM) and executed by a CPU. The storage may be further utilized for storing program codes, databases of genomic sequences, etc. The storage can be any suitable form of computer storage including traditional hard-disk drives, solid-state drives, or ultrafast disk arrays. In some embodiments the storage includes network-attached storage that may be operatively connected to multiple similar computer servers that comprise a computing cluster.

1. Preparation of Nanostructure Libraries

In some embodiments, nanostructure libraries are designed by automated methods. Automated design programs for generating DNA nanostructures allow for a diverse set of geometries to be made, towards the synthesis of a library of objects for applications as diverse as nanocasting, delivery, and structural scaffolding. Libraries of DNA nanostructures with diverse sequences and geometries are also useful for diverse applications in memory storage, biomaterials synthesis, controlled nanoscale bioreactors, excitonic materials discover, vaccine development, and therapeutic delivery including cancer immunotherapy. For example, in some embodiments, a library or libraries of nucleic acid nanostructures can be constructed with single-strand bait sequences complementary to one or more target molecules. In an exemplary embodiment, the single-strand bait sequences include sequences that are complementary to one or more loops of a target RNA.

a. Hi-Throughput Production of Nanostructures and Modifications

Systems for the generation of libraries of nanostructures including different modifications can be implemented using automated methods. For example, the methods can provide the sequences of short single-stranded oligonucleotides staple strands of approximately 10-1,000 nucleotides that include "bait" sequences that are complementary in sequence to a region, or regions of a target molecule. In some embodiments the target molecules include RNAs, DNAs, PNAs, LNAs, proteins, lipids, carbohydrate, small molecules, etc. In an exemplary embodiment, the target molecule is a ribonucleic acid. Typically, target molecules interact with bait sequences on nanostructures via covalent or non-covalent linkage to the bait sequence. Exemplary linkages include either chemical conjugation via nucleic acid overhangs with click chemistry/other groups, or hybridization forces. When these staple strands are incorporated into the nanostructures, their position is defined by the design as part of the formation of the nanostructure, where the 5' end of the staple meets the 3' end of itself or another staple. Therefore, methods for creating libraries of polyhedral nucleic acid nanostructures for capturing one or more target molecules are provided. In some embodiments, the in silico design of polyhedral nucleic acid nanostructure libraries includes defining ranges for the desired properties of nanostructures within the library pool. Exemplary input ranges include minimum and maximum values for values such as size, vertex geometry, as well as spatial arrangement, and sequence diversity of bait sequences for capturing target molecules.

Figure 13:
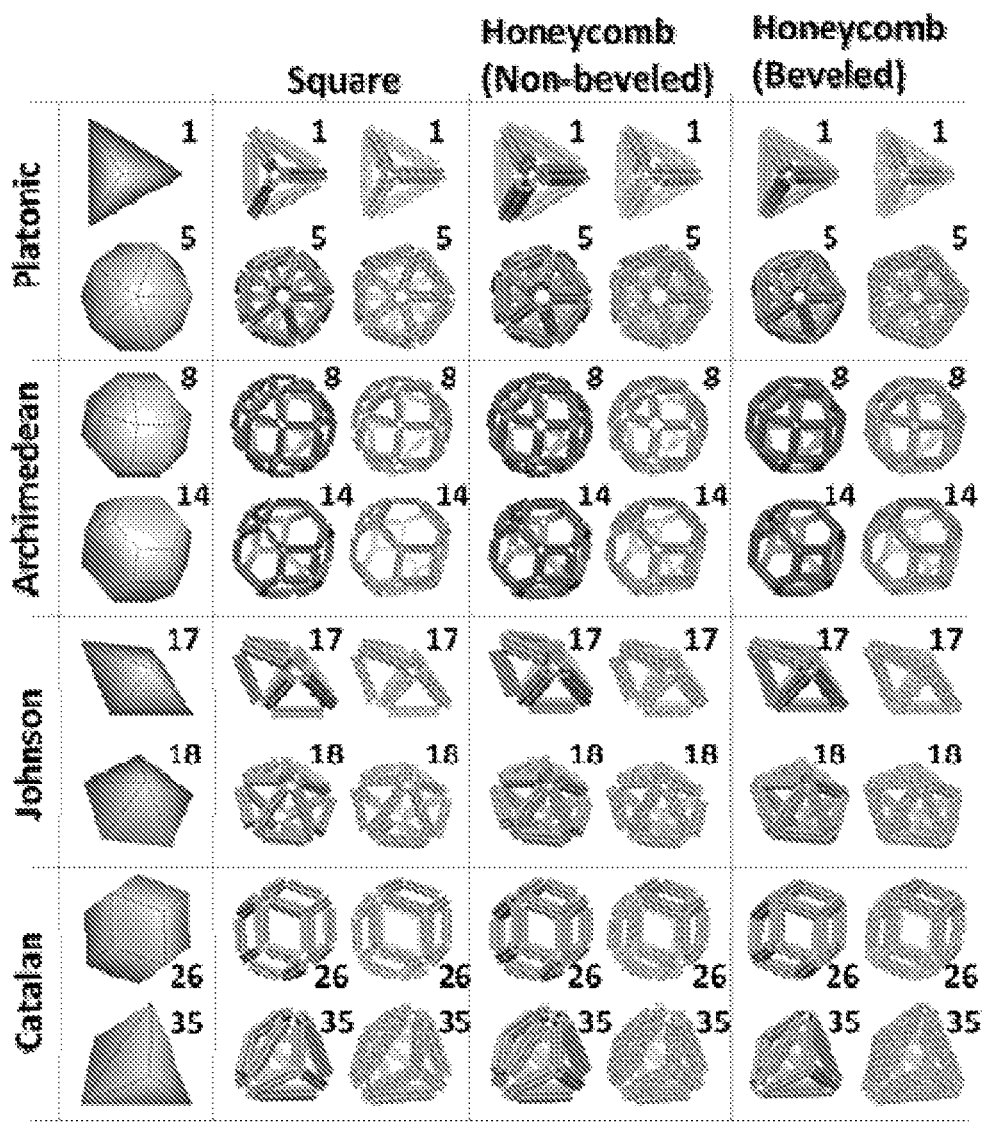
FIG. 13 is a chart representing a collection of face-shaded models of geometric input into formula, and the corresponding molecular models of nucleic acid nanostructures having either 2 by 2 square cross-sectional edges, honeycomb (non-beveled) cross-sectional edges, or honeycomb (beveled) cross-sectional edges for each of two Platonic (1, 5), two Archimedean (8, 15), two Johnson (17, 18), and two Catalan (26, 35) polyhedra, respectively, generated using top-down design procedures. Objects are not drawn to scale. Ribbon and space-filling cartoons are shown for each model.

Typically, computational systems are applied to automate sequence designs of a diverse set of DNA nanostructures. DNA nanostructures vary in many ways, including in object geometry (as shown in FIG. 2A and FIG. 13), edge lengths between vertices, staple nick positions along each edge (including nicks either inwardly facing or outwardly facing from the object), bait sequence orientation on the object (into or out from the edge tile), and the set of bait sequences for capturing the RNA. Different types of edges can provide distinct orientations of bait sequences. Alternative structured DNA assemblies include bricks, bricks with holes or cavities, assembled using DNA duplexes packed on square or honeycomb lattices (Douglas et al., Nature 459, 414-418 (2009); Ke Y et al., Science 338: 1177 (2012)). Paranemic-crossover (PX)-origami, in which the nanostructure is formed by folding a single long scaffold strand onto itself, can alternatively be used, provided bait sequences are still included in a site-specific manner. Further diversity can be introduced such as using different edge types, including 6-, 8-, 10, or 12-helix bundle. Further topology such as ring structure is also useable for example a 6-helix bundle ring.

Generally, the object geometry, edge length, and sequence topology dictate the scaffold and core staples, which are staple strands found in each class of nanostructure but are not functionalized in the library.

Generally, the high-throughput library generation of structured DNA origami assemblies is achieved via multiple automated steps. Automated design program for generating DNA nanostructures allows for a diverse set of geometries to be made (FIG. 2A and FIG. 13), towards the synthesis of a library of objects for applications as diverse as nanocasting, delivery, and structural scaffolding.

In some embodiments, a computational approach to generate a set of geometric objects with specific 3D overhangs complementary to single-stranded loops of HIV RNAs, seeking maximum coverage of Euclidian space by the overhangs, to allow for the most number of objects to be tested while being experimentally practical. The number of geometric objections generated in silico is about $10^5$, $2\times10^5$, $3\times10^5$, $4\times10^5$, $5\times10^5$, $6\times10^5$, $7\times10^5$, $8\times10^5$, $9\times10^5$, $10^6$, $10^7$, or more than $10^7$.

In some embodiments, the object generation approach is automated to attain maximum spatial coverage of the right size order of the overhangs in the fewest possible objects, limiting redundancy of spatial coordination. In some embodiments, a wide diversity of objects is used to ensure maximal coverage across the space of possibilities, such that the final experimental library has near complete spatial coverage.

In preferred embodiments, automated liquid handlers are used for generating these structure mixes. Typically, three high-throughput liquid dispensing steps are used for library generation, involving dispensing of the nucleic acid scaffold, the core staples, and the functionalized staple sequences into designated wells of any suitable multi-well plates.

Generally, automation is preferred for the nanostructure library generation. Using synthesized stocks of staples, in combination with automated liquid handling and a liquid dispenser such as Echo 555 nanofluidic dispenser, high-throughput combinatorial libraries of staples with scaffold are readily generated. Typically, for each structure, there are a scaffold strand and a set of core (i.e. non-functionalized) staples. First, the scaffold and core staples are dispensed to every well of any suitable multi-well plates. Any nano-droplet dispensers having the ability to rapidly dispense 0.5 nL to 100 nL from a source well to a destination well, can be used. In preferred embodiments, an Echo 555 nano-droplet dispenser is used, with the ability to rapidly dispense 2.5 nL from a source well to a destination well.

In some embodiments, the source well contains functionalized oligonucleotide staples at a concentration at about 100 nM, 200 nM, 300 nM, 400 nM, 500 nM, 600 nM, 700 nM, 800 nM, 900 nM, 1 mM, or more than 1 mM. For example, in certain embodiments, 2.5 nL of functionalized oligonucleotide staples is transferred from a source well containing functionalized oligonucleotide staples at a concentration at more than 1 mM. For example, the Echo 555 nano-droplet dispenser is capable of transferring up to 60 droplets per second at a volume of about 2.5 nL.

Using the nano-droplet dispenser system, multiple 384-well plates of distributions of objects are readily generated from a source plate of functionalized staple strands that cover the geometric space allowable by DNA origami objects. The methodology is not limited to 384-well plates, any suitable plates that are compatible with high-throughput capability can be used, for example, 96-well plates, 384-well plates, and 1536-well plates. In some embodiments, the concentrations and volume requirement of the nucleic acid scaffold, the core staples, and the functionalized staple strands are taken into consideration when deciding on the plate format.

In some embodiments, the nucleic acid scaffold, the core staples, and the functionalized staple strands are mixed and annealed by slowly changing the temperature down (annealing) over the course of 1 to 48 hours. This process allows the staple strands to guide the folding of the scaffold into the final DNA nanostructures. In further embodiments, high-throughput thermocyclers are used to slowly anneal staples and scaffold to generate the target nanostructure library, resulting in six, seven, eight, nine, ten, or more than ten 384-well plates of objects, with maximized utility generated from the computational method. In preferred embodiments, more than ten 384-well plates of nanostructures are generated.

The high-throughput methods allow fast generation so any number of nanostructures is capable of being generated as desired for the library, for example, one thousand, two thousand, three thousand, four thousand, five thousand, six thousand, seven thousand, eight thousand, nine thousand, ten thousand, twenty thousand, thirty thousand, forty thousand, fifty thousand, one hundred thousand, one million, and more than one million nanostructures for assembly. In preferred embodiments, combinatorial libraries of objects with any geometry, size, sequence, and nick placement, allowing for one million, or more than one billion of spatial overhang possibilities.

In some embodiments, liquid handling automation is used to generate approximately 3,000 of these space-covering geometric objects to test against target RNAs. In some embodiments, structural features and thermal stability of these target RNAs are characterized. In further embodiments, detection assays of nanostructure folding and stability using quantitative PCR, high-throughput fast analysis gels, and digestion analysis are used for assessing the DNA nanostructures as well as complexes with RNAs.

In some embodiments, the generated objects have designed staples with 3' or 5' single-stranded DNA overhangs distributed over the edges of the wireframe polyhedra with singular bait sequence occurrences per object design per well. In further embodiments, these bait sequences are tested for complementarity within the structure to reduce misfolding.

In some embodiments, the development of chip and single-well technologies in DNA synthesis of oligonucleotides allows for assembly of nanoscale objects having pools of different sets of staples in each well grown in, for example, a 384-well plate. In each case, purification techniques applied to single structures are applicable to this high-throughput system, typically via filtration and buffer exchange. In further embodiments, high-throughput, rapid-run gel based assays, selective cryo-EM structural studies, and quantitative PCR (qPCR) temperature melting analysis are used for structural analysis, and validation. Additionally, fluorimetric or colorimetric read-outs are feasible using strand-displacement reaction cascades or triggered amplification upon RNA complexing. In some embodiments, structure-specific bar-codes or affinity capture tags are included within the scaffold or staple sequences. These tags or codes are used to record and identify desired characteristics, or to select specific nanostructures, or molecules complexed with the nanostructures.

B. Graphical User Interface

In a preferred set of embodiments the computer server receives input submitted through a graphical user interface (GUI). The GUI may be presented on an attached monitor or display and may accept input through a touch screen, attached mouse or pointing device, or from an attached keyboard. In some embodiments the GUI will be communicated across a network using an accepted standard to be rendered on a monitor or display attached to a client computer and capable of accepting input from one or more input devices attached to the client computer. In other embodiments, a phone interface can identify, read and or run entered sequences.

In the exemplary embodiment, the GUI contains a target structure selection region where the user selects the parameters to be input. In this exemplary system a target structure is indicated by clicking, touching, highlighting or selecting one of the structures, or subsets of structures, that are listed. In preferred embodiments, the target structure is selected from a drop-down list. In some embodiments, the overall target structure is selected and then customized to include user-defined features. Customization may include drawing a model, such as a wireframe model, using any computer programs capable of such functions. Other parameters relating to the target structure, such as edge length, molecular weight, overall size, encapsulation volume, wire-frame model topology, etc.

In some embodiments, the GUI enables entering or uploading one or more template or guide sequences, such as nucleic acid sequences. For example, the GUI typically includes a text box for the user to input of one or more parameters. In other embodiments, users may input any sequence or sequences for which they would like to design staple primers. The GUI may additionally or alternatively contain an interface for uploading a text file containing one or more query structures and/or sequences.

In a particular embodiment, a text file contains the geometric parameters of a target shape provided in a standard polyhedral file format. The geometric parameters of any closed, orientable surface network can serve as input using any file format that specifies polygonal geometry known in the art, including but not limited to, Polygon File Format (PLY), Stereolithography (STL), or Virtual Reality Modeling Language (WRL). When a standard polyhedral file format is provided, the code includes a parser to convert the standard polyhedral files into the required inputs.

In embodiments that include both options, the GUI may also contain radio buttons that allow the user to select if the target sequence will be entered in a text box or uploaded from a text file. The GUI may include a button for choosing the file, may allow a user to drag and drop the intended file, or other means of having the file uploaded. Any of the parameters can be entered by hand to further customize.

The GUI also typically includes an interface for the user to initiate the methods based on the input model and/or other parameters. The exemplary GUI embodiment includes a submit button or tab that when selected initiates a search according to the user entered or default criteria. The GUI can also include a reset button or tab when selected removes that user input and/or restores the default settings.

The GUI will in some embodiments have an example button that, when selected by the user, populates all of the input fields with default values. The option selected by the example values may in some embodiments coincide with an example described in detail in a tutorial, manual, or help section. The GUI will in some embodiments contain all or only some of the elements described above. The GUI may contain any graphical user input element or combination thereof including one or more menu bars, text boxes, buttons, hyperlinks, drop-down lists, list boxes, combo boxes, check boxes, radio buttons, cycle buttons, data grids, or tabs.

IV. Nucleic Acid Nanostructures

Nucleic acid nanostructures, designed according to the geometric parameters of a desired polyhedral shape, according to the methods for top-down design of polyhedral nucleic acid assemblies are described. The polyhedral nucleic acid assemblies include a single-stranded nucleic acid scaffold sequence that is routed throughout the entire structure. The polyhedral nucleic acid assemblies optionally include oligonucleotide staple strands that hybridize to the scaffold sequence and create the polyhedral structure. When the polyhedral nucleic acid assemblies do not include staple strands, the scaffold sequence hybridizes to itself to create the polyhedral structure. The nucleic acids nanostructures designed according to the described methods include two or more nucleic acid duplexes per edge, and incorporate at least one parallel or anti-parallel crossover motif within at least one edge.

Modified nucleic acid nanostructures are also described. The nucleic acid nanostructures designed and assembled according to the described methods can include one or more modified nucleic acids, such as non-naturally occurring nucleic acids, derivatives and analogs. In some embodiments, the polyhedral structures are modified nucleic acid nanostructures that include one or more non-nucleic acid molecules. In other embodiments, the polyhedral structures are modified to include one or more nucleic acid sequences that are capable of binding or otherwise interacting with one or more non-nucleic acid molecules.

A. Nanostructure Assemblies Produced by Top-Down Design

Nucleic acid nanostructures having polyhedral morphology designed and produced according to the described top-down design methods are described. The polyhedral top-down design methods are described. The polyhedral nucleic acid nanostructures include a single stranded nucleic acid scaffold routed through the entire polyhedral structure.

The nucleic acid nanostructures can be of any desired shape that can be rendered as a three-dimensional wireframe mesh with sharp angles and non-curved edges. The nucleic acid nanostructures include a single-stranded nucleic acid scaffold that is routed throughout the entire structure. The route of the single-stranded nucleic acid scaffold throughout every face of the structure is the Eulerian circuit through the node-edge network of the planar graph of the structure. Preferably, the Eulerian circuit that defines the path of the single-stranded scaffold sequence throughout the entire structure is the A-trail Eulerian circuit.

In some embodiments, the nanostructures include at least one edge having a DX crossover motif located within the center of the edge. In other embodiments, the nanostructures include at least one edge having a PX crossover motif located within the center of the edge. Typically, the nanostructures include zero or one scaffold crossover structures per edge. The placement of DX scaffold cross-overs is defined using by the maximum-breadth spanning-tree of the node-edge network of the planar graph of the structure. Edges that form part of the maximum-breadth spanning tree are the only edges that do not include a DX scaffold crossover. Edges that form part of the maximum-breadth spanning tree are the only edges that include a single DX scaffold crossover.

Nucleic acid nanostructures produced according to the methods include two nucleic acid anti-parallel helices along each edge to strengthen the rigidity of the structure.

The nucleic acid nanostructures are typically less than 1 micron in diameter, for example, 10 nm-1,000 nm, inclusive. In some embodiments, the nucleic acid nanostructures have overall dimensions of 50-500 nm, 60-200 nm, or 60-100 nm, for example, 60 nm, 70 nm, 80 nm, 90 nm, 100 nm or leger than 100 nm. The molecular weight of the nanostructure is typically defined by the size and complexity of the polyhedral shape of the nanostructure. Typically, the nucleic acid nanostructures have a molecular weight of between 200 kilo daltons (kDa) and 1 mega dalton (1 mDa). The volume encapsulated by the nanostructures is defined by the size and shape of the nanostructures, and can be determined from the dimensions.

Typically the nucleic acid nanostructures are stable in physiological concentrations of salt, for example, in PBS, and DMEM.

1. Modified Nucleotides

In some embodiments, the nucleotides of the scaffolded DNA sequences are modified. For example, in some embodiments, one or more of the nucleotides of the DNA staple sequences are modified, or one or more of the nucleotides of scaffold sequence are modified, or both nucleotides in the DNA staple sequences and nucleotides in the scaffold sequence are modified.

When modified nucleotides are incorporated into nucleic acid scaffold strands or oligonucleotide staple strands, the modified nucleotides can be incorporated as a percentage or ratio of the total nucleotides used in the preparation of the nucleic acids. In some embodiments, the modified nucleotides represent 0.1% or more than 0.1% of the total number of nucleotides in the sequence, up to or approaching 100% of the total nucleotides present. For example, the relative amount of modified nucleotides can be between 0.1% and 100% inclusive, such as 0.1%-0.5%, 1%-2%, 1%-5%, 1%-10%, 10%-20%, 20%-30%, 30%-40%, 40%-50%, or more than 50% of the total, up to and including 100%, such as 60%, 70%, 75%, 80%, 85%, 90%, 95% or 99% of the total. In a certain embodiment, a sequence of nucleic acids includes a single modified nucleotide, or two, or three modified nucleotides. In some embodiments, nucleic acid nanostructures contain one, or more than one, up to 100 modified nucleotides in every edge. In other embodiments, the number of modified nucleotides correlates with the size of the nanostructure, or the shape, or the number of faces or edges, or vertices of the nanostructure. For example, in some embodiments, nucleic acid nanostructures include the same or different numbers of modified nucleotides within every edge or vertex. In some embodiments, the modified nucleotides are present at the equivalent position in every structurally-equivalent edge of the nanostructure. In some embodiments, nucleic acid nanostructures include modified nucleotides at precise locations and in specific numbers or proportions as determined by the design process. Therefore, in some embodiments, nucleic acid assemblies include a defined number or percentage of modified nucleotides at specified positions within the structure. In some embodiments, nucleic acid nanostructures produced according to the described methods include more than a single type of modified nucleic acid. In exemplary embodiments, nucleic acid nanostructures include one type of modified nucleic acid on every edge, or mixtures of two or more different modified nucleic acids on every edge. Therefore, when a single type of modified nucleic acid is present at an edge of the structure, each edge can include a different type of modification relative to every other edge.

Examples of modified nucleotides that can be included within the described nanostructures include, but are not limited to, diaminopurine, $S^2T$, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxy succinimide esters (NHS).

In some embodiments phosphorothioate modified backbone on the DNA nucleotide staples or on the scaffold is used to improve stability of the DNA nanostructures to degradation by exonuclease. For example, in some embodiments the nucleic acid nanostructures include modified nucleic acids that protect one or more regions of the nanostructure from enzymatic degradation or disruption in vivo. In some embodiments, nucleic acid nanostructures include modified nucleic acids at specific locations within the structure that direct the timing of the enzymatic degradation of specific parts of the structure. For example, modifications can be designed to prevent degradation, or to enhance the likelihood of degradation of one or more edges before or after different edges within the same structure. In this way, modifications that enhance or reduce protection or enzymic degradation of one or more parts of a nanostructure in vivo can drive or facilitate structural changes in the structure, for example, for example to enhance or alter the half-life of a given structure in vivo.

Locked nucleic acid (LNA) is a family of conformationally locked nucleotide analogues which, amongst other benefits, imposes truly unprecedented affinity and very high nuclease resistance to DNA and RNA oligonucleotides (Wahlestedt C, et al., *Proc. Natl Acad. Sci. USA,* 975633-5638 (2000); Braasch, D A, et al., *Chem. Biol.* 81-7 (2001); Kurreck J, et al., *Nucleic Acids Res.* 301911-1918 (2002)). In some embodiments, the nucleic acids are synthetic RNA-like high affinity nucleotide analogue, locked nucleic acids. In some embodiments, the scaffolded DNAs are locked nucleic acids. In other embodiments, the staple strands are locked nucleic acids.

Peptide nucleic acid (PNA) is a nucleic acid analog in which the sugar phosphate backbone of natural nucleic acid has been replaced by a synthetic peptide backbone usually formed from N-(2-amino-ethyl)-glycine units, resulting in an achiral and uncharged mimic (Nielsen P E et al., *Science* 254, 1497-1500 (1991)). It is chemically stable and resistant to hydrolytic (enzymatic) cleavage. In some embodiments, the scaffolded DNAs are PNAs. In other embodiments, the staple strands are PNAs.

In some embodiments PNAs, DNAs, RNAs, or LNAs are used for capture, or proteins or other small molecules of interest to target, or otherwise interact with complementary binding sites on structured RNAs, or DNAs. In other embodiments, a combination of PNAs, DNAs, RNAs and/or LNAs is used in the formation of structured nucleic acid nanostructures.

In some embodiments, the structured nanostructures include a combination of PNAs, DNAs, and/or LNAs. In some embodiments, a combination of PNAs, DNAs, and/or LNAs is used for the staple strands.

In some embodiments, the nucleic acids produced according to the described methods are modified to incorporate fluorescent molecules. Exemplary fluorescent molecules include fluorescent dyes and stains, such as Cy5 modified CTP.

In some embodiments, nucleic acid nanostructures include one or more nucleic acids conjugated to polymers. Exemplary polymers that can be conjugated to nucleic acids include biodegradable polymers, non-biodegradeable polymers, cationic polymers and dendrimers. For example, a non-limiting list of polymers that can be coupled to nucleic acids within the nucleic acid nanostructures includes poly (beta-amino esters); aliphatic polyesters; polyphosphoesters; poly(L-lysine) containing disulfide linkages; poly (ethylenimine) (PEI); disulfide-containing polymers such as DTSP or DTBP crosslinked PEI; PEGylated PEI crosslinked with DTSP; Crosslinked PEI with DSP; Linear SS-PEI; DTSP-Crosslinked linear PEI; branched poly(ethylenimine sulfide) (b-PEIS). Typically, the polymer has a molecular weight of between 500 Da and 20,000 Da, inclusive, for example, approximately 1,000 Da to 10,000 Da, inclusive. In some embodiments, the polymer is ethylene glycol. In some embodiments, the polymer is polyethylene glycol. In an exemplary embodiment, one or more polymer are conjugated to the nucleic acids within one or more of the staples. Therefore, in some embodiments, one or more types of polymers conjugated to staple strands are used to coat the nucleic acid nanostructure with the one or more polymers. In some embodiments, one or more types of polymers conjugated to nucleic acids in the scaffold sequence are used to coat the used to coat the DNA nucleic acid nanostructure with the one or more polymers.

2. Modified Nanostructures

Nucleic acid nanostructures designed and produced according to the described methods can be modified to include nucleic acids having a known function, or molecules other than nucleic acids. Exemplary additional elements include small molecules, proteins, peptides, nucleic acids, lipids, saccharides, or polysaccharides. For example, nucleic acid nanoparticles can be modified to include proteins or RNAs having a known function, such as antibodies or RNA aptamers having an affinity to one or more target molecules. Therefore, the nucleic acid nanostructures designed and produced according to the described methods can be functionalized nucleic acid nanostructures.

Nucleic acid nanostructures can include one or more functional molecules at one or more locations on or within the structure. In some embodiments, the functional group is located at one or more staple strands. In other embodiments, the functional moiety is located directly within the scaffold sequence of the nanostructure. In other embodiments, nanostructures include one or more functional moieties located within the scaffold sequence and within one or more staple sequences. When nanostructures include two or more functional moieties, the functional moieties can be the same, or different.

a. Interaction with Functional Molecules

Typically, nucleic acid nanostructures are modified by chemical or physical association with one or more functional molecules. Exemplary methods of conjugation include covalent or non-covalent linkages between the nanostructure and the functional molecule. In some embodiments, conjugation with functional molecules is through click-chemistry. In some embodiments, conjugation with functional molecules is through hybridization with one or more of the nucleic acid sequences present on the nanostructure. In some embodiments, conjugation with functional molecules is through click-chemistry.

i. Modified Staple Sequences

In some embodiments, nucleic acid nanostructures include one or more functional groups located at one or more staple strands. For example, in some embodiments, the nucleic acid nanostructures include modified staple strands include single-stranded overhang sequences. In some embodiments, the overhang sequences are between 4 and 60 nucleotides. In preferred embodiments, the overhang sequences are between 4 and 25 nucleotides. In some embodiments, the overhang sequences contain 4, 5, 6, 7, 8, 9, 10, 11, 12, 13, 14, 15, 16, 17, 18, 19, 20, 21, 22, 23, 24, 25, 30, 35, 40, 45, 50 nucleotides in length.

In some embodiments, nanostructures include oligonucleotide staples extended at either the 5' or 3' ends by an unpaired region of nucleic acid, such as DNA, RNA, PNA, or LNA of known sequence. For example, in some embodiments the single-stranded nucleic acid includes a binding site for one or more functional moieties, such as nucleic acids, proteins or small molecules. Therefore, nucleic acid nanoparticles including staple strands extended to include one or more single-stranded nucleic acid binding sites for a functional nucleic acid, protein or small molecule are described. Nucleic acid nanoparticles including functional RNA, small molecules, or proteins are also described. The functionalized nanoparticles can include functional moieties displayed at the surface of the nanoparticle, or located within the inner volume of the nanoparticle. Typically, the location of the functional moiety is determined by the desired biological function of the nanoparticle.

Nucleic acid nanoparticles functionalized with one or more nucleic acid or non-nucleic acid moieties having a known biological function are provided.

In some embodiments, nucleic acid nanoparticles include staple strands extended to include one or more single-stranded nucleic acid sequences that are complementary to the loop region of an RNA, such as an mRNA. Loop regions of mRNA targets can be identified using methods known in the art. When sequences complementary to these loop regions are appended to one or more nanoparticle staple strands, the nanoparticle is capable of capturing the target RNA. Nanoparticles specifically bound to target RNA can be identified from those that are not bound to the target RNA using any assay known in the art, such as by gel mobility shift, and/or imaging by cryo-EM.

ii. Modified Scaffold Sequences

In some embodiments, nucleic acid nanostructures include a single-stranded scaffold nucleic acid sequence that is modified to include one or more sequences of nucleic acids that bind one or more functional moieties, such as nucleic acids, proteins or small molecules. In some embodiments, the scaffold includes an overhang sequence that includes one or more functionalizing sequences or moieties at the 5' or 3' ends. In other embodiments, the scaffold includes an internal functionalizing sequence or moiety, for example, within one or more nucleic acids that form part of an edge of the nanostructure.

iii. Encapsulation or Structural Enclosure

In some embodiments, nucleic acid nanostructures are designed to have a shape or three dimensional form that encloses a volume suitable to contain one or more functional molecules. For example, in some embodiments, the nanostructures are designed to have the shape of a cup, box, vase or other open structure enclosing a volume, into which one or more functional molecules can be loaded or inserted. In some embodiments, insertion or loading of functional molecules to within the inner space of the nucleic acid nanostructure is directed through the presence of capture tags within or near the interior space of eth structure. In some embodiments, functional molecules that are locate within the inner space of the structure are maintained within the structure by the addition of one or more additional molecules, for example, to "block" or otherwise sterically prevent the release of the contained molecule. Therefore, in some embodiments, nucleic acid nanostructures are designed to include a "lid" or other structured nucleic acid form that encapsulates a loaded or "captured" functional molecule with in the inner-space of the nanostructure. In some embodiments the access to the inner space of nucleic acid nanostructures is mediated by a structural or conformational change in the structure. Therefore, in some embodiments, the encapsulation of a functional molecule and/or release of the functional molecule from the inner space is controlled by one or more external factors that induce a conformational change in the nanostructure.

b. Functional Molecules

Nucleic acid nanostructures including nucleic acid overhang sequences can capture one or more functional moieties, including but not limited to single-guide- or crispr-RNAs (crRNA), anti-sense DNA, anti-sense RNA as well as DNA coding for proteins, mRNA, miRNA, piRNA and siRNA, DNA-interacting proteins such as CRISPR, TAL effector proteins, or zinc-finger proteins, lipids, carbohydrates. In other embodiments, nucleic acid nanoparticles are modified with naturally or non-naturally occurring nucleotides having a known biological function. Exemplary functional groups include targeting elements, immunomodulatory elements, chemical groups, biological macromolecules, and combinations thereof.

In some embodiments, functionalized nucleic acid nanostructures include one or more single-strand overhang or scaffold DNA sequences that are complementary to the loop region of an RNA, such as an mRNA. Nucleic acid nanoparticles functionalized with mRNAs encoding one or more proteins are described. In one exemplary case, a tetrahedron (but could be any other object that can be designed from the procedure) can be functionalized with 3 (or 1 or 2 or more than 3) single-strand overhang DNA sequences that are complementary to the loop region of an RNA, for example an mRNA, for example an mRNA expressing a protein.

i. Targeting Elements

Targeting elements can be added to the staple strands of the DNA nanostructures, to enhance targeting of the nanostructures to one or more cells, tissues or to mediate specific binding to a protein, lipid, polysaccharide, nucleic acid, etc. For example, for use as biosensors, additional nucleotide sequences are included as overhang sequences on the staple strands.

Exemplary targeting elements include proteins, peptides, nucleic acids, lipids, saccharides, or polysaccharides that bind to one or more targets associated with an organ, tissue, cell, or extracellular matrix, or specific type of tumor or infected cell. The degree of specificity with which the nucleic acid nanostructures are targeted can be modulated through the selection of a targeting molecule with the appropriate affinity and specificity. For example, antibodies, or antigen-binding fragments thereof are very specific.

Typically, the targeting moieties exploit the surface-markers specific to a biologically functional class of cells, such as antigen presenting cells. Dendritic cells express a number of cell surface receptors that can mediate endocytosis. In some embodiments, overhang sequences include nucleotide sequences that are complementary to nucleotide sequences of interest, for example HIV-1 RNA viral genome.

Additional functional groups can be introduced on the staple strand for example by incorporating biotinylated nucleotide into the staple strand. Any streptavidin-coated targeting molecules are therefore introduced via biotin-streptavidin interaction. In other embodiments, non-naturally occurring nucleotides are included for desired functional groups for further modification. Exemplary functional groups include targeting elements, immunomodulatory elements, chemical groups, biological macromolecules, and combinations thereof.

Typically, the targeting moieties exploit the surface-markers specific to a group of cells to be targeted. Exemplary targeting elements include proteins, peptides, nucleic acids, lipids, saccharides, or polysaccharides that bind to one or more targets associated with cell, or extracellular matrix, or specific type of tumor or infected cell. The degree of specificity with which the delivery vehicles are targeted can be modulated through the selection of a targeting molecule with the appropriate affinity and specificity. For example, antibodies, or antigen-binding fragments thereof are very specific.

(a) Antibodies

In some embodiments, nucleic acid nanostructures are modified to include one or more antibodies. Antibodies that function by binding directly to one or more epitopes, other ligands, or accessory molecules at the surface of cells can be coupled directly or indirectly to the nanostructures. In some embodiments, the antibody or antigen binding fragment thereof has affinity for a receptor at the surface of a specific cell type, such as a receptor expressed at the surface of macrophage cells, dendritic cells, or epithelial lining cells. In some embodiments the antibody binds one or more target receptors at the surface of a cell that enables, enhances or otherwise mediates cellular uptake of the antibody-bound nanostructure, or intracellular translocation of the antibody-bound nanostructure, or both.

Any specific antibody can be used to modify the nucleic acid nanostructures. For example, antibodies can include an antigen binding site that binds to an epitope on the target cell. Binding of an antibody to a "target" cell can enhance or induce uptake of the associated nucleic acid nanostructures by the target cell protein via one or more distinct mechanisms.

In some embodiments, the antibody or antigen binding fragment binds specifically to an epitope. The epitope can be a linear epitope. The epitope can be specific to one cell type or can be expressed by multiple different cell types. In other embodiments, the antibody or antigen binding fragment thereof can bind a conformational epitope that includes a 3-D surface feature, shape, or tertiary structure at the surface of the target cell.

In some embodiments, the antibody or antigen binding fragment that binds specifically to an epitope on the target cell can only bind if the protein epitope is not bound by a ligand or small molecule.

Various types of antibodies and antibody fragments can be used to modify nucleic acid nanostructures, including whole immunoglobulin of any class, fragments thereof, and synthetic proteins containing at least the antigen binding variable domain of an antibody. The antibody can be an IgG antibody, such as IgG1, IgG2, IgG3, or IgG4 subtyes. An antibody can be in the form of an antigen binding fragment including a Fab fragment, F(ab')2 fragment, a single chain variable region, and the like. Antibodies can be polyclonal, or monoclonal (mAb). Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they specifically bind the target antigen and/or exhibit the desired biological activity (U.S. Pat. No. 4,816,567; and Morrison, et al., *Proc. Natl. Acad. Sci. USA*, 81: 6851-6855 (1984)). The antibodies can also be modified by recombinant means, for example by deletions, additions or substitutions of amino acids, to increase efficacy of the antibody in mediating the desired function. Substitutions can be conservative substitutions. For example, at least one amino acid in the constant region of the antibody can be replaced with a different residue (see, e.g., U.S. Pat. Nos. 5,624,821; 6,194,551; WO 9958572; and Angal, et al., *Mol. Immunol.* 30:105-08 (1993)). In some cases changes are made to reduce undesired activities, e.g., complement-dependent cytotoxicity. The antibody can be a bi-specific antibody having binding specificities for at least two different antigenic epitopes. In one embodiment, the epitopes are from the same antigen. In another embodiment, the epitopes are from two different antigens. Bi-specific antibodies can include bi-specific antibody fragments (see, e.g., Hollinger, et al., *Proc. Natl. Acad. Sci. USA*, 90:6444-48 (1993); Gruber, et al., *J. Immunol.*, 152:5368 (1994)).

Antibodies that target the nucleic acid nanostructures to a specific epitope can be generated by any means known in the art. Exemplary descriptions means for antibody generation and production include Delves, Antibody Production: Essential Techniques (Wiley, 1997); Shephard, et al., Monoclonal Antibodies (Oxford University Press, 2000); Goding, Monoclonal Antibodies: Principles And Practice (Academic Press, 1993); and Current Protocols In Immunology (John Wiley & Sons, most recent edition). Fragments of intact Ig molecules can be generated using methods well known in the art, including enzymatic digestion and recombinant means.

(b) Capture Tags

In some embodiments, nanostructures include one or more sequences of nucleic acids that act as capture tags, or "Bait" sequences to specifically bind one or more targeted molecules. For example, in some embodiments, overhang sequences include nucleotide "bait" sequences that are complementary to any target nucleotide sequence, for example HIV-1 RNA viral genome. In further embodiments, functional groups are present on one or more staple strands to act as capture tags. For example, in some embodiments, one or more biotinylated nucleotides are incorporated into the staple strand. Streptavidin-coated molecules are therefore introduced via biotin-streptavidin interaction.

Typically, targeting moieties exploit the surface-markers specific to a group of cells to be targeted. Exemplary targeting elements include proteins, peptides, nucleic acids, lipids, saccharides, or polysaccharides that bind to one or more targets associated with cell, or extracellular matrix, or specific type of tumor or infected cell. Targeting molecules can be selected based on the desired physical properties, such as the appropriate affinity and specificity for the target. Exemplary targeting molecules having high specificity and affinity include antibodies, or antigen-binding fragments thereof. Therefore, in some embodiments, nucleic acid nanostructures include one or more antibodies or antigen binding fragments specific to an epitope. The epitope can be a linear epitope. The epitope can be specific to one cell type or can be expressed by multiple different cell types. In other embodiments, the antibody or antigen binding fragment thereof can bind a conformational epitope that includes a 3-D surface feature, shape, or tertiary structure at the surface of the target cell.

ii. Functional Nucleic Acids

In some embodiments, the nucleic acid nanostructures include one or more functional nucleic acids. Functional nucleic acids that inhibit the transcription, translation or function of a target gene are described.

Functional nucleic acids are nucleic acid molecules that have a specific function, such as binding a target molecule or catalyzing a specific reaction. As discussed in more detail below, functional nucleic acid molecules can be divided into the following non-limiting categories: antisense molecules, siRNA, miRNA, aptamers, ribozymes, triplex forming molecules, RNAi, and external guide sequences. The functional nucleic acid molecules can act as effectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA or the genomic DNA of a target polypeptide or they can interact with the target polypeptide itself. Functional nucleic acids are often designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place. Therefore the compositions can include one or more functional nucleic acids designed to reduce expression or function of a target protein.

Methods of making and using vectors for in vivo expression of the described functional nucleic acids such as antisense oligonucleotides, siRNA, shRNA, miRNA, EGSs, ribozymes, and aptamers are known in the art.

(a) Antisense Molecules

The functional nucleic acids can be antisense molecules. Antisense molecules are designed to interact with a target nucleic acid molecule through either canonical or non-canonical base pairing. The interaction of the antisense molecule and the target molecule is designed to promote the destruction of the target molecule through, for example, RNAse H mediated RNA-DNA hybrid degradation. Alternatively the antisense molecule is designed to interrupt a processing function that normally would take place on the target molecule, such as transcription or replication. Antisense molecules can be designed based on the sequence of the target molecule. There are numerous methods for optimization of antisense efficiency by finding the most accessible regions of the target molecule. Exemplary methods include in vitro selection experiments and DNA modification studies using DMS and DEPC. It is preferred that antisense molecules bind the target molecule with a dissociation constant (Kd) less than or equal to $10^{-6}$, $10^{-8}$, $10^{-10}$, or $10^{-12}$.

(b) Aptamers

The functional nucleic acids can be aptamers. Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP and theophiline, as well as large molecules, such as reverse transcriptase and thrombin. Aptamers can bind very tightly with Kd's from the target molecule of less than $10^{-12}$ M. It is preferred that the aptamers bind the target molecule with a Kd less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is preferred that the aptamer have a Kd with the target molecule at least 10, 100, 1000, 10,000, or 100,000 fold lower than the Kd with a background binding molecule. It is preferred when doing the comparison for a molecule such as a polypeptide, that the background molecule be a different polypeptide.

(c) Ribozymes

The functional nucleic acids can be ribozymes. Ribozymes are nucleic acid molecules that are capable of catalyzing a chemical reaction, either intra-molecularly or inter-molecularly. It is preferred that the ribozymes catalyze intermolecular reactions. Different types of ribozymes that catalyze nuclease or nucleic acid polymerase-type reactions which are based on ribozymes found in natural systems, such as hammerhead ribozymes are described. Ribozymes that are not found in natural systems, but which have been engineered to catalyze specific reactions de novo are also described. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for targeting specific cleavage of nucleic acids because recognition of the target substrate is based on the target substrates sequence.

(d) Triplex Forming Nucleotides

The functional nucleic acids can be triplex forming oligonucleotide molecules. Triplex forming functional nucleic acid molecules are molecules that can interact with either double-stranded or single-stranded nucleic acid. When triplex molecules interact with a target region, a structure called a triplex is formed, in which three strands of DNA are forming a complex, dependent on both Watson-Crick and Hoogsteen base-pairing. Triplex molecules are preferred because they can bind target regions with high affinity and specificity. It is preferred that the triplex forming molecules bind the target molecule with a Kd less than $10^{-6}$, $10^{-8}$, $10^{-10}$, or $10^{-12}$.

(e) External Guide Sequences

The functional nucleic acids can be external guide sequences. External guide sequences (EGSs) are molecules that bind a target nucleic acid molecule forming a complex, which is recognized by RNase P, which then cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukaryotic cells. Representative examples of how to make and use EGS molecules to facilitate cleavage of a variety of different target molecules are known in the art.

(f) RNA Interference

In some embodiments, the functional nucleic acids induce gene silencing through RNA interference (siRNA). Expression of a target gene can be effectively silenced in a highly specific manner through RNA interference.

Gene silencing was originally observed with the addition of double stranded RNA (dsRNA) (Fire, et al. (1998) Nature, 391:806-11; Napoli, et al. (1990) Plant Cell 2:279-89; Hannon, (2002) Nature, 418:244-51). Once dsRNA enters a cell, it is cleaved by an RNase III-like enzyme called Dicer, into double stranded small interfering RNAs (siRNA) 21-23 nucleotides in length that contain 2 nucleotide overhangs on the 3' ends (Elbashir, et al., Genes Dev., 15:188-200 (2001); Bernstein, et al., Nature, 409:363-6 (2001); Hammond, et al., Nature, 404:293-6 (2000); Nykanen, et al., Cell, 107: 309-21 (2001); Martinez, et al., Cell, 110:563-74 (2002)). The effect of iRNA or siRNA or their use is not limited to any type of mechanism.

In one embodiment, a siRNA triggers the specific degradation of homologous RNA molecules, such as mRNAs, within the region of sequence identity between both the siRNA and the target RNA. Sequence specific gene silencing can be achieved in mammalian cells using synthetic, short double-stranded RNAs that mimic the siRNAs produced by the enzyme dicer (Elbashir, et al., Nature, 411:494-498 (2001)) (Ui-Tei, et al., FEBS Lett, 479:79-82 (2000)). siRNA can be chemically or in vitro-synthesized or can be the result of short double-stranded hairpin-like RNAs (shRNAs) that are processed into siRNAs inside the cell. For example, WO 02/44321 describes siRNAs capable of sequence-specific degradation of target mRNAs when base-paired with 3' overhanging ends, herein incorporated by reference for the method of making these siRNAs. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit.

Therefore, in some embodiments, the composition includes a vector expressing the siRNA. The production of siRNA from a vector is more commonly done through the transcription of a short hairpin RNAse (shRNAs). Kits for the production of vectors including shRNA are available, such as, for example, Imgenex's GENESUPPRESSOR™ Construction Kits and Invitrogen's BLOCK-IT™ inducible RNAi plasmid and lentivirus vectors. In some embodiments, the functional nucleic acid is siRNA, shRNA, or miRNA.

iii. Gene Editing Molecules

In certain embodiments, the nucleic acid nanostructures are functionalized to include gene editing moieties, or to include components capable of binding to gene editing moieties. Exemplary gene-editing moieties that can be included within or bound to nucleic acid nanoparticles are CRISPR RNAs, for the gene editing through the CRISPR/Cas system.

CRISPR (Clustered Regularly Interspaced Short Palindromic Repeats) is an acronym for DNA loci that contain multiple, short, direct repetitions of base sequences. The prokaryotic CRISPR/Cas system has been adapted for use as gene editing (silencing, enhancing or changing specific genes) for use in eukaryotes (see, for example, Cong, Science, 15:339(6121):819-823 (2013) and Jinek, et al., Science, 337(6096):816-21 (2012)). By transfecting a cell with the required elements including a cas gene and specifically designed CRISPRs, the organism's genome can be cut and modified at any desired location. Methods of preparing compositions for use in genome editing using the CRISPR/Cas systems are described in detail in WO 2013/176772 and WO 2014/018423, which are specifically incorporated by reference herein in their entireties.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. One or more tracr mate sequences operably linked to a guide sequence (e.g., direct repeat-spacer-direct repeat) can also be referred to as pre-crRNA (pre-CRISPR RNA) before processing or crRNA after processing by a nuclease.

In some embodiments, a tracrRNA and crRNA are linked and form a chimeric crRNA-tracrRNA hybrid where a mature crRNA is fused to a partial tracrRNA via a synthetic stem loop to mimic the natural crRNA:tracrRNA duplex as described in Cong, Science, 15:339(6121):819-823 (2013) and Jinek, et al., Science, 337(6096):816-21 (2012)). A single fused crRNA-tracrRNA construct can also be referred to as a guide RNA or gRNA (or single-guide RNA (sgRNA)). Within an sgRNA, the crRNA portion can be identified as the "target sequence" and the tracrRNA is often referred to as the "scaffold."

There are many resources available for helping practitioners determine suitable target sites once a desired DNA target sequence is identified. For example, numerous public resources, including a bioinformatically generated list of about 190,000 potential sgRNAs, targeting more than 40% of human exons, are available to aid practitioners in selecting target sites and designing the associate sgRNA to affect a nick or double strand break at the site. See also, crispr.u-psud.fr/, a tool designed to help scientists find CRISPR targeting sites in a wide range of species and generate the appropriate crRNA sequences.

In some embodiments, one or more vectors driving expression of one or more elements of a CRISPR system are introduced into a target cell such that expression of the elements of the CRISPR system direct formation of a CRISPR complex at one or more target sites. While the specifics can be varied in different engineered CRISPR systems, the overall methodology is similar. A practitioner interested in using CRISPR technology to target a DNA sequence (such as CTPS1) can insert a short DNA fragment containing the target sequence into a guide RNA expression plasmid. The sgRNA expression plasmid contains the target sequence (about 20 nucleotides), a form of the tracrRNA sequence (the scaffold) as well as a suitable promoter and necessary elements for proper processing in eukaryotic cells. Such vectors are commercially available (see, for example, Addgene). Many of the systems rely on custom, complementary oligos that are annealed to form a double stranded DNA and then cloned into the sgRNA expression plasmid. Co-expression of the sgRNA and the appropriate Cas enzyme from the same or separate plasmids in transfected cells results in a single or double strand break (depending of the activity of the Cas enzyme) at the desired target site.

In an exemplary embodiment, crRNA can be extended 3' and CRISPR-Cpf1 loaded with this crRNA can be used to capture this protein/RNA complex, as assayed by gel mobility shift and dual staining with a DNA-specific stain and a protein-specific stain.

Figure 16A:
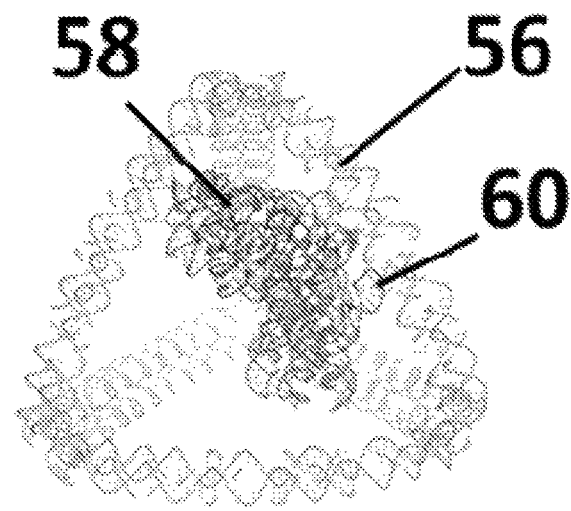
Figure 16B:
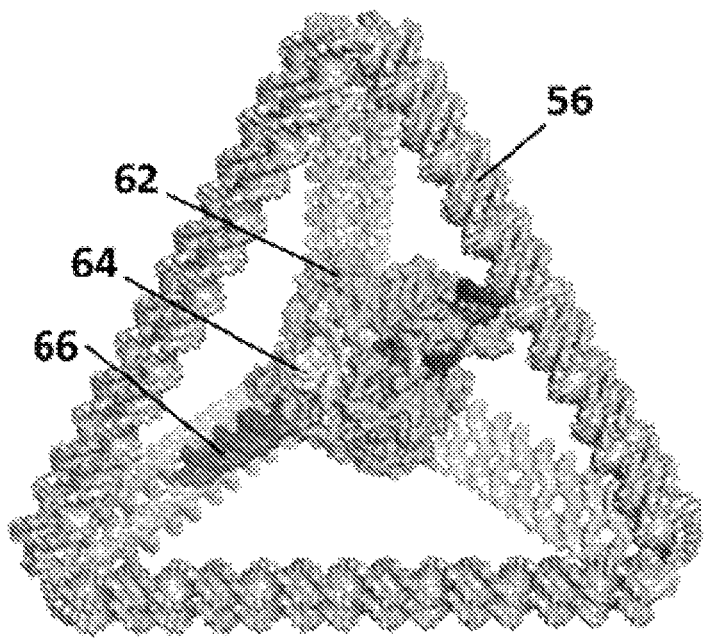

In another embodiment, CRISPR-Cpf1 complexed with crRNA targeting a sequence in the EGFP gene. The crossbeam was made to be a duplex that contains this specific sequence, but could be homologous to the target sequence with 10, 12, 13, 14, 15, 16, 17, 18, 19, 20, 21, 22, 23 nucleotides (20 nucleotides in the example case). The CRISPR-Cpf1/crRNA complex was found to bind to the nanoparticle as assayed by gel mobility shift and dual staining for DNA and protein material. Molecular models of nucleic acid tretrahedra conjugated with RNA (FIG. 16A), and proteins (FIGS. 16B-16C) represent each of three different schemes for using nucleic acid nanostructures for the capture of other molecules. FIG. 16A shows an open wire-frame tetrahedron nanostructure (56) coupled to an mRNA (58) using single strand DNA overhangs extended from the staples at nick positions (60), with the sequence of the overhang complementary to predicted loops in the RNA structure. FIG. 16B depicts CRISPR enzyme Cpf1 (62) with crRNA (64) can be captured onto a DNA nanoparticles (56) on a crossbeam built into the nanoparticle (66), which contains a sequence targeted by the Cpf1/crisprRNA enzyme. FIG. 16C depicts CRISPR enzyme Cpf1 (62) with crRNA (64) can be captured onto a DNA nanoparticles (56) on an overhang sequences built into the nanoparticle (68), which contains a sequence complementary to a 3' extension of the crRNA.

iv. Zinc Finger Nucleases

In some embodiments, the nucleic acid nanostructures include a nucleic acid construct or constructs encoding a zinc finger nuclease (ZFN). ZFNs are typically fusion proteins that include a DNA-binding domain derived from a zinc-finger protein linked to a cleavage domain.

The most common cleavage domain is the Type IIS enzyme FokI. FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487, 994; as well as Li et al. *Proc., Natl. Acad. Sci. USA* 89 (1992):4275-4279; Li et al. *Proc. Natl. Acad. Sci. USA,* 90:2764-2768 (1993); Kim et al. *Proc. Natl. Acad. Sci. USA.* 91:883-887 (1994a); Kim et al. *J. Biol. Chem.* 269:31, 978-31,982 (1994b). One or more of these enzymes (or enzymatically functional fragments thereof) can be used as a source of cleavage domains.

The DNA-binding domain, which can, in principle, be designed to target any genomic location of interest, can be a tandem array of $Cys_2His_2$ zinc fingers, each of which generally recognizes three to four nucleotides in the target DNA sequence. The $Cys_2His_2$ domain has a general structure: Phe (sometimes Tyr)-Cys-(2 to 4 amino acids)-Cys-(3 amino acids)-Phe(sometimes Tyr)-(5 amino acids)-Leu-(2 amino acids)-His-(3 amino acids)-His. By linking together multiple fingers (the number varies: three to six fingers have been used per monomer in published studies), ZFN pairs can be designed to bind to genomic sequences 18-36 nucleotides long.

Engineering methods include, but are not limited to, rational design and various types of empirical selection methods. Rational design includes, for example, using databases including triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,140,081; 6,453,242; 6,534,261; 6,610,512; 6,746,838; 6,866,997; 7,067,617; U.S. Published Application Nos. 2002/0165356; 2004/0197892; 2007/0154989; 2007/0213269; and International Patent Application Publication Nos. WO 98/53059 and WO 2003/016496.

v. mRNA

In some embodiments, nucleic acid nanostructures are modified by covalent or non-covalent association with an RNA that encodes one or more polypeptides, such as a protein. Therefore, in some embodiments, nucleic acid nanostructures are modified to include one or more messenger RNA molecules (mRNA). The messenger RNA can encode any protein or polypeptide. For example, in some embodiments, nucleic acid nanostructures are modified to include one or more mRNAs, each encoding one or more proteins. In an exemplary embodiment, the mRNA encodes a fluorescent protein or fluorophore. Exemplary fluorescent proteins include mCherry, mPlum, mRaspberry, mStrawberry, tdTomato, GFP, EBFP, Azurite, T-Sapphire, Emerald, Topaz, Venus, mOrange, AsRed2, and J-Red. In some embodiments, nucleic acid nanostructures are modified to include one or more messenger RNA molecules an RNA that encodes one or more polypeptides, such as a protein that is an antigen.

vi. Antigens

In some embodiments, nucleic acid nanostructures are modified by covalent or non-covalent association with an antigen. Exemplary antigens include B cell antigens and T cell antigens. B cell antigens can be peptides, proteins, polysaccharides, saccharides, lipids, nucleic acids, small molecules (alone or with a hapten) or combinations thereof. T cell antigens are proteins or peptides. The antigen can be derived from a virus, bacterium, parasite, plant, protozoan, fungus, tissue or transformed cell such as a cancer or leukemic cell and can be a whole cell or immunogenic component thereof, e.g., cell wall components or molecular components thereof. Suitable antigens are known in the art and are available from commercial government and scientific sources. The antigens may be purified or partially purified polypeptides derived from tumors or viral or bacterial sources. The antigens can be recombinant polypeptides produced by expressing DNA encoding the polypeptide antigen in a heterologous expression system. The antigens can be DNA encoding all or part of an antigenic protein. Antigens may be provided as single antigens or may be provided in combination. Antigens may also be provided as complex mixtures of polypeptides or nucleic acids. In some embodiments the antigen is a viral antigen. A viral antigen can be isolated from any virus. In some embodiments the antigen is a bacterial antigen. Bacterial antigens can originate from any bacteria. In some embodiments the antigen is a parasite antigen. In some embodiments the antigen is an allergen or environmental antigen. Exemplary allergens and environmental antigens, include but are not limited to, an antigen derived from naturally occurring allergens such as pollen allergens (tree-, herb, weed-, and grass pollen allergens), insect allergens (inhalant, saliva and venom allergens), animal hair and dandruff allergens, and food allergens. In some embodiments the antigen is a tumor antigen. Exemplary tumor antigens include a tumor-associated or tumor-specific antigen.

vii. Therapeutic or Prophylactic Agents

In some embodiments, nucleic acid nanostructures are modified by covalent or non-covalent association with a therapeutic agent, or a prophylactic agent, or a diagnostic agent. For example, one or more therapeutic, prophylactic, or diagnostic agents can be associated with the exterior of the nucleic acid nanoparticle, or packaged within the interior space of the nucleic acid nanoparticle, according to the design of the particle and location of the capture tag or site of interaction with the Therapeutic or prophylactic or diagnostic agent. A non-limiting list of active agents that can be encapsulated within, or otherwise associated with the nucleic acid nanoparticle includes anti-infectives, immunomodifying agents, hormones, antioxidants, steroids, antiproliferative agents and diagnostic agents. Therapeutic agents can include a drug or modified form of drug such as prodrugs and analogs.

Examples of agents include, but are not limited to, beta-lactam antibiotics (including penicillins such as ampicillin, cephalosporins selected in turn from cefuroxime, cefaclor, cephalexin, cephydroxil and cepfodoxime proxetil); tetracycline antibiotics (doxycycline and minocycline); microlides antibiotics (azithromycin, erythromycin, rapamycin and clarithromycin); fluoroquinolones (ciprofloxacin, enrofloxacin, ofloxacin, gatifloxacin, levofloxacin) norfloxacin, an antioxidant drug includes N-acetylcysteine (NAC); anti-inflammatory drugs, such as nonsteroidal drugs (e.g., indomethacin, aspirin, acetaminophen, diclofenac sodium and ibuprofen); steroidal anti-inflammatory drug (e.g., dexamethasone); antiproliferative agents (e.g., Paclitaxel (Taxol), QP-2 Vincristin, Methotrexat, Angiopeptin, Mitomycin, BCP 678, Antisense c-myc, ABT 578, Actinomycin-D, RestenASE, 1-Chlor-deoxyadenosin, PCNA Ribozym, and Celecoxib) sirolimus, everolimus and ABT-578), paclitaxel and antineoplastic agents, including alkylating agents (e.g., cyclophosphamide, mechlorethamine, chlorambucil, melphalan, carmustine, lomustine, ifosfamide, procarbazine, dacarbazine, temozolomide, altretamine, cisplatin, carboplatin and oxaliplatin), antitumor antibiotics (e.g., bleomycin, actinomycin D, mithramycin, mitomycin C, etoposide, teniposide, amsacrine, topotecan, irinotecan, doxorubicin, daunorubicin, idarubicin, epirubicin, mitoxantrone and mitoxantrone), antimetabolites (e.g., deoxycoformycin, 6-mercaptopurine, 6-thioguanine, azathioprine, 2-chlorodeoxyadenosine, hydroxyurea, methotrexate, 5-fluorouracil, capecitabine, cytosine arabinoside, azacytidine, gemcitabine, fludarabine phosphate and aspariginase); antimitotic agents (e.g., vincristine, vinblastine, vinorelbine, docetaxel, estramustine); molecularly targeted agents including antibodies, antibody fragments, or carbohydrates/polysaccharides (e.g., imatinib, tretinoin, bexarotene, bevacizumab, gemtuzumab ogomicin and denileukin diftitox); and corticosteroids (e.g., fluocinolone acetonide and methylprednisolone).

viii. Other Modifications

In some embodiments, nucleic acid nanostructures include modifications that are not related to the nucleic acid sequence of the staple strands or the scaffold sequence. In some embodiments, the nanostructures include polymers or lipids, for example, surrounding or within the space enclosed by the nanostructure. In a particular embodiment, nanostructures include a complete surface coating, for example, by lipids or other polymers (e.g., polyethylene glycol or phospholipids). Complete surface coating of the nanostructures by lipids or other polymers (e.g., polyethylene glycol or phospholipids) could also be used in order to make these objects able to escape immune defense and enable the capacity of external modification. Therefore, in some embodiments, the surface of the nanostructure includes an amount of lipid or other polymer effective to coat the nanostructure and reduce immune surveillance or immune uptake of the nanostructure. In some embodiments, the surface of the nanostructure includes an amount of lipid or other polymer effective to enable external modification, for example, by insertion of one or more proteins, lipids, nucleic acids, polymers or small molecules into the lipid or polymer layer reconstituted around the nanoparticle. Preferred polymers are biocompatible (i.e., do not induce a significant inflammatory or immune response) and nontoxic.

Examples of suitable hydrophilic polymers include, but are not limited to, poly(alkylene glycols) such as polyethylene glycol (PEG), poly(propylene glycol) (PPG), and copolymers of ethylene glycol and propylene glycol, poly (oxyethylated polyol), poly(olefinic alcohol), polyvinylpyrrolidone), poly(hydroxyalkylmethacrylamide), poly(hydroxyalkylmethacrylate), poly(saccharides), poly(amino acids), poly(hydroxy acids), poly(vinyl alcohol), and copolymers, terpolymers, and mixtures thereof.

In preferred embodiments, the one or more hydrophilic polymer segments contain a poly(alkylene glycol) chain. The poly(alkylene glycol) chains may contain between 1 and 500 repeat units, more preferably between 40 and 500 repeat units. Suitable poly(alkylene glycols) include polyethylene glycol, polypropylene 1,2-glycol, poly(propylene oxide), polypropylene 1,3-glycol, and copolymers thereof.

In some, embodiments, amphiphilic proteins or other amphiphilic molecules (e.g., drugs) including targeting moieties, or not including targeting moieties, or combinations, are inserted in a lipid layer reconstituted around the nanoparticles.

Some further non-limiting examples include targeting the therapeutic, prophylactic or diagnostic agent to the disease sites for therapeutic and/or diagnostic purposes.

V. Uses

DNA nanostructures prepared according to methods described above are suitable for many applications. Some exemplary uses include in drug delivery, in biosensors, in memory storage, in nano-electronic circuitry, etc.

A. Delivery Vehicles

DNA nanostructures are suitable as a delivery vehicle for therapeutic, prophylactic and/or diagnostic agents. Since they are nucleic acid based, DNA nanostructures are entirely biocompatible and elicit minimal immune response in the host. The automated design of any desired geometry of DNA nanostructure further allows manipulation of DNA structure tailored for individual drugs, dose, site of target and desired rate of degradation etc.

Any prophylactic, therapeutic, or diagnostic agent can be incorporated into the DNA origami nanostructures via a variety of interactions, non-covalent or covalent. Some exemplary non-covalent interactions for attachment include intercalation, via biotin-streptavidin interaction, chemical linkers (e.g., using Click-chemistry groups), or via hybridization between complementary nucleotide sequences.

In some embodiments, the agents to be delivered are simply captures inside the DNA origami nanostructures. In these cases, pore size of the DNA polyhedron is a key consideration, i.e., they are small enough so that the agent captured does not leak out. In some embodiments, the DNA polyhedron are assembled in two halves to allow the capture of agent prior to the completion of the polyhedron nanostructures.

Prior work has shown that DNA origami as a carrier for anti-cancer drugs such as doxorubicin had increased cellular internalization and increased target cell killing as well as circumvented drug resistance (Jiang Q et al., *Journal of the American Chemical Society* 134.32: 13396-13403 (2012)). Small molecules, such the anti-cancer drug doxorubicin, can attach to the DNA origami structures through intercalation.

1. Agents to be Delivered

In some embodiments, therapeutic, prophylactic, toxic, diagnostic or other agents are delivered using the nucleic acid nanoparticles. Exemplary agents to be delivered include proteins, peptides, carbohydrates, nucleic acid molecules, polymers, small molecules, and combinations thereof. In some embodiments, the nucleic acid nanoparticles are used for the delivery of a peptide drug, a dye, an antibody, or antigen-binding fragment of an antibody.

Therapeutic agents can include anti-cancer, anti-inflammatories, or more specific drugs for inhibition of the disease or disorder to be treated. These may be administered in combination, for example, a general anti-inflammatory with a specific biological targeted to a particular receptor. For example, one can administer an agent in treatment for ischemia that restores blood flow, such as an anticoagulant, anti-thrombotic or clot dissolving agent such as tissue plasminogen activator, as well as an anti-inflammatory. A chemotherapeutic which selectively kills cancer cells may be administered in combination with an anti-inflammatory that reduces swelling and pain or clotting at the site of the dead and dying tumor cells. Suitable genetic therapeutics include anti-sense DNA and RNA as well as DNA coding for proteins, mRNA, miRNA, piRNA and siRNA. In some embodiments, the nucleic acid that forms the nanoparticles include one or more therapeutic, prophylactic, diagnostic, or toxic agents.

2. Delivery of Agents

In some embodiments, therapeutic, prophylactic, toxic, diagnostic or other agents are delivered to a cell or tissue by endogenous uptake of the nucleic acid nanoparticles by the cell or tissue. In some embodiments, the agents are released from the nucleic acid nanoparticles within the blood stream. In other embodiments the agent are released within the gastro-intestinal system, uro-genital system, lymphatic system, central nervous system, or into the skin. The release of agents bound to or otherwise associated with the nucleic acid nanoparticles can occur in vivo, by contact with one or more enzymes, proteins or other factors present in physiological concentrations. Exemplary enzymes include nuclease enzymes, such as exonucleases, endonucleases and other restriction enzymes, proteases, hydrolases and other enzymes. When release of an agent involves a conformational change in the structure of the nucleic acid nanoparticles, the conformational change can occur as a result of exposure to one or more physiological conditions, such as pH, salt concentration or interaction with one or more substances present in the body.

B. Scaffold Structures for Display and Analysis of Molecules

DNA origami nanostructures can act as scaffolds for a variety of molecules including protein, nucleic acid, lipids, or polysaccharides. In some, embodiments, one or more molecules are conjugated to the nanoparticles. For example, in some, embodiments, one or more molecules are conjugated to the outside of the nanoparticle, to the inside of the nanoparticle, or both to the inside and outside of the particle. Any molecules of interest can be conjugated to the nanoparticles. Exemplary categories of molecule that can be conjugated include proteins, lipids, carbohydrates, small-molecules, nucleic acids and combinations.

In some embodiments nanostructures are used to capture and/or restrain molecules in a fixed and known orientation, for example, to assist biophysical analyses, such as structural determination.

1. Systems for Capturing RNAs for Biophysical Characterization

In some embodiments, polyhedral nucleic acid nanostructures are used as a framework structure of known dimensions that is uniform and stable, for biophysical characterization of one or more molecules of interest. For example, in some embodiments, ribonucleic acid molecules can be captured on a polyhedral nucleic acid nanostructure to orient and display the RNA molecules amenable for structural or biochemical characterization. An exemplary ribonucleic acid is a viral RNA genome.

A powerful class of highly structured DNA origami objects is obtained with high throughput synthesis and complexing with unstructured RNAs enabling their high-resolution reconstruction or low-resolution structural inference by determining complexation with the target structure of interest with complementary bait sequences, protein, or other small molecule affinity tags. The automated approach allows programming, modelling, assembling, and structurally characterizing a broad range of DNA nanostructures using a single scaffold strand combined with specific sets of staple strands, commonly referred to as DNA origami (Castro, C E et al., *Nature Methods.* 8, 221-229 (2011); Rothemund, P W, *Nature.* 440, 297-302 (2006); Krishnan, Y et al., *Trends in Cell Biology.* 22, 624-633 (2012); Pan, K et al., *Nature Communications.* 5, 5578 (2014)). DNA nanostructures have already shown great potential for light harvesting (Dutta, P K et al., *Journal of the American Chemical Society.* 133, 11985-11993 (2011); Pan, K et al., *Nucleic Acids Research.* 42, 2159-2170 (2014)), metallic nanoparticle casting (Sun, W et al., *Science.* 346, 1258361 (2014)), and biologics delivery (Douglas, S M et al., *Science.* 335, 831-834 (2012); Fu, J et al., *Nature Biotechnology.* 30, 407-408 (2012)). This ability to computationally design large libraries of DNA nanostructures of arbitrary size and functionalization sites to "capture" RNA genomes such as HIV allows for rapid prototyping of assemblies that can probe specific points in 3D space.

a. Biophysical Characterization of Bound Molecules

The methods further provide structural characterization of the ribonucleic acids encapsulated by the polyhedral nucleic acid nanostructures. These complexes are suitable for structural characterizations using techniques including chemical foot-printing, cryo-electron microscopy, X-ray crystallography, small-angle X-ray scattering, analytical ultracentrifugation, chromatographic methods, light scattering and combinations thereof. For example, in some embodiments, the methods include chemical foot printing by selective 2'-hydroxyl acylation analyzed by primer extension (SHAPE), and cryo-electron microscopy for determining secondary and tertiary structures of the ribonucleic acids. Automatically-generated libraries of nanostructures including capture tags or "bait" sequences can be used to produce nanostructures for use in high-throughput methods. For example, object selection and automated design follow the principles that the pores are either big enough to allow diffusion of RNA into the object (as in FIG. 16A), or that they are used in two halves that cage the RNA after binding. In preferred embodiments, the computational method takes into account diversity of scaffold sequences, which additionally is used to aid in characterization of nanostructures based on thermal melting analysis. For example, in some embodiments, an RNA structure pipeline is formed which takes an RNA molecule and, through SHAPE analysis and nanostructure binding assays the secondary structure with 3D constraints as well as the full 3D structure are determined by cryo-EM.

In some embodiments, highly structured DNA origami objects that are complexed with unstructured RNAs are used to enable their high-resolution reconstruction. In preferred embodiments, computationally designed large libraries of rigid nucleic acid structures of arbitrary size and functionalization sites that "capture" RNA genomes, such as HIV, allow for rapid prototyping of assemblies that probe specific points in 3D, similar to the notion of a lock-and-key mechanism. In other embodiments, complexes of nucleic acids and nanostructures are used for detection of structured nucleic acids, for example, RNA molecules, in blood or other biological samples of interest. Complexes of nucleic acids and nanostructures can be read-out for bio-sensing applications. For example, "barcodes" tagged onto structured DNA assemblies or other structure-specific tags or ligands can be used as capture agents to select or identify target RNAs of interest. As an analogy, for a "key" that is of unknown shape (i.e., the RNA), the shape is determined by trying it against a combinatorial library of "locks" (i.e., the arbitrary shaped DNA nanostructures) to determine which lock fits the key best. Typically, lock and key interactions occur through avidity binding interactions to arbitrary baits of interest that are structured in 3D space to complement the target structure of interest.

In some embodiments, a library is constructed of DNA nanostructures with complimentary regions to find the "locks" that fit the RNA key. In some embodiments, the readout is in the form of high-throughput methods that determine both tight binding of the RNA to the DNA nanostructure, as well as through chemical foot-printing analysis to obtain structural constraints of the RNA on the nanostructure, and to ensure no deformation of the key by the lock. In preferred embodiments, programmed DNA nanostructures capture and hold RNAs in native conformations allowing for library-based conformational probing and uniform particle visualization by cryo-EM.

In some embodiments, this RNA lock-and-key approach is applied to select the best structures for characterization by cryo-EM. In preferred embodiments, the structure is modeled and validated by cryo-EM, with a resolution<20 Å.

Typically, the methods include one or more of the following steps:
(A) Generating a library of DNA nanostructures in silico;
(B) Synthesizing and folding of DNA nanostructures;
(C) Binding of DNA nanostructures to RNAs of interest;
(D) Structural characterization of the DNA nanostructure and RNA complexes.

Optionally, the library of DNA nanostructures in silico is further selected to reduce the total number of DNA scaffold and staple strands for maximal spatial coverage while limiting redundancy thus being experimentally practical in synthesizing and assembly of the target DNA nanostructures.

Methods for generating high-throughput nanostructure libraries are described. The methods determine distance constraints of nanostructured RNA to different points of attachment on a nanostructure of known geometry, use chemical foot-printing of RNA on nanostructures, and optimize binding of the RNA to instances of the DNA nanostructure library for ultimate use in cryo-EM, crystallography, or scattering.

Figures 17E, 18:
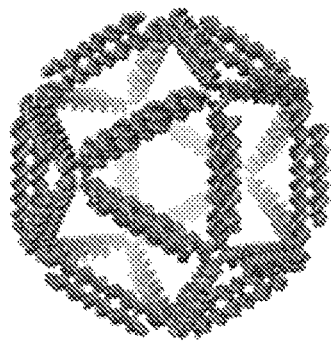

An overview of an exemplary high throughput pipeline for characterizing secondary, and tertiary structures of RNAs is shown in FIG. 18.

This is fundamentally different from existing methods for structural and sequence analyses, which do not create scaffolds for RNA presentation and are limited by the large size of RNAs combined with their conformational flexibility. Use of nucleic acid nanostructures of arbitrary size and functionalization sites to "capture" RNA genomes such as HIV allows for rapid prototyping of assemblies that can probe specific points in 3D. Structures of RNAs can be back-determined by screening it against a combinatorial library of nanostructures having differently-arranged binding motifs, to determine which "lock" (i.e., structural conformation) fits the "key" (i.e., RNA) best. In this manner, a library of DNA nanostructures can be generated covering complimentary regions, to find the lock(s) that fit the RNA key, as well as other applications. The nucleic acid scaffolds can include a user-defined scaffold sequence, and the staple sequences are varied accordingly.

The methods can include conducting biophysical analyses of the framework/target molecule complex, such as chemical foot-printing, fluorimetry or colorimetery based readout, or high-resolution structural characterization using x-rays or cryo-EM.

Methods of structurally and chemically characterizing 3-D structures of single-stranded nucleic acids of interest are provided. In some embodiments, the single-stranded nucleic acid molecules are single-stranded RNA molecules. An exemplary single-stranded RNA molecule is a viral genome. In some embodiments, the single-stranded RNA genome is the HIV genome.

Therefore, methods of encapsulating a viral genome such as the HIV-1 genome using a set of polyhedral nucleic acid nanostructures with single-strand bait sequences complementary to the regions of the single-stranded HIV genome, and subsequent structural characterization, are also provided. Other exemplary structured nucleic acids of interest include messenger RNAs, long non-coding RNAs, and structured genomic segments, such as chromatin, etc.

The tertiary structures of the captured RNAs are determined using high-throughput chemical foot-printing and sequencing and high-resolution cryo-electron microscopy, or other optical read-out including fluorimetry or colorimetric assay. Based on the natural structural principles helpful in the ribosome structure determination, with proteins acting to structure the ribosomal RNA, by adding DNA-based structured elements to the HIV genome, uniform and orientable RNA objects are generated for high resolution structural characterization. A schematic illustration showing diversity of nanostructure library design is depicted in FIG. 18.

i. Binding Detection Analysis

Detection of stably bound target molecules can be done through a variety of methodologies known in the art but specifically implemented as part of the method for optimal nanostructure selection from a library. Notable detection methods are through the use of quantitative reverse-transcription polymerase chain reaction (qRT-PCR), fluorometric, colorimetric, and calorimetric methods.

In some embodiments, the RNA is bound to nanostructures that are affixed to solid support and then washed multiple times under a variety of conditions including but not limited to increased temperature and decreased salt. Remaining tightly bound RNA is then reverse transcribed and quantitative detection is carried out to determine the exact amount of RNA present against the bound DNA nanostructures.

In some embodiments, RNA affinity can be tested against the library of DNA nanostructures using calorimetric tests including differential scanning calorimetry and isothermal titration calorimetry.

In some embodiments, the binding of the RNA can be detected by fluorescence or calorimetric assays, which include the toe-hold release of a second oligonucleotide that triggers the translation of a fluorescent protein production (GFP) or enzyme that modifies small molecules to change color (as in (Pardee et al., *Cell*, 159:940-945 (2015)), or fluorescent RNA folding (e.g. RNA spinach aptamer).

ii. Chemical Foot-Printing Analysis

In some embodiments, chemical foot-printing analysis is used to obtain structural constraints of nucleic acids of interest bound onto the nucleic acid nanostructures. An exemplary chemical foot-printing technique is selective 2'-hydroxyl acylation analyzed by primer extension (SHAPE).

SHAPE chemistries exploit small electrophilic reagents that react with 2'-hydroxyl groups to interrogate RNA structure at single-nucleotide resolution (Wilkinson K A et al., *Nat Protoc.* 1(3):1610-6 (2006)). Mutational profiling (MaP) identifies modified residues by using reverse transcriptase to misread a SHAPE-modified nucleotide and then counting the resulting mutations by massively parallel sequencing. The SHAPE-MaP approach measures the structure of large and transcriptome-wide systems (Smola M J et al., *Nat Protoc.* 10, 1643-1669 (2015)). In some embodiments, one or more chemical foot-printing methods are used including exemplary methods such as SHAPE, and SHAPE-MaP.

In yet other embodiments, pre-folded RNAs, and DNA nanostructures are incubated together and allowed to form complexes. Dimethylsulfate (DMS), N-methyl isatoic anhydride (NMIA), neat DMSO, or buffer is added to the complex samples in each well. The action of DMS or NMIA is to modify the 2'O of the RNA when single stranded (Siegfried, N A et al., *Nature Methods.* 11, 959-965 (2014); Henderson, R et al., *Structure.* 20, 205-214 (2012); He, Y et al., *Nature.* 452, 198-201 (2008)). Subsequently, the sample is desalted and the published technique of SHAPE-MaP is used, where the reverse transcriptase is added along with Manganese (rather than Magnesium) to generate mutations at sites of 2'O modifications (Siegfried, N A et al., *Nature Methods.* 11, 959-965 (2014)). In some embodiments, next generation sequencing is used to obtain a mutation profile, showing the secondary structure of the bound RNA. This reveals both sites of binding to the object (by absence of mutations compared to the single-stranded unbound modifications) and also the secondary structure constraints on the bound RNA. Optimal DNA and RNA concentrations are optimized to ensure high-quality SHAPE data of singly bound complexes. In some embodiments, random baits and internal baits are used as controls, as well to probe non-specific interactions.

iii. Cryo-Electron Microscopy (Cryo-EM)

Single-particle cryo-EM and subsequent 3D particle reconstruction is a superior method for structural elucidation of designed nanostructures. Cryo-EM has already been a proven method for RNA structure determination of the ribosome (Amunts, A et al., *Science.* 348, 95-98 (2015)), as well as for large viral particles (Wang, Z et al., *Nature Communications.* 5, 4808 (2014)). In some embodiments, RNAs that have been rigidified by the DNA nanostructures are subsequently subject to structural characterization, for example, by cryo-EM reconstruction, X-ray crystallography, etc.

In some embodiments, adjustments are made to sequence and geometry of programmed DNA nanostructures to aid in further structural rigidity for increased resolution in cryo-EM. In some embodiments, chirality of the DNA nanostructures is implemented using asymmetry in the nanostructure design or by the addition of duplexes and/or gold nanoparticles to specific locations on the DNA nanostructure. In other embodiments, to aid in structural characterization, gold nanoparticles attached to single stranded DNA baits specific to other locations in the RNA is used to identify the presence and location of the RNAs during cryo-EM structuring. In further embodiments, sequence routing techniques that allows for use of square or honeycomb edges are implemented, making a much more rigid overall structure. In yet further embodiments, adding in tension and twist to the DNA nanostructure allow for structures to be forced to free energy minima (Wilkinson, K A et al., *Nature Protocols.* 1, 1610-1616 (2006)).

In some embodiments, RNAs deemed stably attached to the DNA nanostructure are structurally solved by cryo-EM, with SHAPE-determined secondary structure and distance constrains incorporated into the final model. Multiple nanostructure designs allow for a better understanding of native RNA structural fluctuations. In some embodiments, RNA-DNA nanostructures that have identical conformation are generated to allow the enhancement of the signal to noise through particle averaging. In further embodiments, hundreds of thousands of images of molecules with identical conformations but with different orientations are averaged in order to obtain high resolution cryo-EM structure of asymmetric molecules. The cryo-EM field has the capability to resolve structures of molecular machines to 2-3 Å resolution routinely (Fan, et al., *Nature.* 527, 336-341 (2015); Wang, et al., *Nature Communications,* 5, 4,808 (2014)).

C. Sensors

DNA origami nanostructures can act as biosensors for a variety of molecules including protein, nucleic acid, lipids, or polysaccharides. In particular, the DNA origami nanostructures prepared according to the methods described above are capable of adopting any arbitrary shapes, therefore making them ideal sensor for other molecules, or secondary and tertiary structures of other molecules.

For example, DNA origami nanostructures have been shown to act as a DNA repair nanosensor at single-molecular level (Tintore, et al., *Angew Chem Int Ed Engl.* 22; 52 (30): pp. 7747-50 (2013)).

In some embodiments, DNA origami nanostructures are used to capture RNA molecules of interest for probing their secondary and tertiary structures. In preferred embodiments, the DNA origami nanostructure:RNA complexes are suitable for further structural analysis for example, particularly using selective 2'-hydroxyl acylation analyzed by primer extension (SHAPE), or cryo-EM analysis.

In some embodiments, DNA origami nanostructures are designed for binding to a particular RNA virus, for example human immunodeficiency virus (HIV), influenza, Ebola, hepatitis C, SARS, and Zika viruses. In some embodiments, DNA origami nanostructures are used as RNA/viral detection sensors for use in the battlefield.

D. Nanoelectronic Circuitry

DNA nanostructures prepared according to methods described above are suitable for use as nanoscale electronic devices. The automation of DNA nanostructure design allows user input of any desired geometry. The staple strands can be functionalized for incorporating any desired functionalities such as anchoring to any surfaces, for incorporating any non-naturally occurring molecules, etc.

In some embodiments, metallization of the DNA template is used for circuit fabrication. In preferred embodiments, the shape of DNA origami nanostructures is maintained after the metallization process.

The present invention will be further understood by reference to the following non-limiting examples.

E. Imaging Probes

DNA nanostructures prepared according to the described methods above are suitable for use as a molecular probe, for example, as a fluorescent probe. Based on the capacity to generate structures with random geometries and size, and the facility of modification on prescribed position determined by the user, fluorescent dyes could be easily conjugated. The number of fluorescent dyes that can be conjugated depends on the structure size and the number of the staple strands that can be modified.

In some embodiments dye-conjugated nucleic acid nanostructures are used for conjugation to specific ligand-binding moieties, such as antibodies, aptamers, protein-binding domains, etc., for example, by integrating chemical groups (e.g., Click-chemistry groups, amine groups, etc.) into the nanostructures. Nanostructures including specific ligand-binding moieties are used for labelling and imaging applications, such as imaging and super-resolution imaging.

F. Light-Harvesting and Excitonic Circuits

DNA nanostructures containing densely or loosely packed aggregates of chromophores can be used as excitonic energy transfer circuits. Chromophores of prescribed types can be organized using the 3D arrays published here to form 1D/2D/3D architectures for exciton funneling and transport in nanoscale energy transport.

G. Vaccines and Adjuvants 3D organizations of viral proteins can be used to stimulate the immune system by presenting these proteins in geometries that mimic the one or more naturally occurring antigens. Exemplary antigens include viral antigens, parasite antigens, bacterial antigens, allergens or environmental antigens and tumor antigens. In an exemplary embodiment, the antigen is a natural viral capsid structure.

Specific DNA sequences may also be included as adjuvants, with the 3D patterning in geometry and size controlled in an arbitrary manner using the procedure provided here in which the DNA wireframe geometry scaffolds viral proteins or peptides or other active fragments. In some embodiments the antigen is a viral antigen. A viral antigen can be isolated from any virus. In some embodiments the antigen is a bacterial antigen. Bacterial antigens can originate from any bacteria. In some embodiments the antigen is a parasite antigen. In some embodiments the antigen is an allergen or environmental antigen. Exemplary allergens and environmental antigens, include but are not limited to, an antigen derived from naturally occurring allergens such as pollen allergens (tree-, herb, weed-, and grass pollen allergens), insect allergens (inhalant, saliva and venom allergens), animal hair and dandruff allergens, and food allergens. In some embodiments the antigen is a tumor antigen. Exemplary tumor antigens include a tumor-associated or tumor-specific antigen

EXAMPLES

Example 1: Fully Automatic and Robust Inverse Design of Programmed DNA Assemblies Structure-based, rational design of macromolecular assemblies including both nucleic acids and proteins is a long-standing aim of nanotechnology and biological engineering. Unlike proteins, which contain a myriad of specific and non-specific inter-residue interactions that determine their local and global folds, and RNA, which exhibits promiscuity in secondary structure and base-pairing, synthetic DNA assemblies are well established to be highly programmable using Watson-Crick base pairing alone (Seeman, et al., *Biophys. J.* 44, 201-209 (1983); Rothemund, P W K, *Nature*, 440, 297-302 (2006)). In particular, wireframe polyhedral geometries offer the powerful ability to program nearly arbitrary 3D geometries on the nanometer scale, limited only by current size constraints imposed by single-stranded scaffold lengths. This important and versatile class of topologies therefore has broad potential for programming complex nanoscale geometries including biomimetic systems inspired by viruses, photosynthetic systems, as well as other natural highly evolved macromolecular assemblies. Achieving full automation of inverse sequence design using this versatile wireframe approach has the potential to realize the original vision of Ned Seeman to program nanoscale materials with full 3D control over positioning of all atomic-level groups (Seeman, N C et al., *Biophys. J.* 44, 201-209 (1983); Rothemund, P W, *Nanotechnology: Science and Computation.* 3-21 (2006)).

As an alternative, a robust and fully automatic inverse design procedure is introduced here that programs arbitrary wireframe DNA assemblies based on an input wireframe mesh without reliance on user feedback or limitation to spherical topologies. The procedure has been applied to design 35 Platonic, Archimedean, Johnson, and Catalan solids, six asymmetric structures specified using surface geometry alone, as well as four polyhedra with non-spherical topologies. Designed sequences are used to synthesize icosahedral, tetrahedral, cuboctahedral, octahedral, and reinforced hexahedral structures using asymmetric PCR (aPCR) for facile production of single-stranded scaffolds of custom length and sequence. Programmed objects are confirmed using cryo-electron microscopy (cryo-EM), folding, and stability assays, to be both high fidelity structurally as well as stable under low-salt buffer conditions important to biological as well as in vitro applications.

Methods and Materials
  Design Formula
  Specifying Geometry

The goal of this work is to design nanostructures with a top-down approach: given a target structure of specified size and geometry, as well as scaffold sequence; the formula will generate the required staple strand sequences to experimentally fold the structure. To specify the geometry, the spatial coordinates of all vertices, the edge connectivities between vertices, and the faces to which vertices belong must be provided. These may be provided manually, or through a file format that specifies polygonal geometry, such as the Polygon File Format (PLY), Stereolithography (STL), or Virtual Reality Modeling Language (WRL). As explained in more detail below, any closed, orientable surface network can serve as input to the formula (FIGS. 2A and 2B). Provided in the code is a parser to convert PLY files into the required inputs.

In addition to the spatial information, the lengths of the edges must be specified, with the constraint that each must be a multiple of 10.5 bp, rounded up or down to the nearest nucleotide, with a minimum of 31 bp. For structures with equal edge lengths throughout the geometry, such as Platonic, Archimedean, or Johnson solids, this is easily satisfied, whereas for other geometries rounding edge lengths may be required, resulting in some possible deviation between the specified target structure and final design. In these cases, the desired minimum edge length (e.g., 31 or 42 bp) is assigned to the shortest edge and the other edges are scaled and rounded appropriately. When using the automated rounding to generate edge lengths, the user is advised to verify that edge lengths are satisfactory before proceeding to the scaffold routing procedure.

Generating the Spanning Tree

In routing the single-stranded scaffold through the entire DNA origami structure, the first requirement is to ensure an Eulerian circuit (Ellis-Monaghan, J A et al., *Nat. Comput.*, 1-13 (2014)). An Eulerian circuit, more strict than an Eulerian path, is required because the ends of the scaffold should be adjacent to create a single scaffold nick. In the case of circular scaffold strands, the nick is where the excess staple forms a loop.

An Eulerian circuit is guaranteed when the degree of every vertex is even. This can be achieved by using an even number of duplexes per edge in the structure; in this work, two duplexes per edge were chosen, each a DX-tile.

Even though finding an Eulerian circuit is guaranteed, there is a multitude of routing solutions that are all Eulerian circuits. However, not all circuits would lead to effective scaffold routings. For example, a scaffold strand entering a vertex from one edge must exit the vertex from an adjacent edge, one that shares a face with the first edge. It may not exit from the same edge it came from, nor may it exit from a non-adjacent edge. The former case would lead to an edge that is disconnected from the vertex, and the latter case would lead to intersecting DNA strands. This requirement leads to a subset of Eulerian circuits known as A-trails (Bent, S W et al., *Discrete Appl. Math.* 18, 87-94 (1987)).

With these constraints in mind, there are a few corollaries that follow. Looking at a single edge, crossovers between two helices may be used to strengthen the rigidity of the combined unit (Kallenbach, N R et al., *Nature*. 305, 829-831 (1983)). Crossovers can occur with staple strands or with scaffold strands. In the case of the design paradigm presented here, which employs two duplexes per edge, there can only be zero or one scaffold crossover per edge. More than one scaffold crossover would lead to internal scaffold loops that are disconnected from the rest of the scaffold. Therefore, a scaffold strand entering an edge from a vertex can either leave the edge from the same vertex or from the other vertex. Similarly, looking at a single vertex, at least one edge connected to the vertex must have zero scaffold crossovers. If all edges at the vertex have scaffold crossovers, an internal loop would be generated. However, a scaffold crossover is in fact necessary. Looking at a single face or any closed circuit of edges, at least one edge must have one scaffold crossover. If all edges have no scaffold crossovers, an internal loop would be generated.

Because scaffold crossovers are required, one way to design a polyhedron would be to identify all the possible locations for a scaffold crossover, and then select which locations shall have the scaffold crossover based on the above criteria. Doing so would lead to a valid structure, and is a viable approach for designing arbitrary scaffolded DNA origami (Pan, K et al., *Nat. Commun.* 5 (2014)). However, the number of locations for a scaffold crossover scales with the size of the object, making the formula computationally intractable for many structures. Most apparently, structures with the same symmetry have similar routing patterns regardless of size. A very general approach cannot take advantage of this and would iterate through all possibilities of scaffold crossovers, when in fact the solution is predictable and can be reached more quickly.

Given the above restrictions on the number and location of edges with a scaffold crossover for DNA origami objects, solving the scaffold routing can be mapped to a simpler problem: classifying edges as either possessing zero scaffold crossovers or possessing one scaffold crossover.

From the above criteria, the edges with zero scaffold crossovers must connect to every vertex, and there can be no cycles of edges with zero scaffold crossovers, meaning that there are V-1 edges with zero scaffold crossovers, where V is the number of vertices, and the rest have one scaffold crossover. The edges with zero scaffold crossovers meet the definition of a spanning tree of a network (see FIG. 1).

Thus, solving the scaffold routing problem is identical to solving for a spanning tree of the structure, where each possible spanning tree corresponds to a unique scaffold routing. FIGS. 3A-3D present two different spanning trees for a tetrahedron. Given a network, Prim's formula can be used to conduct a Breadth-first search (BFS) spanning tree. If, as in this case, all edges are weighted the same, Prim's formula will generate a breadth-first search spanning tree, one with the most branches. It has been shown that branching trees self-assemble more reliably than more linear trees (Pandey, S et al., *Proc. Natl. Acad. Sci.* 108, 19885-19890 (2011)).

Note that with this spanning tree formula, there are no restrictions on the topology of the network. Any arrangement of nodes and edges can be routed with an Eulerian circuit, using a spanning tree to define the placement of scaffold crossovers. However, the use of faces allows A-trails to be defined much more easily in automation, and some networks do not have clearly defined faces, i.e., planar faces with an unambiguous outward normal. (An example of this would be eight cubes stacked in a 2×2×2 formation, for a total of 27 vertices. The faces around the vertex at the center are not clearly arranged, making several scaffold routings about that vertex possible.) As such, the current formula is well-suited for any closed surface, which includes not only spherical topologies but also toroidal polyhedra and other geometries with holes.

Adding Pseudo-Nodes and Routing Scaffold

Once the spanning tree has been determined, the graph needs to be converted to an Eulerian circuit (FIG. 1 and FIGS. 3A-3J). First, for each edge that is not in the spanning tree, a pair of pseudo-nodes is added to split the edge into two halves, each corresponding to one side of a scaffold crossover (FIGS. 3E and 3F).

Next, for each vertex in the graph, a set of pseudo-nodes is added to replace the vertex node. A vertex of degree N has N edges emerging from it and N faces between them. For each face, a pseudo-node is placed that joins the two bordering edges and disconnects them from the other edges. After all pseudo-nodes are placed for all vertices, the original vertex nodes are no longer part of the graph, and each edge is now bounded on both ends by pseudo-nodes. This defines the Eulerian circuit through which the scaffold will be routed (FIGS. 3E-3F).

This circuit defines two possible routings: one that routes around faces clockwise, and one that routes around faces counterclockwise, relative to the outward normal. The direction of the scaffold is chosen to run counterclockwise around each face, so that for convex vertices (the majority of cage vertices) the major grooves of the duplexes at each vertex point inward to minimize electrostatic repulsion of the backbone (FIG. 1, and FIGS. 3G-3L) (He, Y et al., *Angew. Chem.* 122, 760-763 (2010)). The undirected graph is converted to a directed graph to implement this directional choice.

At this point, the lengths of the edges are introduced into the formula; the spanning tree and pseudo-node addition are only geometry-specific, independent of size. The scaffold nick position, for simplicity, is chosen to always be located on an edge without scaffold crossovers, on the duplex far from staple nicks and crossovers. Using Prim's formula, this edge will have Vertex #1 as one of its endpoints, since with the most-branching default all edges connected to Vertex #1 are members of the spanning tree. Marking this 5'-end as scaffold base #1, each of the scaffold bases are subsequently numbered with knowledge of the edge lengths and routing scheme, all while keeping track of their relative position on their edge. Note that for each edge, the 5'-end overhangs the 3'-end by one nucleotide to ensure that all staple and scaffold crossovers remain perpendicular to the helical axes. The half-edges, namely those edges that are split by the scaffold crossover, have lengths that are pre-determined by some simplifying assumptions. The scaffold crossover is placed as close to the center as possible, with a convention set here to have a preference towards the lower-index vertex if needed. Therefore, it is deterministic how long a particular section of a scaffold is on a given edge (FIG. 3M, and Table 1).

Adding Staple Strands and Generating Sequence

Each scaffold base now has two pieces of information associated with it: one index number indicates its position on the scaffold strand, and set of numbers indicate its spatial location: the edge, the duplex, and the position from the 5' end. In routing the staple strands, the latter set is used to identify which bases in the staples are paired with which bases in the scaffold, then the former index number is assigned to the staples accordingly.

There are three categories of staple strands, each with their own prescribed pattern: staples on vertices, staples on edges with scaffold crossovers, and staples on edges without scaffold crossovers. The staples on vertices pair with the first 10-11 nucleotides of each duplex abutting the vertex, with poly-T bulges of length 5 crossing between edges. There are two varieties of vertex staple designs implemented: one system uses single crossovers in some places to ensure that there is 10-11 bp of continuous duplex for high specificity and binding strength, and the other, more traditional, system uses double crossovers everywhere, leading to a minimum of 5 bp of continuous duplex (He, Y et al., *Nature*. 452, 198-201 (2008); Zhang, F et al., *Nat. Nanotechnol.* 10, 779-784 (2015)). For the structures synthesized and characterized in this work, the former paradigm is used, as the higher binding strength was found to create a more cooperative transition at a higher temperature (FIGS. 9I-9L). The pattern of staple routing depends on the degree of the vertex, ensuring that each staple length is 52- or 78-nucleotides (nt) long for ease of synthesis.

$$a = \begin{cases} 0, & \text{if } n \bmod 3 = 0 \\ 2, & \text{if } n \bmod 3 = 1 \\ 1, & \text{if } n \bmod 3 = 2 \end{cases} \quad \text{(Eq. 1)}$$

$$b = \frac{n - 2a}{3} \quad \text{(Eq. 2)}$$

where a is the number of 52-nt staples at the vertex,
  b is the number of 78-nt staples at the vertex, and
  n is the degree of the vertex.

The edge staples pair with the intermediate nucleotides between vertex staples. For the edges with scaffold crossovers, two 31-32-nt staples are placed across the scaffold crossover, together occupying a 15-16-nt region on either side of the crossover for sufficiently strong binding. The remainder of scaffold has 42-nt staples placed to create staple crossovers every 21 base pairs, with a 20- or 22-nt staple in the case of a 10- or 11-nt remainder. The edges without scaffold crossovers simply follow this latter pattern, filling with as many 42-nt staples that can fit and using a 20- or 22-nt staple when necessary (FIG. 3N).

TABLE 1

Determining the location of a scaffold crossover for a given edge length. The variables X and Y are defined for the region hybridized by edge staples, ignoring the 10- and 11-bp regions on either side hybridized by vertex staples. By convention set here, X ≤ Y, where X is the region closer to the lower-index vertex, and Y is the region closer to the higher-index vertex.

X + Y + 21 = L
X ≤ Y

| | L = 21n + {10 or 11} | L = 21n + 0 |
| --- | --- | --- |
| Edge length L is even | Off-center by 0.5, F = X + 1 (e.g. L = 52: X = 15, Y = 16) | Off-center by 5.5, Y = X + 11 (e.g. L = 42: X = 5, Y = 16) |
| Edge length L is odd | Off-center by 0, Y = X (e.g. L = 31: X = 5, Y = 5) | Off-center by 5, F = X + 10 (e.g. L = 63: X = 16, Y = 26) |

The minimum edge length allowed in this design paradigm is 31 bp. Any smaller value will place a scaffold crossover 5 nt away from the end of an edge (in the vertex staple region) and would not lead to a high yield. However, the rules described above work well for lengths 42 bp and greater, and they need to be modified slightly for 31- and 32-bp edges. First, a 31/32-bp edge has 21 bp occupied by vertex staples, leaving 10 or 11 bp for edge staples. Therefore, in both types of edges, a 20- or 22-bp staple is placed with a single crossover on one side, because a staple nick in the middle would conflict with the scaffold crossover. This in turn means that the single-crossover vertex staple design may lead to a missing crossover, so to be safe the double-crossover vertex staple design is always used in any structure with a 31- or 32-bp edge present.

After all the staples are placed, each staple is a vector of numbers, each value corresponding to the scaffold nucleotide to which it is base paired. Then, the input or generated scaffold sequence is used, matching a base identity (A, T, G, or C) to a scaffold number. If no sequence is provided, a segment of M13pm18 is used by default if the required scaffold length is less than 7249 nucleotides, and a sequence is randomly generated if the required length is greater. The complementary nucleotide via Watson-Crick base pairing is then be computed and assigned to the corresponding staple nucleotides. Finally, this list of staple sequences is output for synthesis.

Predicting 3D Structure

The positions of each base pair are calculated by interpolating between the two ends of the edge it resides on, and shifting away perpendicularly from the central axis by 10 Å, half the interhelical distance for an anti-parallel crossover. The edge is assumed to lie in a plane with a normal vector defined by the sum of the unit normal vectors of the two neighboring faces.

There are several ways to define the location of the ends of the edges. The DX-tile edges can be assumed to be two parallel cylinders with combined width 40 Å (20 Å interhelical distance and 20 Å duplex diameter). This can be further simplified to a rectangle with width 40 Å, with the line of the edge serving as a central axis (FIGS. 5A-5F). In the ideal case, the corners of these rectangles meet, since the scaffold exits and enters the edge from these locations. The widths of the rectangles together would form an N-sided regular polygon, because they have the same sides and have equal angles between them. The perpendicular distance from the center of this polygon and an edge (the beginning of the interpolation) is the inradius of this polygon. From the inradius, the distance between the vertex and the beginning of the DX-tile edge is determined using the sum of the face angles. If the multi-arm DX-tile were flat, this would be equivalent to the inradius.

$$s = \frac{2\pi}{\theta_{tot}} r \qquad \text{(Eq. 3)}$$

where s is the distance between the vertex and the beginning of the DX-tile edge, r is the inradius of the polygon formed by the widths of the tiles, and $\theta_{tot}$ is the sum of all face angles at the vertex.

For regular N-sided polygons, $$r = \frac{w}{2}\cot\left(\frac{\pi}{N}\right) \qquad \text{(Eq. 4)}$$

where w is the combined width of the DX-tile (40 Å).

There are some structures, however, whose edges do not meet at regular angles, such as the Archimedean solids. In that case, depending on the convention used to define the length of the inradius, there will be backbone stretches or nucleotide overlaps (FIGS. 5A-5F). For a representative Archimedean solid, the size of the object is best fit when backbone stretches are minimized, where the inradius is calculated based on the largest face angle.

$$r = \frac{w}{2}\cot\left(\frac{\theta_{max}}{2}\right) \qquad \text{(Eq. 5)}$$

where $\theta_{max}$ is the largest face angle. Note that this general equation applies to regular N-sided polygons as well, since $\theta_{max}=2\pi/N$.

For structures with concave vertices, where $\theta_{tot}>2\pi$, to obey the convention that all edge axes meet at a single point, it is defined that s=r, creating a sphere of radius r that defines the edge boundaries.

A schematic representation of the workflow including each of the steps to implement the top-down design of nucleic acid nanostructures is depicted in FIG. 1.

Results

To enable the fully automatic and robust inverse design of programmed DNA assemblies in order to pattern 3D geometries of arbitrary lipids/proteins/sugars/RNAs/PNAs scaffolded using DNA nanostructures, arbitrary geometries were rendered as node-edge networks based on the DX-based wireframe motif in which inter-connected edges consist of two duplexes joined using anti-parallel (DX) crossovers (FIG. 1) (Rothemund, *Nanotechnology: Science and Computation*. 3-21 (2006); He, et al., *Nature*. 452, 198-201 (2008); Zhang, et al., *Nat. Nanotechnol*. 10, 779-784 (2015); Yan, et al., *Science*. 301, 1882-1884 (2003); Fu, et al., *Biochemistry* (Mosc.). 32, 3211-3220 (1993)). This strategy offered application of the procedure to any closed geometric surface including non-spherical topologies such as a torus, provided that it can be rendered using polyhedral surface meshes. Using this approach, the spatial coordinates of all vertices, the edge connectivities between vertices, and the faces to which vertices belong fully specify the target object. Standard polyhedron file formats containing this information are converted into this set of arrays, providing input to the scaffold routing and staple design procedure (FIGS. 2A and 2B). Programmed edges are required to consist of multiples of 10.5 bp rounded to the nearest nucleotide, as commonly assumed in DNA origami design to satisfy the natural helicity of B-form DNA. Obeying the natural geometry of DNA ensures that no over- or under-wind in duplexes occurs, which may otherwise result in shape distortions that force deviation from the target geometry and would require iterative, ad hoc adjustment of edge lengths and sequence design (Yan, et al., *Science*. 301, 1882-1884 (2003)).

Representing the target geometry as a polyhedral mesh that satisfies the preceding design criteria guarantees that a single-stranded scaffold can be routed uniquely throughout the entire object using an Eulerian circuit, without modifications to the target geometry. From the mesh, the graph of the target structure is computed, containing the vertex, edge, and face information (FIG. 1). Scaffold routing is then assigned using a spanning tree and Prim's formula (Prim, R C *Bell Syst. Tech. J.* 36, 1389-1401 (1957)). Each of the edges that is a member of the spanning tree corresponds to an edge without a scaffold crossover, whereas the remainder have one scaffold crossover. Every possible spanning tree for a given graph corresponds to a unique scaffold routing, where by default Prim's formula generates a maximally-branching spanning tree that has been shown to self-assemble more reliably than linear trees (FIGS. 3A-3L) (Pandey, S et al., *Proc. Natl. Acad. Sci.* 108, 19885-19890 (2011)). Importantly, use of DX arms to represent edges also ensures a solution that is efficiently obtained in solution time on the order of E log V, where E and V are the number of edges and vertices, respectively (Prim, R C *Bell Syst. Tech. J.* 36, 1389-1401 (1957)). To complete the scaffold routing, a scaffold crossover is placed at the center of each edge that is not part of the preceding spanning tree. A linear scaffold nick position is set to ensure that it is non-coincident with crossovers and other nicks, with the polarity of its routing chosen to be counter-clockwise around each face due to the preference of the major groove to orient inwards at vertices (He, Y et al., *Angew. Chem.* 122, 760-763 (2010)). Thus, use of the spanning tree approach enables fully automatic conversion of the input polyhedral geometry to full scaffold routing based on the single circuit that traverses each duplex once.

With the scaffold routing determined, staple strands are assigned automatically using distinct rules for edge versus vertex staples enabling the assignment of staple strand sequences assuming Watson-Crick base complementarity (FIG. 1, and FIGS. 3L-3M). Finally, the positions and orientations of each nucleotide are modeled to predict the 3D structure of the nanoparticle (FIG. 1, FIGS. 4A-4H and FIG. 13). Critically, in contrast with previous tile-based approaches that employed this DX-motif to synthesize nanoparticles of diverse form (He, Y et al., *Nature.* 452, 198-201 (2008)), the use of a single-stranded DNA scaffold that is routed throughout the entire object in the strategy offers quantitative yield of the final product in its self-assembly, no dependence on relative multi-arm junction tile concentrations, and full control over DNA sequence. This final feature is essential to biomolecular applications that utilize spatially specific asymmetric sequence programming for protein or RNA scaffolding as well as other chemical functionalization.

To test the generality and robustness of the design procedure to be applied to diverse polyhedral geometries, it was first applied to design Platonic solids that have equal edge lengths, angles, and vertex-degree, followed by geometries of increasing complexity including Archimedean solids with unequal vertex angles, Johnson solids that include heterogeneity in vertex degree, and Catalan solids that have unequal edge lengths (FIGS. 2A and 2B). Applicability to asymmetric and non-convex objects specified using surface geometry alone (Yan, H et al., *Science.* 301, 1882-1884 (2003)) was also confirmed (FIG. 1, and FIG. 4), in addition to non-spherical topologies including a nested cube, a nested octahedron, and tori that have not been realized experimentally (Zhang, F et al., *Nat. Nanotechnol.* 10, 779-784 (2015); He, Y et al., *Angew. Chem.* 122, 760-763 (2010)) and cannot be solved computationally using existing procedures (Yan, H et al., *Science.* 301, 1882-1884 (2003)). Taken together, these examples illustrate the broad ability of the procedure to automatically generate complex scaffold and staple routings for diverse geometries based on top-down geometric specification alone (FIGS. 2A and 2B).

Example 2: Automated Inverse Design of Programmed DNA Assemblies with Modified Geometry Methods and Materials To create nanostructures having modified geometry at the edges and vertices, parameters specifying both the number of nucleic acid helices and cross-sectional geometric pattern are input. A modified and enhanced procedure related to the methods described in Example 1 is carried out to specify scaffold routing throughout the desired geometry at each edge of the nanostructure. In addition, the geometry of each vertex can be defined as being flat (i.e., non-beveled) or having beveled edges, to accommodate the cross-sectional geometry of each edge as it enters and leaves the vertex.

Modifying Geometry

To route a single-stranded scaffold throughout the entire geometry with edges formed from 6 double helices arranged in honey-comb morphology (6 HB edges), geometric manipulation to generate six-lines per each edge is carried out. Each edge is detached from two vertices connected to it and its length is shortened (FIG. 14A) with the offset-distance (between the vertex and end point of the shortened edge) calculated by the angle between two adjacent edges at the vertex and the distance between two helices where the origin of the local coordinate is located. After this, the connectivity of each separated line is newly constructed with two conjugated endpoints. The number of separated points is twice the number of separated lines regardless of the number of vertices. Then, at the center of every separated line, three vectors, $t_1$-$t_2$-$t_3$ as basis vectors of the local coordinate system are introduced to determine the optimal translation and orientation of helices along the edges. The vector, $t_1$ of the local coordinate system is defined by position vectors of two points from the connectivity of each separated line, which is parallel to each helical axis. The vector, $t_2$ is the average of two normal vectors that are perpendicular to each face interfaced with the local vector, $t_1$. The vector, $t_3$ is obtained by the cross product of two vectors $t_1$ and $t_2$.

Before converting each separated edge into six-lines modeling six-duplexes, the cross-section of a honeycomb lattice shape is defined as six circles on two local vectors, $t_3$-$t_2$. To avoid clashing between neighboring duplexes, which occurs depending on the dihedral angle between two adjacent faces of the structure, two possible layouts are used; the bottom origin in which the origin of two local vectors is located at the center of two bottom circles (hereafter called reference circle) and the middle origin in which two middle circles are used as reference circles. The reference circle is only connected to the closest reference circle of the adjacent separated line sharing the same face. In an $t_1$-$t_3$ cross-section view of the honeycomb helix lattice for any $t_1$-depth, each circle has diameter of 2.25 nm that is slightly larger than diameter of the double-helical B-form DNA, 2 nm. The difference is to reflect the electrostatic repulsion between neighboring duplexes which may lead a somewhat large effective inter helical spacing 2.25 nm, as assumed previously (Dietz, H et al., *Science* 325, 725-30 (2009); Castro, C. E. et al., *Nat. Methods* 8, 221-229 (2011); Pan, K. et al., *Nat. Commun.* 5, 5578 (2014)). The integer number (called a section ID) on each circle is assigned to model the asymmetric ends of DNA strands; the circle is the 5'-end having a terminal phosphate group when it is an even number and the circle is 3'-end having a terminal hydroxyl group when it is an odd number. Then, according to the section ID, each separated edge is replaced with six arrow lines with endpoints. For even-numbered circles, the arrow points in the same direction as $t_1$. For odd-numbered circles, the arrow points in the opposite direction as $t_1$. Since the arrow will be substituted with scaffold running 5'-end to 3'-end and staple running in 3'-end to 5'-end direction, each double helix has nearest neighbor where the strands have opposite parity. Thus, six antiparallel cross-linked DNA helixes are employed as the six-line segments between every two adjacent vertices of the initial geometry. Subsequently, the minimum length line among all separated lines is found and scaled (e.g., multiple of 21-bp greater than 42-bp edge length). The minimum edge length allowed in this six-helix bundle design paradigm is 42-bp since more than two double-crossovers between adjacent duplexes are guaranteed.

Finding Distributed Scaffold Double-Crossovers

The next step is to generate the loop-crossover structure (FIG. 14B). The endpoints of multiple line segments are joined (FIG. 14C) such that every line becomes part of a loop. The endpoint of the line segment generated by the reference circle is connected with the closet endpoint of the adjacent line segment from the reference circle (bottom origin in this example). Four remaining endpoints are interconnected with each other according to the following rule; two endpoints are diagonally connected in the bottom origin and horizontally connected in the middle origin. Thus, the initial geometry consisted of $N_F$ faces and $N_E$ edges introduces $N_F+2\times N_E$ closed loops in which the $N_F$ loops are originated from the connection by the red line and the $2\times N_E$ loops are generated by connecting the endpoints by the blue line.

For each base-pair with the nucleic acid scaffold, the relative positions and angles of each nucleotide is modeled to find the possible crossovers in both scaffold and staples. First, the length of line segments is discretized as a multiple of base-pair lengths, 0.34 nm that is the length of base-pair rise in the double-helical B-form DNA model. The certain number of base-pairs at the end of discretized line segments, except for the line segments originated from the reference circle, are added or deleted to find the nearest position of the scaffold crossover. For instance, in the case of the bottom origin, discretized lines from a section ID of 2 or 3 are moved 3-bp on the 3'-end direction, and those from a section ID of 4 or 5 are moved 1-bp on the direction of the 5'-end to connect each other at the permitted position of the scaffold crossover. For the middle origin, all of the discretized lines except for those from a section ID of 3 are shifted by 1-bp on the 3'-end direction, thus a cross-sectional shape is relatively flat compared to one formed by the bottom origin. Given the helical periodicity with 10.5 nucleotide pairs per turn, there are two possible starting block, the prior and posterior block, for the base-pair at end of the 5' which belong to the section ID of 1. With the block ID of 0, initial angle pointing the nucleotide of scaffold is defined as 270° for the even section ID and 270° for the odd section ID when applying the bottom origin. The initial angle with the block ID of 0 is also defined as 30° for the even section ID and 210° for the odd section ID when applying the middle origin. Thus, when considering a section ID of 3 and the bottom origin, the prior block with the ID of 3 and the poster block with ID of 13 have the angle of 167.1° (270°-360°×2/21×3) and 184.3° (270°-360°×2/21×13), respectively, which point almost the same orientation that can be connected without any unpaired nucleotides of the scaffold. The base-pair with different starting blocks results in the different patterns of scaffold and staple crossovers, which affect final sequence design even when applying the same staple-break rule. We adapted and used the posterior block as the starting block in both bottom and middle origin since it has more the 14-nt seed dsDNA domains whose presence enhances folding yield (Ke, Y. et al., *Chem. Sci.* 3, 2587 (2012); Martin, T. G. et al., *Nat. Commun.* 3, 1103 (2012)).

Scaffold double-crossovers are found and introduced by connecting between two closed loops (scaffold strand), creating the loop-crossover structure (FIG. 14C). Possible staple crossovers are restricted to intersections between the block and every third layer of a stack of planes orthogonal to the helical axes, spaced apart in intervals of 7-bp or two-thirds of a turn (Douglas, S. M. et al., *Nucleic Acids Res.* 37, 5001-6 (2009)). Then, possible scaffold crossovers are permitted at positions displaced upstream or downstream of the corresponding possible staple crossover points by 5-bp or a half-turn, except for those that are 7-bp away from the both ends of the discretized line. Only two double-crossovers are selected per section 0 to 5 in a zig-zag pattern with respect to the center edge and the double-crossover connecting its own loop is eliminated to avoid cycles. FIG. 14C shows scaffold loops with initial double-crossovers (double line) of the tetrahedron DNA origami structure with the 6HB as the edge, in which $N_F+2\times N_E-1$ double-crossovers among them are selected through the following scaffold route process.

Generating the Spanning Tree of the Dual Graph of the Loop-Crossover Structure

In routing the single-stranded scaffold through the entire DNA origami structure, the first requirement is to ensure an Eulerian circuit exists (Ellis-Monaghan, J. A. et al., *Nat. Comput.* 14, 491-503 (2015)). An Eulerian circuit, which is stricter than an Eulerian path, is required because the ends of the scaffold should be adjacent to create a single scaffold nick. An Eulerian circuit is guaranteed when the degree of every vertex is even. This can be achieved by using an even number of duplexes per edge in the structure; in this work, we have chosen to use six duplexes per edge, each a six-helix bundle. Since the degree of every corner connected by the crossover and loop always remains two (even), it becomes an Eulerian circuit by choosing the proper number of double-crossovers of the loop-crossover structure. Thus, the scaffold routing problem can be solved by computing a spanning tree of the dual graph of the loop-crossover structure, which determines the proper number of double-crossovers without any cycle that is a route of edges and nodes wherein a node is reachable from itself. In order for loop-crossover structure that employs six duplexes per edge to be an Eulerian circuit, $N_f+2N_e$ closed loops should be connected to each other by $N_f+2N_e-1$ double-crossovers. This implies that the edge is constructed by six-duplexes with two or three scaffold double-crossovers which are determined by the spanning tree calculation.

In order to consistently select two or three double-crossovers for each edge, the weight factor is assigned to each double-crossover with the value of 1 for two mandatory double-crossovers, the value of 2 for the occasional double-crossover, and the value of 3 for the unwanted double-crossover. Despite having twelve ways to impose the weight factor of the double-crossover connecting two adjacent loops, we chose to adapt pattern #1 for the bottom origin and pattern #13 for the middle origin since the final staples with this pattern include more 14-nt seed dsDNA domains.

Then, the dual graph of the loop-crossover structure is generated (FIG. 14D), in which each loop becomes represented by a node and each double-crossover becomes represented as an edge joining the analogous nodes and transferring the assigned weight factor of the double-crossover. Given the dual graph network, Prim's or Kruskal's algorithm can be used to find the minimum weight spanning tree in which $N_F+2\times N_E-1$ edges are determined with the priority of small weight factor of the edge. The edges that are members of the spanning tree correspond to the subset of double-crossovers required to complete the Eulerian circuit.

Inverting the Spanning Tree and Completing Scaffold Route

Figure 14E:
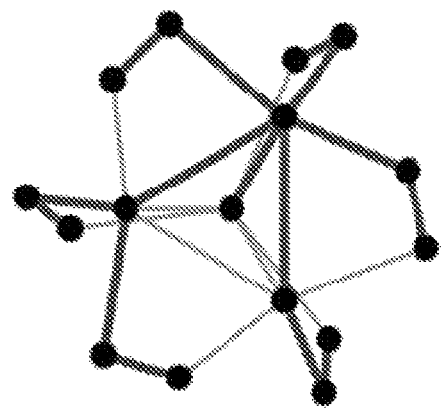
Figure 14F:
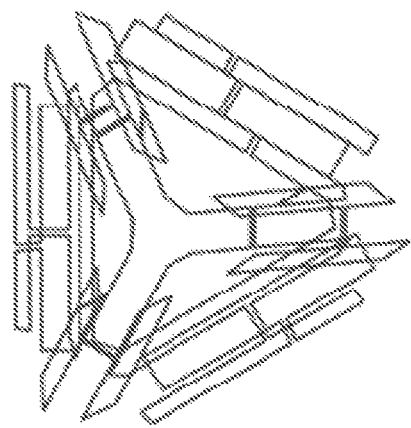

Once the spanning tree of the dual graph network has been determined, the graph is inverted back to the loop-crossover structure only using members of the spanning tree (FIGS. 14E-14F). By choosing a particular subset of double-crossovers in the loop-crossover structure, these discrete loops can be connected to form one continuous circular scaffold through the entire structure. The direction of the circular scaffold is set to have the same direction defined by the corresponding section ID and the nick position is chosen to be placed on the duplex far from crossovers and staple nicks, which reveals the final scaffold routing. In the case of the design paradigm presented here, which employs six duplexes per edge, one-single stranded scaffold can go through the entire structure and visit each edge of the initial geometry two times with every edge having two or three scaffold double-crossovers.

Adding Staple Strands and Sequences

In the next step, the staple strands wind in antiparallel direction around the scaffold to assemble B-form double helices and the staple sequences can be computed based on complementary Watson-Crick base pairing with the scaffold sequence.

First, staple paths complementary to the scaffold are assigned by adding all permitted staple double-crossovers except for those that would be not 5-bp away from a scaffold crossover between the same two helices and not 7-bp away from the both ends of discretized lines in the base pair model. The two staples crossing between edges are connected with a certain number of nucleotides with poly-T bulges where the staple paths do not bind to the scaffold, which serve as to prevent blunt-end stacking. Since a phosphate-phosphate distance of roughly 0.7 nm is known as B-form DNA (Rich., *Proc. Natl. Acad. Sci. U.S.A* 95, 13999-14000 (1998)), the number of unpaired nucleotides in the poly-T bulge is calculated by dividing the spatial distance between two nucleotides to be joined by 0.4 nm (a value slightly smaller than 0.7 nm is used to reduce the tension between the connection). Second, the initial staple paths built from permitted staple crossovers and the poly-T bulge can be non-circularized after placing a nick at the center of the longest dsDNA domain and where it is non-coincident with staple and scaffold crossovers. Lastly, the non-circular staple paths are broken into shorter segments 20 to 60 nucleotides long, usually with a mean length of about 40 nucleotides. With design criteria of including at least one 14-nt seed domain per each staple, we suggested and investigated two alternative staple-break rules called "maximized staple length" and "maximized number of seed domains".

Before applying the staple-break rule of the maximized staple length, the size of dsDNA domains of each initial staple are examined from 5'-end to 3'-end by using a searching bar and the searching bar is place at end of 5'-end of the initial staple to be segmented. The searching bar continues to move to the center position of the next dsDNA domain in the 5'-end direction until the distance traveled exceeds 60-bp length. Then it continues to move back to previous dsDNA domain in the 3'-end direction until the domain located at the searching bar is longer than or equal to 14-bp length. Finally, the backbone nick is placed at the center of the domain, which divides the initial staple into two. The above steps are repeated until the length of the remaining staple is smaller than 60-bp length. The algorithm does not consider the inclusion of the 14-nt seed domain for the staple to be cut, but guarantees the 7-bp length as the minimum length of the dsDNA domain for the segmented staple.

For the staple-break rule of the maximized the number of seed domains, it is based on the previous suggested staple-break rule where backbone nicks are never placed in dsDNA domain longer than 7-bp and nicks are positioned 3 and 4-bp away from crossovers in 7-bp domain. To apply the above staple-break rule to our staple route design procedure automatically, the searching bar that is initially placed at the end of the 5'-end continues to move to the next dsDNA domain until finding the domain that is longer than or equal to the 14-bp length and the distance traveled exceeds 20-bp length. Then the backbone nick is placed at the center position of the next dsDNA domain regardless its size. In the above rule, the initial staple are broken by considering the presence of the 14-nt seed domain of the staple to be cut, so it is most likely to contain more than one 14-nt seed domain per each staple. However, each broken staple has the potential to include the dsDNA domains with the small size since it does not consider the size of the domain to be broken.

Note that each staple broken by the maximized staple length contains the 14nt seed domain with more than 90% of total staples, which is a slight percentage than when applying the maximized the number of seed domains. However, since it does not contain the small size domain that induces weak Watson-Crick base paring, we adapted and used the maximized staple length as the staple-break rule in the staple routing.

Figure 14G:
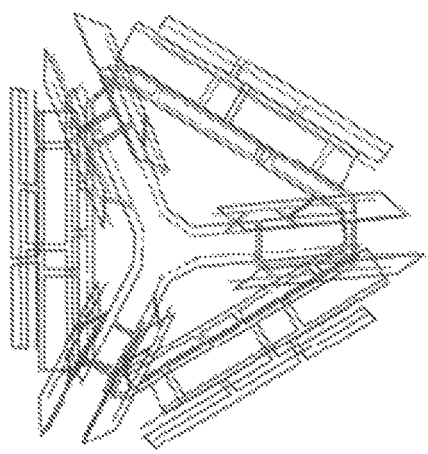
Figure 14H:
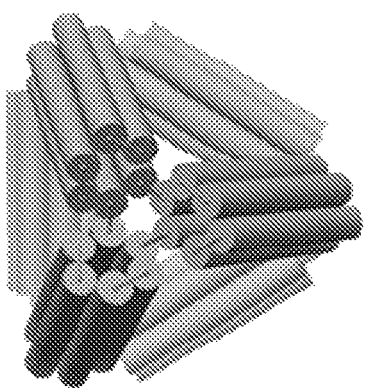
Figure 14I:
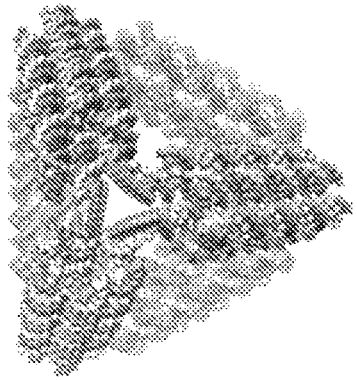

After all staples are attached and segmented, each staple is denoted by a vector of numbers, with each value corresponding to the scaffold nucleotide to which it is base-paired. The input or generated scaffold sequence is then used to match base identities (A, T, G, or C) to the corresponding scaffold number assuming Watson-Crick base-pairing. If no sequence is provided, a segment of M13mp18 is used by default if the required scaffold length is less than or equal to 7,249-nt, and a sequence is randomly generated of the required length is greater. Finally, this list of staple sequences is output for synthesis (FIGS. 14G-14I). Equivalent schematic representations outlining each of the nine steps for top-down sequence design procedure for scaffolded DNA of arbitrary target geometry based on an open surface that is discretized using a polygon mesh are shown in FIGS. 15A-15I.

Nanoparticle Assembly

M13mp18 (NEB #N4040S; Bayou Biolabs #P-107) was incubated at 20 nM final concentration in a buffer containing 1×TAE (40 mM Trizma base, 20 mM glacial acetic acid, 1 mM EDTA) and 14 mM $MgCl_2$ and mixed with 800 nM final concentration staples (40 molar excess). The mix was annealed from 95° C. to 22° C. over 24 hrs (95° C. 3 min; 90° C. 3 min; 85° C.–70° C. 5 min at each temperature in 0.5° C. increments; 70° C.-22° C. 14 min at each temperature in 0.5° C. increments.

Confirmation of Nanoparticle Assembly and Structural Validation

Assembled nanoparticles were mixed with loading buffer and ran on a 2% agarose gel with 1×TAE supplemented with 12 mM $MgCl_2$ and 1×INVITROGEN SYBR®SAFE for 3 hrs at 70V at 4° C. and visualized under blue light. The nanoparticle sample was compared against scaffold with a shift indicating a properly folded particle.

Assembled nanoparticles were purified from the excess staples by filtering on a pre-washed Amicon Ultra-0.5 mL centrifugal filter 100 k MWCO spin filter and exchanged 5 times by spinning at 3,000 RPMs for 20 minutes and re-suspended in clean buffer with $MgCl_2$. Purified nanoparticles were visualized by electron microscopy stained with 2% uranyl acetate affixed to glow discharged carbon coated grids.

Results

The methods for top-down design of nanoparticles having edges formed of six double helices arranged in a honeycomb cross-sectional lattice were applied to produce DNA nanoparticles of different edge lengths and geometries.

The following DNA nanostructures were designed with scaffold routed through 6-helix-bundle edge types and structurally validated according to the methods: Tetrahedron with 63 base pair edge length; tetrahedron with 84 base pair edge lengths; octahedron with 84 base pair edge lengths; and tetrahedron, octahedron, and pentagonal bipyramid nanoparticles with 42 base pair edge lengths. In addition, a tetrahedron with base pair edge length of 63 nucleotides was folded with a beveled vertex type and visualized according to the methods.

The structures were assembled and folded as visualized by the gel shift migration between the scaffold and the folded particle. The resulting nanoparticles were structurally characterized by transmission electron microscopy or cryo-electron microscopy, the electron micrograph confirming the structures were assembled and folded according to the design criteria.

Example 3: Synthetic Yield and Homogeneity of Self-Assembled DNA Origami Objects Methods and Materials
  Materials
  Chemicals Tris-Acetate-EDTA buffer, $MgCl_2$, NaCl, TRIS-base, and nuclease-free water were purchased from Sigma-Aldrich. The Zymoclean gel DNA recovery kit was purchased from Zymo Research, Inc. and the Amicon Ultra-0.5 mL centrifugal filter (MWCO 100 kDa) from EMD Millipore, Corp. Restriction enzymes and the DNA ladder (Quick-Load® Purple 2-Log DNA ladder 0.1-10 kb) were provided by New England Biolabs, Inc. (NEB), the PCR enzyme (Accustart® Taq DNA polymerase HiFi) by Quanta Bioscience, Inc., low melt agarose by IBI Scientific, Inc., Seakem® agarose by Lonza Group, Ltd., and SYBR Green (10000×) by Thermo Fisher Scientific, Inc.

Oligonucleotides and DNA Templates

M13mp18 single-stranded DNA scaffold as well as the Lambda DNA was provided by NEB. (N4040S, N3011S). All oligonucleotides (for DNA assembly, asymmetric PCR, and scaffold digestion) and double stranded DNA gBlocks® were purchased from Integrated DNA Technologies, Inc. and used without further purification.

ssDNA Scaffold Synthesis
  Single Stranded DNA Fragment of 200 to 6000 Nts Amplification Using aPCR Asymmetric PCR amplification of ssDNA M13mp18: The asymmetric PCR was performed with a Mastercycler personal thermal cycler (Eppendorf, Inc.) using a sense primer concentration of 1 μM, an antisense primer concentration of 20 nM and 30 ng of M13MP18 ssDNA template. PCR primers were designed using Primer3 online software (v. 0.4.0) (Untergasser, A et al., *Nucleic Acids Res.* 40, e115-e115 (2012); Koressaar, T et al., *Bioinformatics.* 23, 1289-1291 (2007)) and are presented in Table 2. The maximum yield was obtained using 1 unit of Accustart Taq DNA polymerase HiFi in HiFi buffer complemented with 2 mM of magnesium sulfate and 200 μM of dNTPs mix in a final volume of 50 μL. Single strand synthesis was also achieved by using standard Taq polymerase (Sigma Aldrich #D1806) using aPCR optimized protocol described for the Accustart Taq DNA polymerase HiFi and using the HiFi Buffer complemented with 2 mM of Magnesium sulfate. The asymmetric PCR program used is as follows: 94° C., 1 min for the initial denaturation; followed by 30-40 cycles of 94° C., 20 sec; 55-57° C., 30 sec; 68° C., 1 min per kb to amplify. PCR products were run through 1% low melting temperature agarose gel pre-stained with EtBr, at 80 V for 1 h in TAE buffer. The ssDNA bands were extracted and purified using Zymoclean Gel DNA recovery kit. The ssDNA concentration was estimated using the NanoDrop 2000 (Thermo Fisher Scientific, Inc.).

Single Stranded DNA Fragment Larger than 3000 Nts Amplification Using aPCR

While AccuStart HiFi was capable of simple generation of ssDNA products, its processivity was limited to the amplification of large fragments. Initial tests with another Taq-based polymerases NEB LongAmp produced notable amounts of dsDNA byproduct while tested for amplification of the 1000 nts and the 3281 nts fragments. However, these byproducts resolved by increasing the annealing temperature. This enzyme was then tested for use in long ssDNA synthesis. Phage λ genomic DNA (NEB) was used as a template for long-strand synthesis, with the protocol being only slightly modified, including using less template and increasing the extension time commensurate with the product length.

Results

With these optimizations, the LongAmp enzyme was capable of producing ssDNA products 10 and 12 kb in length. Asymmetric PCR amplification of dsDNA Lambda DNA for long ssDNA amplification: The asymmetric PCR was performed with a Mastercycler personal thermal cycler (Eppendorf, Inc.) using a sense primer concentration of 1 μM, an antisense primer concentration of 20 nM and 0.5 ng of Lambda dsDNA template for the 10 kb fragments and 1 ng of Lambda dsDNA template for the 12 kb fragment (Table 3).

Results of the amplification of the two long ssDNA fragments (10 and 12 kb) with the LongAmp [NEB] enzyme were confirmed by agarose gel electrophoresis.

The maximum yield was obtained using 5 unit of LongAmp Taq DNA polymerase in LongAmp Taq reaction buffer complemented with 300 μM of dNTPs mix in a final volume of 50 μL. The asymmetric PCR program used is as follows: 94° C., 30 sec for the initial denaturation; followed by 20-35 cycles of 94° C., 30 sec; 56-60° C., 45 sec; 65° C., 50 sec per kb to amplify. PCR products were run through 0.7-0.8% low melting temperature agarose gel pre-stained with SybrSafe, at 70 V for 2 h in TAE buffer. The ssDNA bands were extracted and purified using Zymoclean Gel DNA recovery kit. The ssDNA concentration was estimated using the NanoDrop 2000 (Thermo Fisher Scientific, Inc.).

Asymmetric PCR amplification of dsDNA GBLOCK®: GBLOCK® were prepared at a concentration of 10 ng/μL in Tris-EDTA buffer. PCR conditions and ssDNA recovery methods were the same as those used for asymmetric PCR on ssDNA plasmid. The hybridization temperature for each primer pair was adjusted for each experiment.

TABLE 2

Oligonucleotide primers and restriction enzymes use to generate ssDNA scaffold strands using aPCR or restriction enzyme digestion.

| Template | Name | Method | 5'-oligos/primers | 3'-oligos/primers | 5' enz | 3' enz | Size (b) |
|---|---|---|---|---|---|---|---|
| M13mp18 ssDNA | PCR 449 | PCR | GTCGTCGTCCCCTCAAACT (SEQ ID NO: 1) | ATTAATGCCGGAGAGGGTAG (SEQ ID NO: 8) | N/A | N/A | 449 |
| M13mp18 ssDNA | PCR 500 | PCR | GGACGCTATCCAGTCTAAACAT (SEQ ID NO: 2) | GAAAGAGGACAGATGAACGGTG (SEQ ID NO: 9) | N/A | N/A | 500 |
| Gblock DsDNA | PCR 721-1 | PCR | GTCGTCGTCCCCTCAAACT (SEQ ID NO: 1) | GCTGAAAAGGTGGCATCAAT (SEQ ID NO: 10) | N/A | N/A | 721 |
| Gblock DsDNA | PCR 721-2 | PCR | GTCGTCGTCCCCTCAAACT (SEQ ID NO: 1) | GCTGAAAAGGTGGCATCAAT (SEQ ID NO: 10) | N/A | N/A | 721 |
| M13mp18 ssDNA | PCR 738 | PCR | CTACCCTCGTTCCGATGCT (SEQ ID NO: 3) | GTTAATGCCCCCTGCCTATT (SEQ ID NO: 11) | N/A | N/A | 738 |
| M13mp18 ssDNA | PCR 750 | PCR | CGCTTTCTTCCCTTCCTTTCT (SEQ ID NO: 4) | GGCGATTAAGTTGGGTAACGC (SEQ ID NO: 12) | N/A | N/A | 750 |
| M13mp18 ssDNA | PCR 769 | PCR | GTCGTCGTCCCCTCAAACT (SEQ ID NO: 1) | GCTGAAAAGGTGGCATCAAT (SEQ ID NO: 10) | N/A | N/A | 769 |
| M13mp18 ssDNA | Frag 893 | Dig | TGGAAAGCGCAGTCTCTGAATTTACCG (SEQ ID NO: 5) | GACTTTTTCATGAGGAAGTTTCC (SEQ ID NO: 13) | BspHI | AlwNI | 893 |
| M13mp18 ssDNA | PCR 1000 | PCR | GTCTCGCTGGTGAAAAGAAA (SEQ ID NO: 6) | ATTAATGCCGGAGAGGGTAG (SEQ ID NO: 8) | N/A | N/A | 1000 |
| M13mp18 ssDNA | PCR 1000-2 | PCR | CTCGGTGGCCTCACTGATTAT (SEQ ID NO: 7) | GCTGCAAGGCGATTAAGTTGG (SEQ ID NO: 14) | N/A | N/A | 1000 |
| GBlock dsDNA | PCR 1087-2 | PCR | GTCGTCGTCCCCTCAAACTC (SEQ ID NO: 15) | GCTGAAAAGGTGGCATCAAT (SEQ ID NO: 10) | N/A | N/A | 1087 |
| M13mp18 ssDNA | PCR 1447 | PCR | TGCCTCAACCTCCTGTCAAT (SEQ ID NO: 16) | AGAGGCATTTTCGAGCCAGT (SEQ ID NO: 24) | N/A | N/A | 1447 |
| M13mp18 ssDNA | PCR 1500 | PCR | GGGCTTGCTATCCCTGAAAAT (SEQ ID NO: 17) | GACTTGCGGGAGGTTTTGAAG (SEQ ID NO: 25) | N/A | N/A | 1500 |
| M13mp18 ssDNA | PCR 1616 | PCR | GCGACGATTTACAGAAGCAA (SEQ ID NO: 18) | AAGGGCGAAAAACCGTCTAT (SEQ ID NO: 26) | N/A | N/A | 1616 |
| M13mp18 ssDNA | Frag 1629 | Dig | TCGTCGCTATTAATTAATTTTCCCTTA (SEQ ID NO: 19) | ACGTGGACTCCAACGTCAAAGGGCGAA (SEQ ID NO: 27) | PacI | drdI | 1629 |
| M13mp18 ssDNA | PCR 2000 | PCR | GATGAGTGCGGTACTTGGTTTA (SEQ ID NO: 20) | GCTTTGACGAGCACGTATAACG (SEQ ID NO: 28) | N/A | N/A | 2000 |
| M13mp18 ssDNA | PCR 2298 | PCR | CTACCCTCGTTCCGATGCT (SEQ ID NO: 3) | CGACGACAATAAACAACATGTTCAGCT (SEQ ID NO: 29) | N/A | N/A | 2298 |
| M13mp18 ssDNA | PCR 2500 | PCR | CACGGTCGGTATTTCAAACCA (SEQ ID NO: 21) | CCTCTTCGCTATTACGCCAGC (SEQ ID NO: 30) | N/A | N/A | 2500 |
| M13mp18 ssDNA | PCR 2805 | PCR | GTCGTCGTCCCCTCAAACT (SEQ ID NO: 1) | GTTAATGCCCCCTGCCTATT (SEQ ID NO: 11) | N/A | N/A | 2805 |
| M13mp18 ssDNA | PCR 3000 | PCR | GCACTGACCCCGTTAAAACTTA (SEQ ID NO: 22) | CAGATTCACCAGTCACACGACC (SEQ ID NO: 31) | N/A | N/A | 3000 |
| M13mp18 ssDNA | PCR 3281 | PCR | TCTTTGCCTTGCCTGTATGA (SEQ ID NO: 23) | GCTAACGAGCGTCTTTCCAG (SEQ ID NO: 32) | N/A | N/A | 3281 |
| M13mp18 ssDNA | PCR 3356 | PCR | GTCTCGCTGGTGAAAAGAAA (SEQ ID NO: 6) | GTTAATGCCCCCTGCCTATT (SEQ ID NO: 11) | N/A | N/A | 3356 |

TABLE 3

Oligonucleotide primers used to generate long ssDNA scaffold strands using aPCR protocol with LongAmp enzyme.

| Template | Name | Method | 5'-oligos/primers | 3'-oligos/primers | Size (b) |
|---|---|---|---|---|---|
| Lambda Phage | PCR 10 kb | PCR | CAGTGCAGTGCTTGATAACAGG (SEQ ID NO: 33) | GTAGTGCGCGTTTGATTTCC (SEQ ID NO: 34) | 10,033 |
| Lambda phage | PCR 12 kb | PCR | CAGTGCAGTGCTTGATAACAGG (SEQ ID NO: 33) | CCGAAGTCGAAATCAAGCTG (SEQ ID NO: 35) | 11,927 |

Single-Stranded DNA Fragment Digestion

The protocol used to cut M13mp18 ssDNA fragments with restriction enzymes was adapted from Said et al., Nanoscale. 5, 284-290 (2013). Briefly, PCR tubes containing approximately 3.5 µg (1.5 pmoles) of M13mp18 ssDNA and 10 molar equivalent of a pair of oligonucleotides (complementary to the two restriction site regions) in 50 µL of 1×NEB CUTSMART® buffer (50 mM potassium acetate, 20 mM Tris-acetate, 10 mM magnesium acetate, 100 ug/mL BSA, pH 7.9) were annealed in a thermal cycler from 85° C. to 25° C. at a rate of 1° C. per min. 10 individual tubes were pooled and 100 units (10 µL) of each restriction enzyme was added directly to the mix. The mix was aged at 37° C. for 3 h. After incubation, each sample was concentrated to 50 µL using an Amicon Ultra-0.5 mL centrifugal filter (MWCO 100 kDa), and run through a 1% low melting temperature agarose gel electrophoresis pre-stained with EtBr. Purification of ssDNA was performed with Zymoclean gel DNA recovery kit. Final ssDNA concentration was determined using the NanoDrop 2000.

aPCR Compared with Single-Stranded DNA Fragment Digestion

The aPCR method used here achieves higher quantities of scaffold with a smaller amount of starting material than the digestion of M13mp18 using restriction enzymes. Briefly, to obtain 3 pmoles of purified product, 5 pmoles of M13mp18 are required using the digestion method while only 0.012 pmoles are needed for aPCR amplification. With aPCR it is also possible to generate many different scaffold lengths, whereas digestion relies on restriction site positions. Table 2 lists the primers used for aPCR amplification, which can be combined as desired to achieve a diverse array of scaffold sizes without generating new primers for each custom length. The final quantity produced in a 50 µL PCR reaction tube is dependent on the fragment size and sequences, ranging between 1.5-4.5 pmoles.

Folding of DNA Origami Objects

DNA Origami Assembly

DNA origami annealing reactions were realized in 50 µL reaction tubes containing the different ssDNA scaffolds in a 5-40 nM concentration range diluted in Tris-Acetate EDTA-MgCl$_2$ buffer (40 mM Tris, 20 mM acetic acid, 2 mM EDTA, 12 mM MgCl$_2$, pH 8.0). To ensure correct folding and to maximize yield, staple strand mixes were added in a 10-20× molar excess. Annealing was performed in a Mastercycler personal thermal cycler (Eppendorf, Inc.) with the following program: 95° C. for 5 min, 80-75° C. at 1° C. per 5 min, 75-30° C. at 1° C. per 15 min, and 30-25° C. at 1° C. per 10 min.

Characterization Methods

Agarose Gel Electrophoresis

Samples were loaded in 2% agarose gel in Tris-Acetate EDTA buffer supplemented with 12 mM MgCl$_2$ and pre-stained with EtBr. Gels were run on a BioRad electrophoresis unit at 4° C. for 3-4 h under a constant voltage of 70 V. Gels were imaged using a Gene flash gel imager (Syngene, Inc.), and yield was estimated by analyzing the band intensity with the Gel Analyzer program in the ImageJ software (Abramoff, M D et al., Biophotonics Int 11, 36-42 (2004)).

qPCR Thermal Analysis qPCR analyses were performed in 384-well plate format using a Roche LightCycler® 480. A typical plate contained at least 3 replicates of each sample. Samples were complemented with 1× final concentration of SYBR Green in a final volume of 20 µL. The scaffold concentration used for the tetrahedron analysis was 80 nM and the concentrations of each strand were adjusted to 1 µM for the three-way junction model. The annealing protocol used was identical to the one used for DNA origami assembly. SYBR® Green fluorescence was monitored over all experiments. Fluorescence curves obtained were analyzed using first-order derivatives to identify transition temperatures.

Results

To investigate the synthetic yield and homogeneity of self-assembled objects programmed using the computationally-generated scaffold and staple designs, asymmetric PCR (aPCR) (Wooddell, et al., Genome Res. 6, 886-892 (1996)) was used to generate object-specific scaffolds for quantitative yield in folding (FIGS. 6A-6B). Agarose gel electrophoresis indicated that digestion of M13mp18 by restriction enzyme produced 1629-b and 893-b fragments, and aPCR amplified a 721-b ssDNA strand. These custom scaffolds minimize excess single-stranded DNA in the final structure, which may result in non-specific object aggregation or otherwise interfere with folding as well as downstream chemical functionalization (FIGS. 7A-7E, and FIGS. 8A-8B) (Rothemund, Nature., 440, 297-302 (2006); Dunn, K E et al., Nature. 525, 82-86 (2015); Sobczak, J P J et al., Science. 338, 1458-1461 (2012)).

Monodispersity of multiple custom linear short scaffold strands synthesized ranging from 450 to 3,400 nucleotides were first confirmed using gel electrophoresis of aPCR products based either on the M13pm18 ssDNA plasmid or dsDNA fragments as templates. Custom scaffolds were used to fold tetrahedra of 31-, 42-, 52-, 63-, and 73-bp edge lengths in addition to an octahedron, two pentagonal bipyramids (42- and 52-bp edge lengths), a cube, a reinforced cube, an icosahedron, and a cuboctahedron. Agarose gel electrophoresis confirmed their high folding yield of approximately 60-90% (Table 4) and particle homogeneity that is characteristic of scaffolded DNA origami objects. Importantly, application of this aPCR approach offers folded sample purity that is similar to existing synthesis strategies that utilize restriction enzymes to generate sub-fragment scaffolds (FIGS. 7A-7E) (Said, H et al., Nanoscale. 5, 284-290 (2013)), yet without dependence on restriction sites and with higher synthetic yield.

Redesign of vertex staple nicks to be positioned at crossovers instead of interior segments of duplexes also resulted in increased folding stability (FIGS. 9A-9H). Thus, diverse polyhedral origami objects from 200 kDa to 1 MDa programmed using this top-down, inverse sequence design procedure self-assembled robustly using scaffolds of custom length and sequence, which may be natural or synthetic.

TABLE 4

Folding yield from 2% agarose gel electrophoresis for the different DNA objects.

| DNA origami objects | Edge length (bp) | Folding yield on agarose gel (%) |
|---|---|---|
| Tetrahedron | 31 | 90 |
| Tetrahedron | 42 | 78 |
| Tetrahedron | 52 | 93 |
| Tetrahedron | 63 | 91 |
| Tetrahedron | 73 | 91 |
| Octahedron | 52 | 72 |
| Cube | 52 | 60 |
| Reinforced cube | 52 | 84 |
| Cuboctahedron | 52 | 88 |
| Icosahedron | 52 | 74 |
| Pentagonal bipyramid | 42 | 87 |
| Pentagonal bipyramid | 52 | 83 |

Example 4: Verification of Structural Fidelity of Programmed DNA Origami

DNA nanoparticles of expected sizes and shapes were used to generate 3D density maps, and the structures of nanoparticles were validated using cryo-EM. Structural data for nanostructures designed and folded using the described methods are available at the EMDB (electron microscopy databank), as accession numbers EMD-3408 (Tetrahedron); EMD-3409 (Icosahedron); EMD-3410 (Octahedron); EMD-3411 (Cuboctahedron); EMD-3412 (Reinforced cube); and EMD-3413 (Nested cube).

Importantly, cryo-EM reconstructions confirmed that origami objects assembled as designed instead of "inside-out" while satisfying programmed Watson-Crick base pairing from sequence design. This result reaffirms the suitability of the sequence design formula to choose to point the major groove inwards at vertices, which was based on the previous observation that DNA origami folds in this manner (He, Y et al., Angew. Chem. 122, 760-763 (2010)).

Example 5: Stability of DNA Origami Assembly in Various Salt Conditions

Methods and Materials
  Buffer Exchange and Stability Experiments
  Buffer Exchange DNA origami objects were folded in TAE-Mg buffer (12 mM $MgCl_2$) and washed one time with TAE-Mg (12 mM $MgCl_2$) buffer using Amicon Ultra-0.5 mL centrifugal filter (MWCO 100 kDa) and subsequently washed three times with the new stability buffer (TAE, PBS, or DMEM+FBS).
  Stability Experiments The stabilities of DNA origami objects in TAE, PBS, or DMEM FluoroBrite (0.35% BSA, 1% Penicillin/Streptomycin, 1% L-Glutamine) buffer complemented with 2% dialyzed fetal bovine serum (dFBS) or 10% FBS were evaluated for 6 h.

Results

Figure 10A:
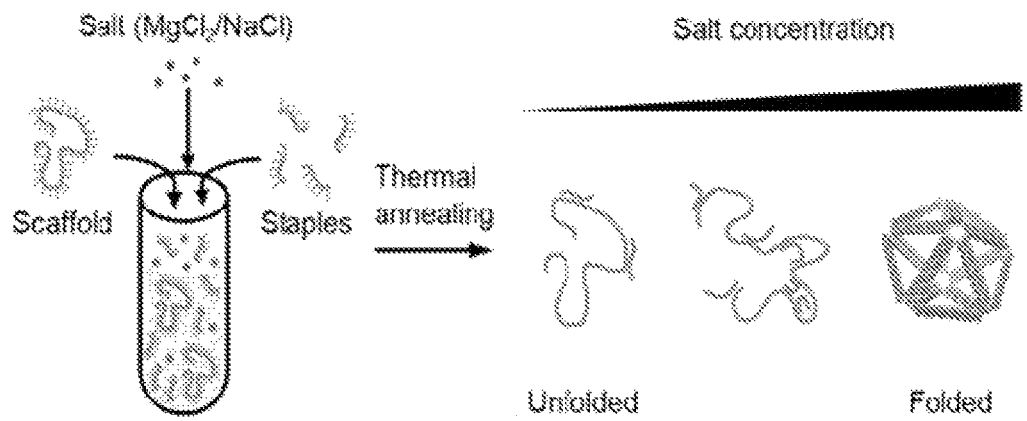
FIGS. 10A-10B are schematics illustrating characterization of DNA origami folding in variable salt and stability in physiological buffer and serum.
Figure 10B:
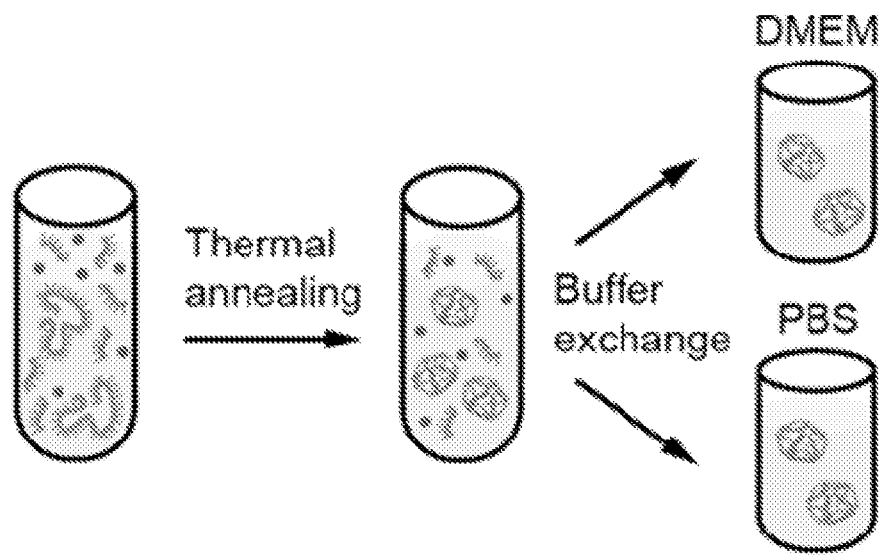

An important limitation of DNA origami for biological as well as in vitro applications has been the requirement of high concentrations of either magnesium or monovalent cations for their folding and stability (Martin, T G et al., Nat. Commun. 3, 1103 (2012); Sobczak, J P J et al., Science. 338, 1458-1461 (2012)), which was recently shown to be alleviated by the use of single-duplex edge mesh-works that fold and are stable in physiological buffer and salt conditions (Yan, H et al., Science. 301, 1882-1884 (2003)). Folding of 52-bp edge-length pentagonal bipyramid in increasing magnesium chloride ($MgCl_2$) concentrations including 1 mM, 2 mM, 4 mM, 6 mM, 8 mM, 12 mM, 16 mM, 20 mM, 30 mM; and increasing sodium chloride (NaCl) concentrations including 10 mM, 20 mM, 50 mM, 100 mM, 150 mM, 200 mM, 500 mM, 1 M, and 2 M, was characterized by 2% agarose gel electrophoresis. Similar analysis was conducted on folding of 63-bp edge-length DNA tetrahedron. Stability of the 52-bp edge-length pentagonal bipyramid, after being folded in TAE-Mg (12 mM $MgCl_2$) buffer, followed by buffer exchange for 6 hours in PBS, TAE (without added NaCl or $MgCl_2$), or DMEM buffer with increasing concentration of FBS (0, 2, and 10%), was characterized using 2% AGE. Stability was observed for structures in PBS buffer but not in the absence of salt in TAE, which clearly demonstrates the importance of minimal salt concentration for stability. While degradation is observed for structures in DMEM media in the presence of 2 to 10% FBS, the presence of intact objects was detected after 6 hours. In summary, investigation of the folding properties of these synthesized DX-based objects revealed that objects fold effectively in cation concentrations as low as 4 mM $Mg^{2+}$ and 500 mM $Na^+$ (FIG. 10A), as well as in PBS alone (FIG. 10B). The use of DX-arms and multi-way junctions here uniquely results in structurally stable, rigid assemblies that are crucial to most applications (Rothemund, P W, Nanotechnology: Science and Computation. 3-21 (2006); Yan, H et al., Science. 301, 1882-1884 (2003)).

To test the utility of these objects for cellular assays, post-folding in TAE-$MgCl_2$ particles were transferred to PBS and Dulbecco's Modified Eagle's Medium (DMEM) containing 0 to 10% FBS, where they were found to be stable for at least six hours (FIG. 10B). When transferred to salt-free solution post-folding, however, particles were observed to be unstable, confirming the importance of a minimal amount of added salt for their longer-term stability (FIG. 10B). Interestingly, folding of the 52-bp tetrahedron using the full M13 scaffold instead of its custom scaffold also required higher magnesium concentrations to achieve folding, reaffirming the importance of the use of scaffolds that eliminate excess in single-stranded DNA (FIGS. 9A-9B).

As a major advance in this direction, a top-down, geometry-driven sequence design procedure is developed that uses a spanning tree formula to determine scaffold crossover positions, which enables efficient and unique routing of the single-stranded scaffold throughout the target origami object, as well as automated staple assignment for custom synthesis of programmed origami objects of quantitative yield and high fidelity atomic-level structure. Asymmetric PCR provides full control over scaffold sequence and length, and use of the DX-based design further confers folding capacity and stability under diverse conditions including cell-compatible buffers. Combined, this strategy to realize the top-down design of nanoscale DNA assemblies offers full control over both 3D structure and local sequence which, together with the broadly usable software and experimental protocols, provides a versatile approach to the design of functionalized DNA objects of nearly arbitrary shape for numerous applications in biomolecular science and nanotechnology including nanoparticle delivery (Bhatia, D et al., Angew. Chem. Int. Ed. 48, 4134-4137 (2009); Douglas, S M et al., Science. 335, 831-834 (2012)), photonic applications (Sun, W et al., Science. 346, 1258361 (2014); Kuzyk, A et al., Nature. 483, 311-314 (2012)) that include self-assembled super-lattices (Liu, W et al., Science. 351, 582-586 (2016)), inorganic nanoparticle synthesis (Sun, W et al., Science. 346, 1258361 (2014)), memory storage (Church, G M et al., Science. 337, 1628-1628 (2012)), and single-particle cryo-EM analysis (He, Y et al., Nature. 452, 198-201 (2008); Bai, X et al., Proc. Natl. Acad. Sci. 109, 20012-20017 (2012); Wang, Z et al., Nat. Commun. 5, 4808 (2014); Irobalieva, R N et al., Nat. Commun. 6, 8440 (2015)) for proteins and RNAs that are not otherwise amenable to crystallography or NMR, amongst other applications (Jones, M R et al., Science. 347, 1260901 (2015)). The ability to synthesize nearly arbitrary geometric shapes that are automatically rendered from the top-down should enable the broad participation of non-experts in this powerful molecular design paradigm.

Example 6: Single Stranded DNA Fragment Amplification Using Modified dNTPs

Methods and Materials

Amplification of Single Stranded DNA Fragments with Modified dNTPs

The methods for production of single-stranded nucleic acid scaffold sequences using APCR can be adapted to incorporate modified dNTPs, for example, for the production of nanoparticles including custom-designed modifications to nucleic acids.

Asymmetric PCR (aPCR) amplification with Accustart HiFi was used to amplify ssDNA fragment using various percentage of modified dNTPs. Each dNTP was prepared separately at a concentration of 100 mM, and mixed prior to amplification at the correct ratio.

dUTPs were used in a 1 to 100% range to replace dTTP. Cy5-dCTP was used in a range of 1-10%. Alpha-phosphate-dNTP was used from 1 to 100% to replace all the four non-modified bases.

The protocol used for amplification is the same as for normal fragment amplification with Accustart HiFi. Exemplary synthesis of ssDNA with APCR using modified dNTPs for nanoparticle folding was carried out by amplification of a 1,000 nts fragments with a different percentages of thitriphosphate-modified dNTPs (i.e., ranging from 0%-100% alpha-phosphate dNTPs).

Protection and Stability Assay

Nanoparticles formed using staples modified at their 3' and 5' ends by phosphorothioate were assembled, purified, and incubated in different percentages (0%, 2%, 5% and 10%, respectively) mouse serum to assess degradation.

The results were visualized using gel electrophoresis of nanoparticles in equal starting molar amounts. A reduction in the intensity of the bands on the gel was indicative of nuclease protection.

Results

A single-stranded nucleic acid of 1,000 nts in length was amplified using asymmetric polymerase chain reaction (aPCR) fragments with different percentage of alpha-phosphate dNTPs. Bands at 1,000 nts were visualized at the corresponding molecular weight on an agarose gel for APCR products prepared to incorporate 0% (control) 10%, 20%, 40%, 50% and 75% thiotriphosphate-modified dNTPs.

Use of dUTP at different percentages (90% total, 95% total and 100% total) to replace dTTP for amplification of a 1,000 nts ssDNA fragments with aPCR was also confirmed by visualizing of products having the corresponding molecular weight on an agarose gel.

Figure 11:
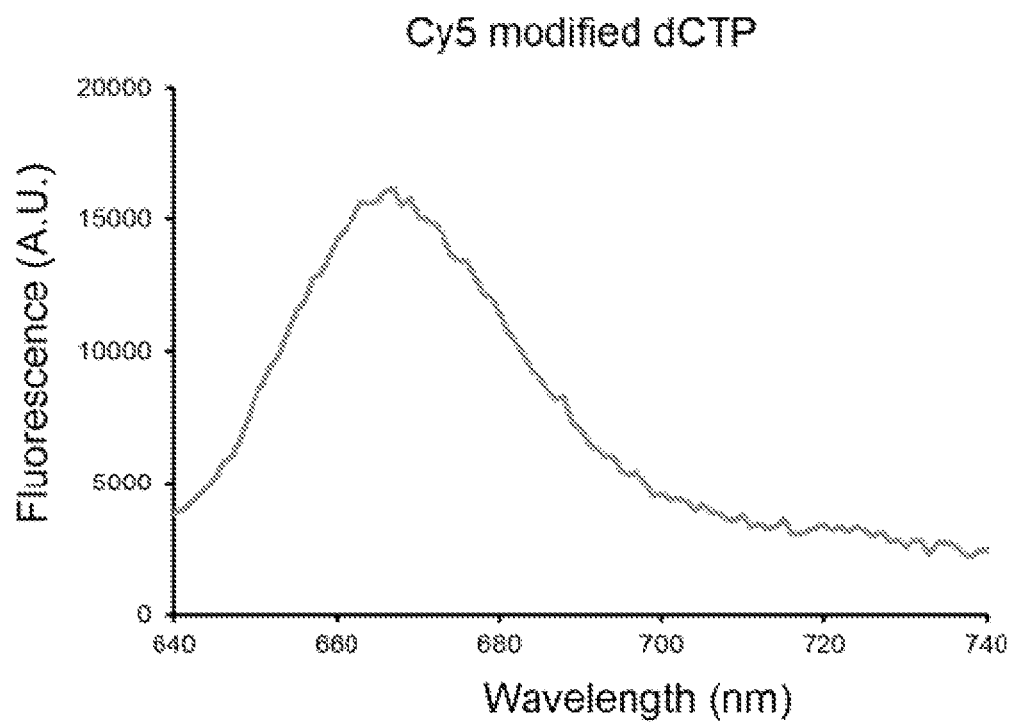
FIG. 11 is a graph showing fluorescence (A.U) over wavelength (nm) for nucleic acid scaffolds of 2,000 nt, produced using a 10% concentration of Cy5-modified dCTP in aPCR.
Figure 12A:
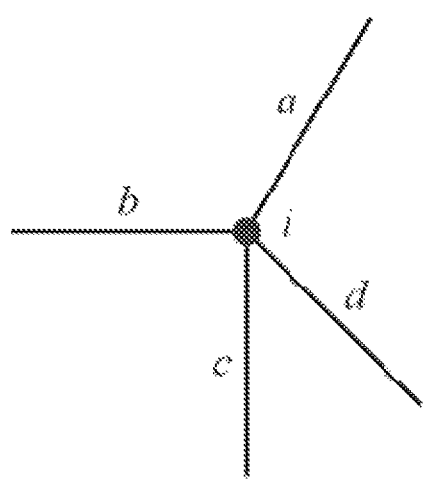
FIGS. 12A-12E are schematic representations of each of 5 depictions showing how the edge length of two adjacent edges at the i-th vertex are modified when the angle between two edges is relatively larger than others.
Figure 12B:
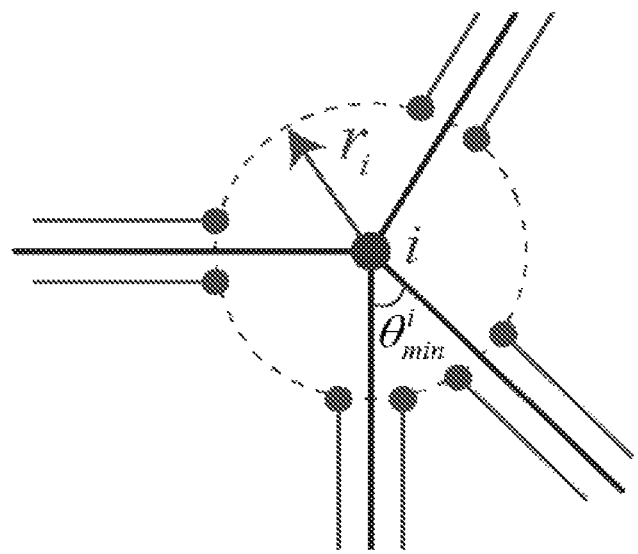
Figure 12C:
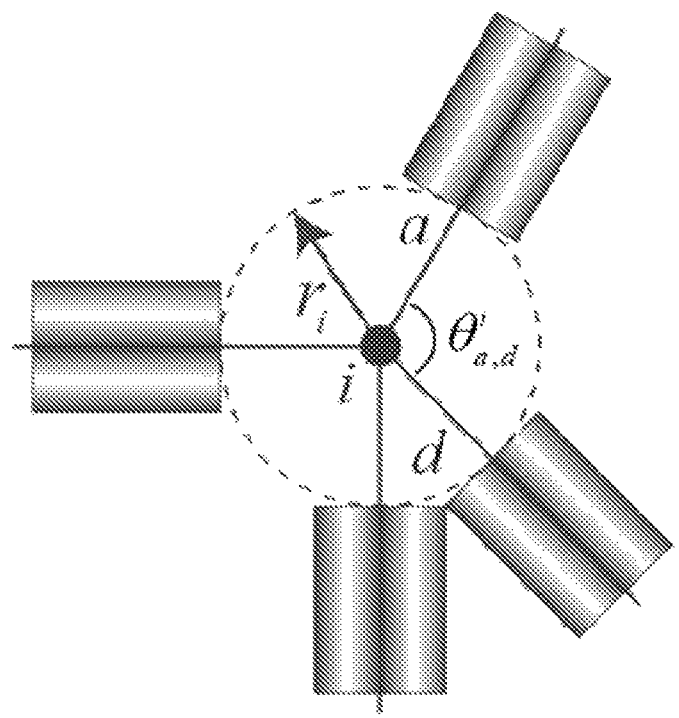
Figure 12D:
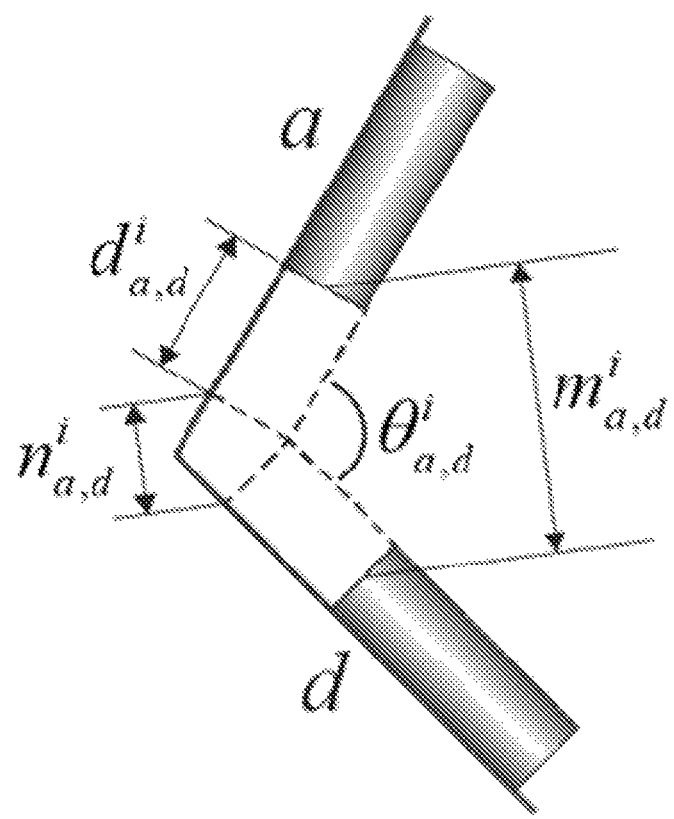
Figure 12E:
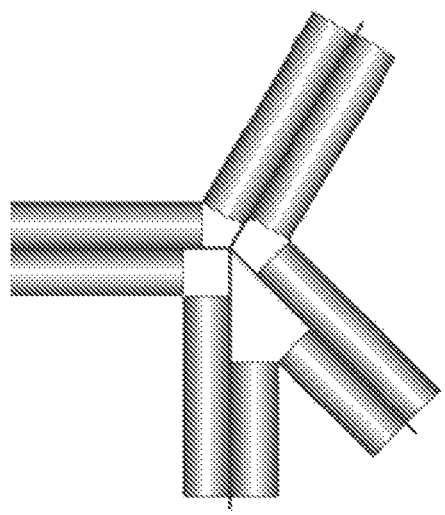

Production of fluorescent ssDNA fragments of 2,000 nts by incorporating different concentrations of Cy-5 dCTP was also demonstrated by aPCR (see FIG. 11).

Specifically, Cy5-modified dNTPs were incorporated into the 2,000 nt scaffold strand at concentrations ranging from 0.5%-10% Cy5, including 0.5%, 1%, 2%, 5%, and 10%, confirmed by visualizing of products having the corresponding molecular weight on an agarose gel and also by fluorescence spectroscopy of the resulting nucleic acid sequence. The Cy5-modified scaffold nucleic acid including 10% Cy5 was folded into a polyhedral shape according to the described methods. Folded fluorescent nucleic acid nanostructures were visualized as a gel-shifted band as visualized on an agarose gel.

The protection assay indicated that nanoparticles incorporating phosphorothioate-modified nucleic acids were less-prone to exonuclease digestion in mouse serum than those that did not in incorporate the modified nucleic acids.

Example 7: Conjugation of Molecules to Nucleic Acid Nanostructures

Methods and Materials

Experiments to demonstrate the use of nucleic acid nanostructures for the capture of other molecules were also carried out. In one experiment, an RNA (mRNA encoding mCherry protein, transcribed by T7 RNA polymerase and acrylamide gel purified) molecule was fixed to a tetrahedral nanostructure with 63 base pair edge length using single strand DNA overhangs extended from the staples at nick positions, with the sequence of the overhang complementary to predicted loops in the RNA structure (depicted in FIG. 16 A).

The conjugation of nucleic acid nanostructures to target molecules was confirmed by gel electrophoresis, and the identity of the bound target material was also validated using cryo-electron microscopy (cryo-EM).

In a second experiment, the CRISPR enzyme Cpf1 with crRNA was captured onto a DNA nanoparticle, by conjugation to a sequence on a crossbeam structure built into the nanoparticle. The capture was mediated by a nucleic acid sequence targeted by the Cpf1/crisprRNA enzyme (depicted in FIG. 16 B). The DNA template for the crRNA was synthesized by complementary oligonucleotide completion and purification followed by transcription using T7 RNA polymerase using the MegaShortScript transcript kit (Invitrogen). The crRNAs were purified using acrylamide gel purification followed by column purification (Qiagen RNAeasy kit). ALT-R CRISPR-Cpf1 (IDT) was incubated with equimolar concentration of the crRNA of interest. Two Cpf1 targets for EGFP were generated (CCTGGTCGAGCTGGACGGCGACG (SEQ ID NO:36); CTGAGCACCCAGTCCGCCCTGAG (SEQ ID NO:37)), and those same sequences were placed in the center region of the crossbeam across the tetrahedron with 84 base pair edge length. The pre-incubated Cpf1/crRNA complex was then added in 1.5 molar excess to 40 nM tetrahedron-crossbeam nanoparticles and incubated for 30 minutes at 37° C. and immediately placed on ice. The resulting complex was ran on a 2% high-resolution agarose gel stained with INVITROGEN SYBR®SAFE at 65V for 4 hrs at 4° C. Band shift due to complexed protein was indicated by less migration through the gel. Subsequently the gel was stained in Coomassie blue and destained in 10% acetic acid 30% ethanol. Co-staining indicated comigration of protein with the nanoparticle.

In a third experiment, the CRISPR enzyme Cpf1 with crRNA was captured onto a DNA nanoparticles by conjugation onto an overhang sequence built into the nanoparticle, which contains a sequence complementary to a 3' extension of the crRNA (depicted in FIG. 16 C). As above, the crRNA was transcribed using T7 RNA polymerase MegaShortScript (Invitrogen) with additional sequences 3' of the crRNA and purified as before. The RNA was complexed to the Cpf1 by incubation at 37° C. and annealed to a tetrahedron with 84 base pair edge length with one staple extended 3' with a single stranded DNA overhang reverse-complementary to the crRNA overhang. The Cpf1/crRNA was added in 1.5 molar equivalents to 40 nM tetrahedron and annealed from 42° C. to 22° C. over 1 hr then placed on ice. The sample was then loaded to a 2% high resolution agarose gel and ran and stained as described above.

Results

The RNA bound to the nanoparticle was seen by an increase in molecular weight using gel electrophoresis, as a slower migration inducing a shift of the band on the gel. The bound RNA was also validated using cryo-electron microscopy.

ALT-R CRISPR-Cpf1 with crRNA targeting a sequence in EGFP was attached to a crossbeam containing 20 nucleotides of that target sequence (thus the reverse complement of the targeting crRNA sequence), was indicated by the induced gel shift in the corresponding lane, as compared with both substrate molecules alone. Further validation of the binding between ALT-R CRISPR-Cpf1 with crRNA and the nanostructure was observed through co-localization of the protein material when stained with Coomassie blue dye.

Alt-R CRISPR-Cpf1 with crRNA targeting a sequence in EGFP with a 3' sequence extension of 14 nucleotides was attached to an overhang containing a complementary sequence of 14 nucleotides, as determined by the induced gel shift in the bound lane. Further validation of the binding is seen through co-localization of protein material when stained with Coomassie blue.

Accordingly, conjugation of nanostructures with target molecules produced by top-down design was confirmed.

Example 8: Scaffolded RNA Nanostructures

Methods and Materials

Nucleic acid nanostructures incorporating RNA as the single-stranded scaffold were designed and produced according to the described methods for top-down design for DX staple structures. The methods used to generate DNA-scaffolded DX-tile nanoparticles with two helices per edge were applied to design and produce a RNA-scaffolded tetrahedron with 66 base pairs edge length. The same scaffold routing procedure was used, with the edges modified to extend to the multiple of 11 base pairs. Similarly, an RNA-scaffolded octahedron with 44 base pairs edge length was also generated.

The RNA scaffold was synthesized using a template generated from a 1058 nucleotide segment of the M13mp18 DNA with an additional T7 promoter added to the 5' primer. T7 RNA polymerase was used to synthesize the RNA which was gel purified from polyacrylamide and column purified (Qiagen RNAeasy kit). The purified RNA was mixed with 20-fold excess staples in a buffer composed of 100 mM HEPES-NaOH and 200 mM NaCl and slowly annealed over 24 hours.

Folding and assembly of the nanoparticles were determined by gel electrophoresis on 2.5% high resolution agarose in 1×Tris-borate-EDTA supplemented with 2.5 mM $MgCl_2$ and ran at 65V for 3 hours at 4° C. The band was compared against single-stranded RNA scaffold alone. The structure was using an Amicon 100 k MWCO spin filtration column spun at 3000 RPMs for 20 minutes and buffer exchanged by returning to original volume 5 times. The particles were imaged using transmission electron microscopy by fixing to carbon grids, drying, and negative staining with 2% uranyl acetate.

Results

The RNA nanostructures were assembled and folded, as visualized by the gel shift migration between the scaffold and the folded particle.

The resulting nanoparticles were structurally characterized by transmission electron microscopy, the electron micrograph confirming the structures were assembled and folded according to the design criteria.

This example demonstrated that the methods can be applied to RNA nanoparticles.

Example 9: HIV-1 RNA Genome Fragments Captured on DNA Nanostructures

To overcome the major gap in the knowledge of 3D structures of viral RNAs, a novel technical platform is implemented for the high-throughput and high-resolution determination of the 3D structure of RNAs, with application to the HIV-1 RNA genome. Application to the HIV-1 genome structure offers basic insight into the general principles of RNA folding, with future potential also for programming RNA structures for biotechnological applications.

The methods developed for determination of the 3D structure of RNAs are generally applicable to solving any 3D RNA structures, with downstream application to diverse viral genomes in addition to messenger RNAs, long non-coding RNAs, as well as other important classes of RNAs that play a central role in biology and disease. This structural knowledge is essential to understanding the diverse biological functions of RNAs including messaging, splicing and modification, protein interactions, translation regulation, catalysis, and genetic inheritance.

Methods and Materials

T7 RNA polymerase was used to transcribe RNA from double-stranded DNA templates encoding for the 5'UTR and the RRE. These constructs had a 5' T7 RNA polymerase promoter followed directly into the sequence. Transcription was done using the T7 megascript kit (Invitrogen). RNA was then purified on 8% polyacrylamide gel by separating contaminates and extraction by diffusion into 300 mM Sodium acetate. The RNA was the precipitated in 70% ice cold ethanol and placed at −20° C. overnight. The precipitant was pelleted in a Epindorf centrifuge running at 14,000 rpms for 30 minutes. The pellet was re-suspended in $H_2O$. The RNA was then further cleaned by use of a QIAGEN RNA purification kit. Prior to binding, the RNA was heated to 65° C. for 3 minutes and then put on ice. 5× concentrated folding buffer (250 mM HEPES pH 7.6, 750 mM NaCl, 37.5 mM $MgCl_2$) was added to 1× final, and the RNA was placed at 37° C. for 1 hour.

DNA oligonucleotides were purchased from IDT that had complementary sequences to the targeted loops and an additional set of nucleotides that are complementary to a second biotinylated strand. The two DNA oligonucleotides were annealed in 50 mM HEPES, 150 mM NaCl, and 7.5 mM MgCl$_2$ by heating to 95° C. and cooling stepwise to 25° C. over 1 hour. The annealed strands were then affixed to streptavidin coated magnetic beads (NEB). Excess duplex strands were removed by washing. RNA was then added and incubated with the beads coated in duplex DNA containing a region of single-stranded capture or bait sequence with RNA in 5-fold molar excess, with incubation at 37° C. for 10-15 minutes followed by incubation at room temperature for 10-15 minutes. Excess RNA was washed. The beads containing bound duplex DNA and bound RNA were then exchanged to water and DNA and RNA was removed by incubation at 65° C. for 5 minutes, and beads pulled down by magnets. The eluate was then run on a denaturing polyacrylamide gel and RNA was visualized by staining with INVITROGEN SYBR®SAFE.

Tetrahedra were assembled with non-functionalized staples except for 3 staples, which were replaced by functionalized staple with either a 5' or 3' locked nucleic acid sequences that are complementary to the RNA single strand loop of the 5'TAR and one strand was replaced in both tetrahedral by a functionalized strand with a biotin moiety. The scaffold sequence was incubated with 10-fold excess of staple strands and annealed over 14 hours from 95° C. to 25° C. The tetrahedra were purified by Amicon 100 kd MWCO spin filters and buffer exchanged to 50 mM HEPES pH 7.6, 150 mM NaCl, and 7.5 mM MgCl2. In different wells the tetrahedra were incubated with streptavidin coated magnetic beads (NEB) and then brought down with a magnet and washed four times. The folded RNA was then incubated with the tetrahedra-bead system for 20 minutes at 37° C., 20 minutes at 30° C. and ~30 s at room temperature. The beads were brought down by a magnet and subsequently washed 5 times. The tetrahedra and RNA were released by bringing the beads up in water and heating at 65° C. The released solution was ran on a denaturing polyacrylamide gel and visualized in UV after staining with INVITROGEN SYBR®SAFE.

Results

RNA capture experiments using sequence-specific ssDNA overhangs to bind the target RNA towards solving structures are successfully carried out. DNA fragments were amplified from the HIV-1 genome plasmids p83-2 and p83-10 sequences from the NIH AIDS Reagent Program. DNA fragments encoding the whole 5'-UTR (nucleotides 1-346; FIGS. 5A-5F) and an engineered version of the 5'UTR with the long single-stranded primer binding site replaced by a short tetraloop, as used in NMR studies (Keane, S C et al., *Science.* 348, 917-921 (2015)), were amplified with a 5' T7 RNA polymerase promoter, in addition to the Rev Response Element (RRE). RNA was then transcribed with the T7 RNA polymerase, gel purified, and refolded in a previously published buffer (Watts, J M et al., *Nature.* 460, 711-716 (2009)). The polyacrylamide gel verified RNA production of full-length 5'-UTR (WT), 5'-UTR with the primer binding site truncated to a tetraloop (PBS), with the RRE used for size comparison. The transcribed, folded RNA was subjected to bead-based binding assays against immobilized DNA. A biotin-DNA duplex strands containing single-stranded overhang complementary to the single-stranded loops of the RNA, as judged by previously published SHAPE analysis from the Weeks lab (Watts, J M et al., *Nature.* 460, 711-716 (2009); Siegfried, N A et al., *Nature Methods.* 11, 959-965 (2014)) were tested for their ability to bind RNA. The DNA duplexes were bound to beads and then RNA was incubated with the bait-duplex covered beads. These were then washed, and any bound RNA was released by heating and loading to a denaturing urea polyacrylamide gel. Positive capture was seen for 4 different targets out of the 5 tested overhang sequences, including the TAR loop, the unpaired 5'-pseudoknot, a loop near the packaging signal, and the gag/pol Kozak sequence. The bait sequence complementary to the dimerization site sequence was unable to capture the RNA, likely due to dimerization blocking the binding.

Two tetrahedra of length 63 bp were assembled that each had a single strand overhang targeting the TAR loop incorporated into them in opposite orientations. These tetrahedra were additionally built to incorporate a biotin moiety on a separate staple strand overhang, opposite in space from the bait sequence. Streptavidin bead-based capture was then used to capture the tetrahedra and this was used for subsequent RNA binding. Release of RNA by heating, and loading to a polyacrylamide gel showed the tetrahedron was able to capture the RNA in both orientations of the overhang sequence targeting the TAR loop.

A platform to capture large RNA fragments using DNA nanostructures has been established. Assembling multiple bait sequences onto the nanostructures will allow capture of diverse RNA fragments.

We claim:

1. A method for making a nucleic acid nanostructure having a geometric shape comprising:
   (a) providing or determining the geometric parameters of an input, wherein the input comprises a 3D polyhedral or 2D polygonal geometric shape of a target nucleic acid nanostructure;
   (b) identifying a route for a single-stranded nucleic acid scaffold that traces throughout the geometric shape comprising:
      rendering a wireframe mesh of the geometric shape as a node-edge network;
      using a spanning tree of the node-edge network to define the placement of scaffold crossovers; and
      determining a Euler cycle, wherein the single-stranded nucleic acid scaffold traces the Euler cycle throughout the node-edge network;
   (c) assembling the target nucleic acid nanostructure having the 3D polyhedral or 2D polygonal geometric shape comprising hybridizing the single-stranded nucleic acid scaffold to itself and/or staple strands to form the target nucleic acid nanostructure designed according to steps (a) and (b).

2. The method of claim 1, wherein the input in step (a) further comprises one or more of the target nucleic acid nanostructure's physical parameters.

3. The method of claim 1, wherein the input in step (a) further comprises specifying an even number of parallel or anti-parallel helices within each edge of the nanostructure.

4. The method of claim 3, wherein each edge comprises four or more parallel or anti-parallel helices arranged in square cross-sectional morphology, or six or more parallel or anti-parallel helices arranged in honeycomb lattice morphology.

5. The method of claim 4, wherein the input in step (a) further comprises specifying for each vertex of the nanostructure that two or more edges come together in an aligned angle to create a bevel at the vertex.

6. The method of claim 1, wherein the geometric shape does not have spherical topology.

7. The method of claim 1, wherein the input in step (a) further comprises a template nucleic acid scaffold sequence, the sequence of one or more staple strands, or a template nucleic acid scaffold sequence and the sequence of one or more staple strands.

8. The method of claim 1, wherein the input in step (a) further comprises the length of one or more of the edges spanning two vertices of the target nucleic acid nanostructure.

9. The method of claim 8, wherein the input in step (a) further comprises
   specifying that the crossovers are antiparallel crossovers and/or parallel crossovers,
   specifying the form of the nucleic acid scaffold and/or staple strands as DNA or RNA,
   specifying the sequence and/or length of the nucleic acid scaffold and/or staple strands,
   or any combination thereof.

10. The method of claim 9, wherein the crossovers are is anti-parallel crossovers,
    wherein the target nucleic acid nanostructure comprises B-form nucleic acid helices along the edges,
    wherein the length of each edge is expressed as a multiple of 10.5 base pairs rounded up or down to the nearest whole number, and
    wherein the length of each edge is between 21 base pairs and 1,000 base pairs, inclusive.

11. The method of claim 9, wherein the crossovers are anti-parallel crossovers,
    wherein the target nucleic acid nanostructure comprises A-form nucleic acid helices along the edge,
    wherein the length of each edge is expressed as a multiple of 11 base pairs, and wherein the length of each edge is between 22 base pairs and 1,100 base pairs, inclusive.

12. The method of claim 9, wherein the crossovers are parallel crossovers, and
wherein the target nucleic acid nanostructure comprises A-form or B-form nucleic acid helices along the edges, and
wherein the length of each edge is between 20 base pairs and 1,100 base pairs, inclusive.

13. The method of claim 9, wherein the target nucleic acid nanostructure comprises A-form or B-form nucleic acid helices along the edge, and
wherein the length of each edge is 21 base pairs, 31 base pairs, 42 base pairs, 52 base pairs, 63 base pairs, or 73 base pairs.

14. The method of claim 9, wherein the nucleic acid scaffold is RNA the staple strands are RNA or the scaffold and staple strands are RNA, and
wherein the length of each edge is 44 base pairs, 55 base pairs, 66 base pairs, or 77 base pairs.

15. The method of claim 1, wherein the input in step (a) comprises geometric parameters including vertex, face and edge information determined from a polygonal or polyhedral wire-mesh model of the geometric shape.

16. The method of claim 1, wherein identifying the route for the single-stranded nucleic acid scaffold that traces throughout the geometric shape in step (b) further comprises classifying each edge of the network based on its membership in the spanning tree,
wherein edges that are members of the spanning tree do not have a scaffold double crossover, and edges that are not members of the spanning tree have a scaffold double crossover;
splitting each edge that is not a member of the spanning tree into two edges, each containing a pseudo-node at the point of the scaffold crossover;
splitting each node at each of the vertices into two pseudo-nodes; and
wherein the Euler cycle represents a route of the single-stranded nucleic acid scaffold that traces once along each edge in both directions throughout the entire geometric shape.

17. The method of claim 16, wherein the spanning tree of the network is determined using a breadth-first search or depth-first search.

18. The method of claim 17, wherein the spanning tree is calculated using Prim's formula or Kruskal's formula.

19. The method of claim 16, wherein the Euler cycle is the A-trail Euler cycle.

20. The method of claim 16, wherein the geometric shape is a 3D polyhedral .

21. The method of claim 20, further comprising predicting the three-dimensional structure of the nucleic acid nanostructure.

22. The method of claim 21, wherein the nucleic acid nanostructure is validated by comparison with the predicted three-dimensional structure.

23. The method of claim 1, wherein identifying the route for the single-stranded nucleic acid scaffold that traces throughout the geometric shape in step (b) further comprises classifying each edge of the network as one of four types based on its membership in the spanning tree and on whether it employs anti-parallel or parallel crossovers, wherein edges that are members of the spanning tree have each scaffold portion start and end at different vertices, and edges that are not members of the spanning tree have each scaffold portion start and end at the same vertex;
splitting each edge that is not a member of the spanning tree into two edges, each containing a pseudo-node at the point of the scaffold crossover;
splitting each node at each of the vertices into two pseudo-nodes; and
wherein determining the Euler cycle comprises superimposing and connecting units of partial scaffold routing within an edge based on its classification and length.

24. The method of claim 1, wherein identifying the route for the single-stranded nucleic acid scaffold that traces throughout the geometric shape in step (b) further comprises:
rendering each helix in the network as a line based on a target cross-section of each edge;
calculating a loop-crossover structure, wherein two or more adjacent lines are connected to form loops and all possible double-crossover locations between two loops are calculated;
calculating a dual graph of the loop-crossover structure, wherein the loops and double-crossover locations of the network are converted to nodes and edges of the dual graph, respectively, wherein the spanning tree is of the dual graph network;
calculating which of the locations of double-strand crossovers will be used, wherein a single double-strand crossover is placed at each edge that is the part of the spanning tree of the dual graph; and
wherein the Euler cycle represents a route of the single-stranded nucleic acid scaffold that traces once through each duplex throughout the entire geometric shape.

25. The method of claim 24, wherein the nucleic acid nanostructure comprises four or more nucleic acid anti-parallel helices spanning each edge of the nucleic acid nanostructure,
wherein the three-dimensional structure is formed from single-stranded nucleic acid staple strands hybridized to the single-stranded nucleic acid scaffold,
wherein the Euler cycle is defined by vertices and lines of the node-edge network,
wherein the nucleic acid nanostructure comprises at least one edge including a double strand crossover,
wherein the location of the double strand crossover is determined by a spanning tree of the dual graph of the network of the polyhedral or polygonal structure,
wherein the helices comprising an edge are arranged as a square lattice of four or more helices, or honeycomb lattice of six or more helices,
wherein the helices meeting at a vertex are beveled or non-beveled, and
wherein the staple strands are hybridized to the vertices, edges and double strand crossovers of the scaffold to define the shape of the nanostructure.

26. The method of claim 1, further comprising validating the nucleic acid nanostructure.

27. The method of claim 1, wherein the nucleic acid nanostructure comprises two nucleic acid anti-parallel helices spanning each edge of the structure,
wherein the three-dimensional structure is formed from single-stranded nucleic acid staple strands hybridized to the single-stranded nucleic acid scaffold,
wherein the Euler cycle is defined by vertices and lines of the node-edge network,
wherein the nucleic acid nanostructure comprises at least one edge including a double-strand crossover,
wherein the location of the double-strand crossover is determined by the spanning tree of the node-edge network, and wherein the staple strands are hybridized to the vertices, edges and double strand crossovers of the scaffold to define the shape of the nanostructure.

28. The method of claim 27, wherein a single-stranded or double-stranded nucleic acid overhang extends from a nick position on one or more of the staple strands.

29. The method of claim 28, wherein one or more of the overhangs form duplex reinforcements along one or more edges of the structure, or span between two vertices of the structure.

30. The method of claim 28, wherein one or more of the overhangs comprise one or more sequences of nucleic acids complementary to a target RNA or DNA sequence.

31. The method of claim 28, wherein one or more of the overhangs comprise one or more sequences of nucleic acids that interact with DNA binding proteins or RNA-binding proteins.

32. The method of claim 28, wherein the edge length and geometry of the nucleic acid nanostructure is greater than the size of a target capture molecule allowing for 1, 2, 3, or more than 3 target capture molecules to be bound thereto independently of any other.

33. The method of claim 27, wherein the nanostructure has a molecular weight of between 200 Daltons and 100 mega Daltons, inclusive.

34. The method of claim 27, wherein the single-stranded scaffold comprises one or more nucleic acid sequences complementary to a nucleic acid sequence corresponding to one or more of an mRNA, DNA, or an epitope recognized by a DNA binding protein.

35. The method of claim 1, wherein the nucleic acid nanostructure comprises two nucleic acid parallel helices spanning each edge of the structure,
wherein the three-dimensional structure is formed from the single-stranded nucleic acid scaffold hybridized to itself and may also hybridize to single-stranded nucleic acid staple strands,
wherein the Euler cycle is defined by vertices and lines of the node-edge network,
wherein the scaffold hybridizes to itself in at least one edge using parallel crossovers,
and
wherein the staple strands, if any, are hybridized to the edges and double strand crossovers of the scaffold to define the shape of the nanostructure.

36. The method of claim 1, wherein the nucleic acid nanostructure further comprises a covalently or non-covalently bound molecule selected from the group consisting of PNA, protein, lipid, carbohydrate, a small-molecule, a dye, and RNA.

37. The method of claim 1, wherein the nucleic acid nanostructure further comprises comprising a therapeutic, diagnostic or prophylactic agent.

38. The method of claim 1 further comprising conjugating one or more molecules selected from the group consisting of PNA, protein, lipid, carbohydrate, a small-molecule, a dye, and RNA, to the nucleic acid nanostructure.

39. The method of claim 1, wherein assembling the nucleic acid nanostructure comprises synthesizing the single-stranded nucleic acid scaffold by a method comprising:
(i) amplifying a synthetic or naturally derived nucleic acid template by asymmetric polymerase chain reaction using a first oligonucleotide primer and a second oligonucleotide primer, and optionally a third oligonucleotide primer, or further oligonucleotide primer, to produce an amplified scaffold,
wherein the first primer, second primer, and third or further primers comprise a nucleic acid sequence complimentary to a portion of the sequence of the nucleic acid template,
wherein the first primer is present in greater molar concentration than the second, third or further primer,
wherein the first primer has a melting temperature that is between 1° C. and 99° C. lower than the melting temperature of the second, third or further primer; and
(ii) isolating the amplified scaffold.

40. The method of claim 39, wherein the first oligonucleotide primer further comprises a sequence of nucleic acids that is not complementary to the sequence of the nucleic acid template.

41. The method of claim 39, wherein the first oligonucleotide primer comprises deoxyribonucleic acid selected from the group consisting of naturally-occurring dNTP, dUTP, fluorescent dNTP, alpha-phosphate dNTP, radioactive dNTP, and polyethylene glycol-modified dNTP, or combinations thereof.

42. The method of claim 39, wherein the first oligonucleotide primer comprises a modification at the 5' terminus, wherein the modification is selected from the group consisting of phosphorylation or PEGylation of the nucleic acid, conjugation to a radioactive adduct, conjugation to a peptide, conjugation to an RNA, and conjugation to a lipid.

43. The method of claim 39, wherein the amplified scaffold sequence comprises deoxyribonucleic acid selected from the group consisting of naturally-occurring dNTP, dUTP, fluorescent dNTP, alpha-phosphate dNTP, radioactive dNTP, and polyethylene glycol-modified dNTP, and combinations thereof.

44. The method of claim 39, wherein the asymmetric polymerase chain reaction comprises contacting the template nucleic acid with a *Thermus aquaticus* DNA polymerase enzyme, and optionally one or more additional DNA polymerase enzymes.

45. The method of claim 39, wherein the first oligonucleotide primer is present at a concentration that is between 10-fold and 100-fold greater molar concentration than the second, third or further primer, preferably between 10-fold and 70-fold greater concentration than the second, third or further primer.

46. The method of the claim 1, wherein the node-edge network comprises interconnected edges comprising two nucleic acid duplexes.

47. The method of claim 46, wherein the two nucleic acid duplexes are inter-connected by antiparallel crossovers.

48. A method for making a nucleic acid nanostructure having a geometric shape comprising:
(a) determining or assigning the geometric parameters of an input, wherein the input comprises a 3D polyhedral or 2D polygonal geometric shape of a target nucleic acid nanostructure;
(b) identifying a route for a single-stranded nucleic acid scaffold that traces throughout the geometric shape comprising:
rendering a wireframe mesh of the geometric shape as a node-edge network;
using a spanning tree of the node-edge network to define the placement of scaffold crossovers;
determining a Euler cycle, wherein the single-stranded nucleic acid scaffold traces the Euler cycle throughout the node-edge network,
wherein (b) further comprises (b1), (b2), or (b3):
(b1) each edge of the network is classified based on its membership in the spanning tree, wherein edges that are members of the spanning tree do not have a scaffold double crossover, and edges that are not members of the spanning tree have a scaffold double crossover;

splitting each edge that is not a member of the spanning tree into two edges, each containing a pseudo-node at the point of the scaffold crossover;

splitting each node at each of the vertices into two pseudo-nodes; and wherein the Euler cycle represents a route of the single-stranded nucleic acid scaffold that traces once along each edge in both directions throughout the entire geometric shape;

(b2) each edge of the network is classified as one of four types based on its membership in the spanning tree and on whether it employs anti-parallel or parallel crossovers, wherein edges that are members of the spanning tree have each scaffold portion start and end at different vertices, and edges that are not members of the spanning tree have each scaffold portion start and end at the same vertex;

splitting each edge that is not a member of the spanning tree into two edges, each containing a pseudo-node at the point of the scaffold crossover;

splitting each node at each of the vertices into two pseudo-nodes; and wherein determining the Euler cycle comprises superimposing and connecting units of partial scaffold routing within an edge based on its classification and length;

(b3) rendering each helix in the network as a line based on a target cross-section of each edge;

calculating a loop-crossover structure, wherein two or more adjacent lines are connected to form loops and all possible double-crossover locations between two loops are calculated;

calculating a dual graph of the loop-crossover structure, wherein the loops and double-crossover locations of the network are converted to nodes and edges of the dual graph, respectively, wherein the spanning tree is of the dual graph network;

calculating which of the locations of double-strand crossovers will be used, wherein a single double-strand crossover is placed at each edge that is the part of the spanning tree of the dual graph; and wherein the Euler cycle represents a route of the single-stranded nucleic acid scaffold that traces once through each duplex throughout the entire geometric shape;

and (c) assembling the target nucleic acid nanostructure having the 3D polyhedral or 2D polygonal geometric shape comprising hybridizing the single-stranded nucleic acid scaffold to itself and/or staple strands to form the target nucleic acid nanostructure designed according to steps (a)-(b).

* * * * *